US007638120B2

(12) United States Patent
Liu et al.

(10) Patent No.: US 7,638,120 B2
(45) Date of Patent: Dec. 29, 2009

(54) HIGH TRANSGENE EXPRESSION OF A PSEUDOTYPED ADENO-ASSOCIATED VIRUS TYPE

(75) Inventors: Yuhong Liu, Cherry Hill, NJ (US); Jia Luo, Philadelphia, PA (US); Matthew During, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 10/427,129

(22) Filed: May 1, 2003

(65) Prior Publication Data

US 2004/0101514 A1 May 27, 2004

Related U.S. Application Data

(63) Continuation-in-part of application No. 09/804,898, filed on Mar. 13, 2001, now abandoned.

(60) Provisional application No. 60/189,110, filed on Mar. 14, 2000.

(51) Int. Cl.

| | |
|---|---|
| ***A01N 63/00*** | (2006.01) |
| ***C07H 21/02*** | (2006.01) |
| ***C07H 21/04*** | (2006.01) |

(52) U.S. Cl. .................... 424/93.6; 424/93.2; 536/23.1; 536/23.72; 536/24.1

(58) Field of Classification Search .............. 425/320.1; 435/455; 424/93.2, 93.21, 93.3, 93.6; 536/23.1, 536/23.72, 24.1

See application file for complete search history.

(56) References Cited

U.S. PATENT DOCUMENTS 6,491,907 B1 * 12/2002 Rabinowitz et al. ........ 424/93.2

OTHER PUBLICATIONS

Eck et al., 1996, Goodman & Gilman's The Pharmacological Basis of Therapeutics, McGraw-Hill, New York, p. 77-101.*
Gorecki, 2001, Expert Opin. Emerging Drugs, 6(2): 187-198.*
Davidson et al., 2000, PNAS, vol. 97, No. 7, p. 3428-3432.*
Rabinowitz et al., 2000, Virology, vol. 278, p. 301-308.*
Deonarain, M., 1998, Expert Opin. Ther. Pat., vol. 8, pp. 53-69.*
Verma et al., Sep. 1997, Nature, vol. 389, pp. 239-242.*
Burger et al., 2005, Human Gene Therapy, vol. 16, p. 781-791.*

* cited by examiner

*Primary Examiner*—Shin-Lin Chen
(74) *Attorney, Agent, or Firm*—Nutter, McClennen & Fish LLP; George A. Xixis

(57) ABSTRACT

The present invention related to methods and compositions comprising recombinant vectors comprising chimeric capsids and recombinant pseudotyped vectors with non-native capsid protein(s). The recombinant vectors of the invention confer an altered tropism that permits selective targeting of desired cells.

11 Claims, 3 Drawing Sheets

Figure 1. AAV plasmid s
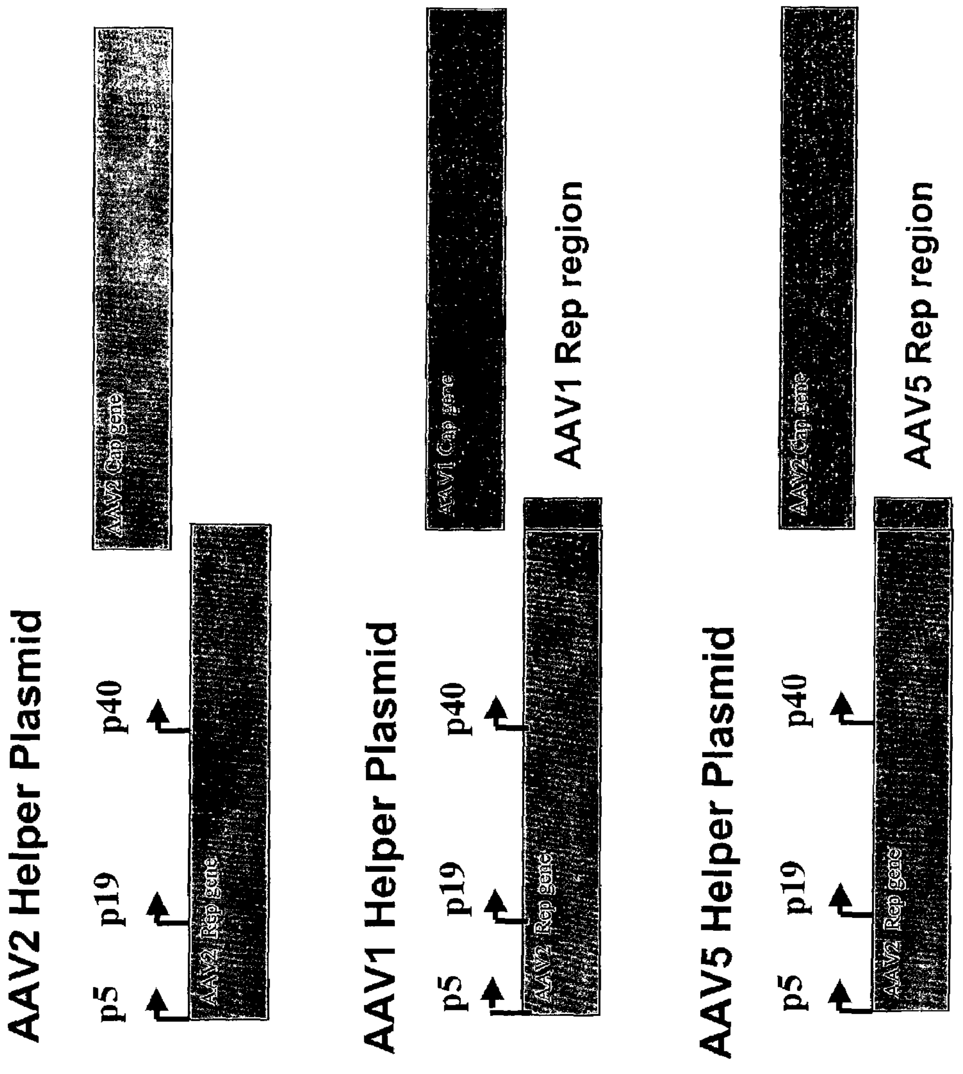

Fig. 2 The yield of AAV1, 2 and 5 (15 dishes)
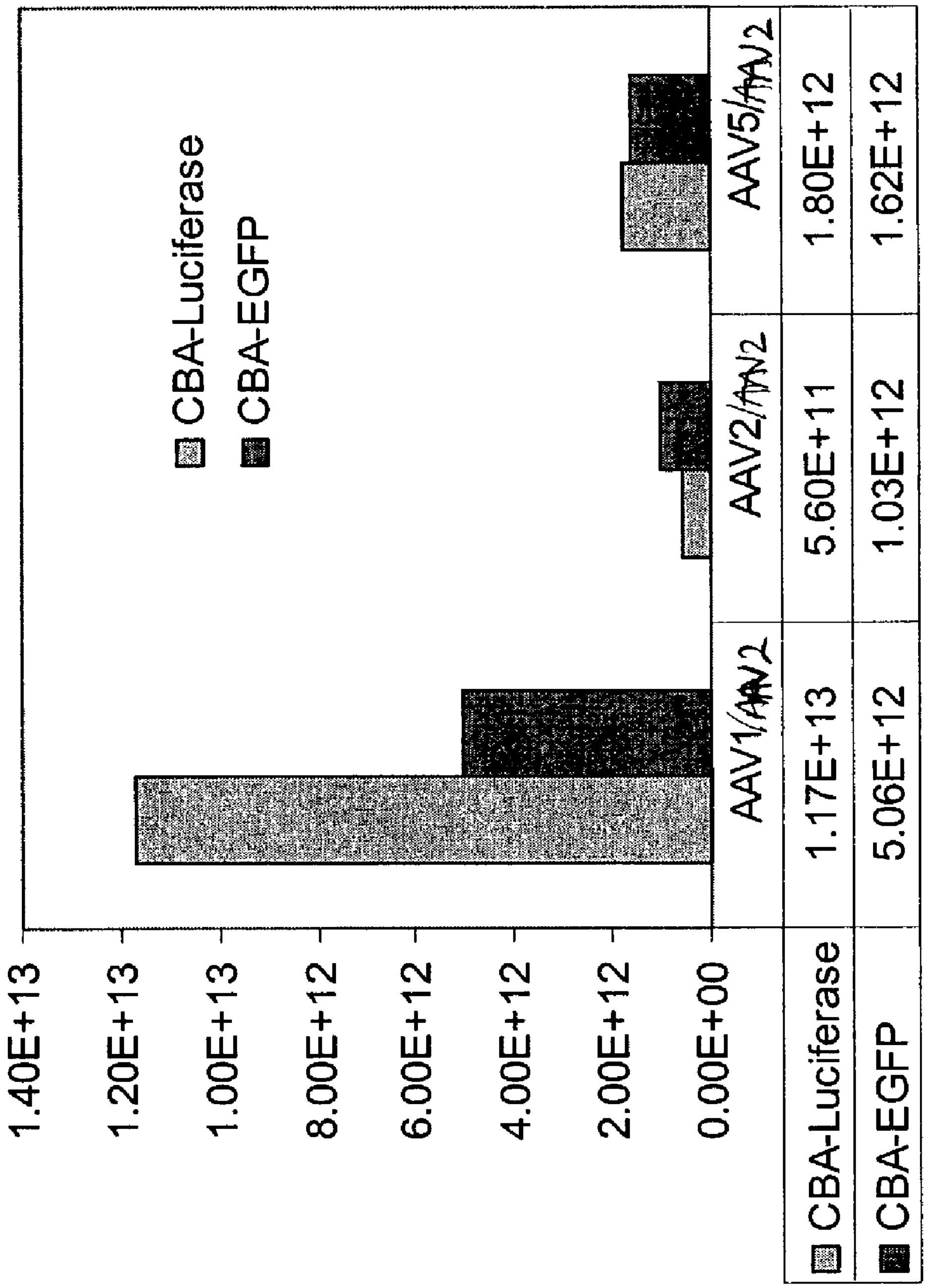

Fig. 3 The densitometry analysis of AAV-EGFP expression in the hippocampus
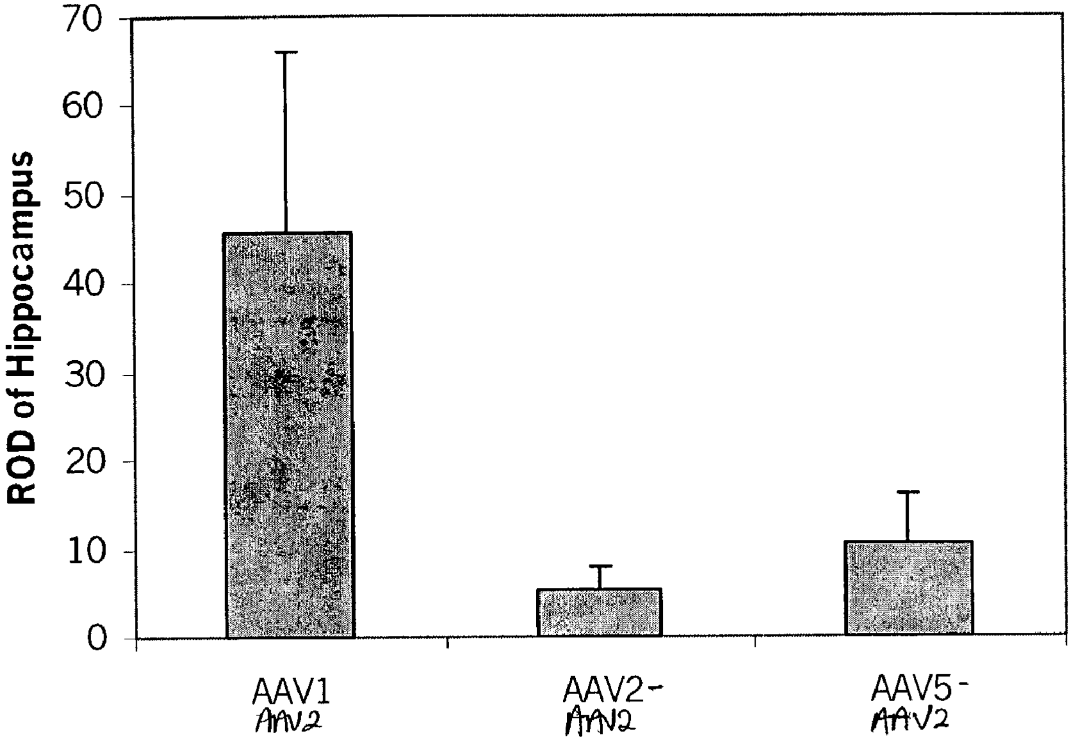

HIGH TRANSGENE EXPRESSION OF A PSEUDOTYPED ADENO-ASSOCIATED VIRUS TYPE

RELATED CASE INFORMATION

This application claims priority to U.S. Provisional Patent Application No. 60/189,110, filed Mar. 14, 2000 and is a continuation-in-part of U.S. patent application Ser. No. 09/804,898 filed: Mar. 13, 2001.

BACKGROUND OF THE INVENTION

The technical field of this invention is recombinant viral vectors and, in particular, recombinant pseudotyped viral vectors, especially recombinant pseudotyped adeno-associated viral (AAV) vectors.

Parvoviridae are small non-enveloped viruses containing single-stranded linear DNA genomes of 4 to 6 kb in length. Adeno-associated virus (AAV) is a member of the parvoviridae family. The AAV genome contains major open reading frames coding for the Rep (replication) and Cap (capsid) proteins. Flanking the AAV coding regions are two nucleotide inverted terminal repeat (ITR) sequences which contain palindromic sequences that can fold over to form hairpin structures that function as primers during initiation of DNA replication. In addition to their role in DNA replication, the ITR sequences have been shown to be necessary for viral integration, rescue from the host genome and encapsidation of viral nucleic acid into mature virions (Muzyczka, (1992) *Curr. Top. Micro. Immunol.* 158:97-129).

The capsids of parvoviridae have icosahedral symmetry and are about 20-24 nm in diameter. They are composed of three viral proteins (VP1, VP2, and VP3, which are approximately 87, 73 and 61 Kd, respectively) (Muzyczka supra). VP3 represents 90% of the total virion protein; VP2 and VP1 account for approximately 5% each.

AAV can assume two pathways upon infection of a host cell. In the presence of helper virus, AAV will enter the lytic pathway where the viral genome is transcribed, replicated, and encapsidated into newly formed viral particles. In the absence of helper virus function, the AAV genome becomes integrated as a provirus into a specific region of the host cell genome, through recombination between the AAV ITRs and host cell sequences. Specific targeting of AAV viral DNA occurs at the long arm of human chromosome 19 (Kotin et al., (1990) *Proc. Natl. Acad. Sci. USA* 87:2211-2215; Samulski et al., (1991) *EMBO J.* 10:3941-3950). This particular feature of AAV reduces the likelihood of insertional mutagenesis resulting from random integration of viral vector DNA into the coding region of a host gene.

The AAV vector has properties that make it unique for gene therapy, for example, AAV is not associated with any known diseases and is generally non-pathogenic. In addition, AAV integrates into the host chromosome in a site-specific manner (See e.g., Kotin et al., (1990) *Proc. Natl. Acad. Sci.* 87: 2211-2215 and Samulski et al., (1991) *EMBO J.* 10: 3941-3950). However, clinical trials have indicated that the low transduction rate and low titer of the virus often may limit its use as a therapy in the central nervous system (CNS).

The AAV viral vector uses cellular receptors to attach to and infect a cell. Recently identified receptors include a heparan sulfate proteoglycan receptor as the primary receptor, and either the fibroblast growth factor (FGF), or the integrin aVb5, as secondary receptors (Qing et al. (1999) *Nat. Med.* 5:71-77 and Summerford et al. (1999) *Nat. Med.* 5:78-82). Following attachment to the cell, the viral particle undergoes receptor-mediated internalization into clathrin-coated endocytic vesicles of the cell.

Although the AAV viral vectors provide a suitable means for gene delivery to a target cell, they may often display a limited tropism (i.e., the binding and entry of the virus into a cell) for particular cell types. To date, attempts to alter the tropism of AAV vectors have involved introducing a peptide ligand into the capsid coat. For example, Girod et al. introduced a 14 amino acid peptide containing the RDG motif of the laminin fragment P1 into a capsid region of the AAV2 serotype to alter tropism (Girod et al. (1999) *Nature Med.* 5: 1052-1056). Zavada et al. altered the tropism of an AAV vector by the addition of viral glycoproteins (Zavada et al. (1982) *J. Gen. Virol.* 63: 15-24). Others have added single chain fragments of variable regions of a monoclonal antibody against CD34 to the N-terminus of the VP2 capsid (Yang et al. (1998) *Hum. Gene. Ther.* 9: 1929-1937). The major limitation with these approaches is that they require additional steps that covalently link large molecules, such as receptor ligands and antibodies to the virus. This adds to the size of the virus as well as the cost of production. Furthermore, the targeted particles are not homogenous in structure, which may effect the efficiency of gene delivery and transfer. Therefore, a need exists to generate viral vectors with a modified tropism that interact more efficiently with a cell surface. A need also exists for viral vectors with a modified tropism to target cell types that the corresponding wild type virus does not typically target.

SUMMARY OF THE INVENTION

The invention is based on the discovery that a recombinant parvovirus vectors can be pseudotyped such that the recombinant vector is derived from a different virus than the capsid, e.g., a first parvovirus, is packaged with a capsid from a second parvovirus that is different from the first parvovirus. Such recombinant pseudotyped vectors have a modified tropism which allows them to interact with a cell surface molecule on a neural cell with an altered affinity. The recombinant pseudotyped vector is produced by packaging the wild type parvovirus vector in the capsid of a parvovirus other than the wild type. This can be accomplished, for example by using helper functions that comprise a rep coding region derived from the wild type parvovirus and a cap coding region derived from a parvovirus other than the wild type parvovirus. The resulting recombinant pseudotyped vector has a modified tropism that allows the recombinant pseudotyped vector to interact with a cell surface molecule on a neural cell with an altered affinity, e.g., a higher affinity, than a recombinant vector with a wild type capsid. Thus, the pseudotyped vector allows targeting of cells that a vector with a wild type capsid would not normally target, and permits targeting and infecting a broader range of cells and hosts compared with the wild type parvovirus. The pseudotyped vectors are particularly suitable for transduction into neural cells, for example, those present in regions of the brain.

More specifically, the invention pertains to recombinant pseudotyped adeno-associated vectors that carry the core genetic information of a first adeno-associated virus (AAV) type (i.e., the wild type AAV), and in addition the surface proteins of a second adeno-associated virus type that is different from the first adeno-associated virus type. For example, a recombinant AAV1, AAV2, AAV3, AAV4, AAV5, AAV6, and the like, genome may be encapsidated within any one of an AAV1, AAV2, AAV3, AAV4, AAV5, AAV6, and the like, capsid, provided that the AAV capsid and genome are of different types (or "serotypes").

In particularly preferred embodiments, the recombinant pseudotyped AAV virions comprise a wild type AAV2 type genome packaged within an AAV1, AAV3, AAV4, AAV5, AAV6 type capsid. In particular preferred embodiments, the recombinant pseudotyped AAV virion comprises a wild type AAV2 type genome packaged with an AAV1, or AAV5 type capsid. Most preferably, a wild type AAV2 genome packaged with an AAV1 type capsid. The present invention provides AAV helper function vectors that allow the genome to be packaged. These helper functions express rep gene products from the wild type AAV, and cap gene products from an AAV that is different from the wild type AAV to produce the recombinant pseudotyped virions of the invention.

Accordingly, in one aspect, the invention features a recombinant pseudotyped adeno-associated virion for use in neural cells comprising a transgene flanked 5' and 3' by inverted terminal repeat sequences, where the inverted terminal repeat sequences are derived from a first adeno-associated virus; and a non-native capsid derived from a second adeno-associated virus that is different from the first adeno-associated virus, such that the transgene is packaged within the non-native capsid, and where the non-native capsid provides a modified tropism and can bind to an attachment site present on a cell surface of a neural cell, with a higher affinity than a corresponding adeno-associated virion with a wild type capsid, and upon entering a cell has a transduction rate that is about 2-fold to about 30-fold higher than the transduction rate of the corresponding wild type adeno-associated virion. The the transduction rate can be determined by densiometry analysis.

The first adeno-associated virus type can be selected from the group consisting of AAV1, AAV2, AAV3, AAV4, AAV5, AAV6 and the like, while the second adeno-associated virus type can also be selected from the group consisting of AAV1, AAV2, AAV3, AAV4, AAV5, AAV6 and the like, as long as the second adeno-associated virus type is different from the first AAV. In one embodiment, the modified tropism permits attachment of the virion to an attachment site present on a neural cell, for example, a neural cell in a region of a brain. The modified tropism also permits binding and entry of the adeno-associated virus into the neural cell.

In another aspect, the invention features a recombinant pseudotyped adeno-associated virus type-1 virion comprising a transgene flanked 5' and 3' by inverted terminal repeat sequences, where the inverted terminal repeat sequences are derived from adeno-associated virus type-2 (AAV2); and a non-native capsid derived from adeno-associated virus type-1 (AAV1), such that the transgene is packaged within the AAV1 capsid, wherein the AAV1 capsid provides a modified tropism and can bind to an attachment site present on a cell surface of a neural cell with a higher affinity than a corresponding adeno-associated virion with a wild type capsid, and upon entry into a cell has a transduction rate that is about 8-fold higher than the transduction rate of the corresponding wild type adeno-associated virion with a wild type capsid.

In yet another aspect, the invention features a recombinant pseudotyped adeno-associated virus type-5 virion comprising a transgene flanked 5' and 3' by inverted terminal repeat sequences, where the inverted terminal repeat sequences are derived from adeno-associated virus-2 (AAV2); and a non-native capsid derived from adeno-associated virus-5 (AAV5), such that the transgene is packaged within the AAV5 capsid, wherein the AAV5 capsid provides a modified tropism and can bind to an attachment site present on a cell surface of a neural cell with a higher affinity than a corresponding adeno-associated virion with a wild type capsid, and upon entry into a cell has a transduction rate that is about 2-fold higher than the transduction rate of the corresponding wild type adeno-associated virion with a wild type capsid.

In another aspect, the invention features a method of making a recombinant pseudotyped adeno-associated virions by providing a first construct comprising a transgene flanked 5' and 3' with inverted terminal repeat sequences derived from a first adeno-associated virus type, where at least one inverted terminal repeat sequence comprises a packaging signal, and a second helper construct comprising a rep coding region derived from the first adeno-associated virus type and a cap coding region derived from a second adeno-associated virus type, wherein the cap coding region encodes a non-native capsid. A population of cells is contacted with the first and second constructs, such that the population of cells allows assembly of a recombinant virion, to thereby produce a recombinant pseudotyped virion, wherein the recombinant pseudotyped virion has a modified tropism and can bind to an attachment site present on a cells surface of a neural cell, and has a transduction rate that is about 2-fold to about 30-fold higher than the transduction rate of the corresponding wild type adeno-associated virion with a wild type capsid.

The inverted terminal repeat sequences of the first construct can be derived from an adeno-associated virus type selected from the group consisting of AAV1, AAV2, AAV3, AAV4, AAV5, AAV6 and the like. In a preferred embodiment, the inverted terminal repeat sequences are derived from the wild type AAV, e.g., AAV2. The second construct can comprise a nucleic acid sequence encoding a capsid derived from an adeno-associated virus type that is different from the first adeno-associated virus type. The recombinant pseudotyped adeno-associated virion can be made by contacting a population of 293 cells.

In yet another aspect, the invention features a method for modifying the tropism of a recombinant adeno-associated viral vector comprising replacing a native capsid of a first adeno-associated virus type with a non-native capsid derived from a second adeno-associated virus type; and combining the non-native capsid under conditions for assembly, to thereby modify the tropism of an adeno-associated viral vector.

In one embodiment, the non-native capsid can be derived from an adeno-associated virus type selected from the group consisting of AAV1, AAV2, AAV3, AAV4, AAV5, AAV6 and the like. In a preferred embodiment, the non-native capsid is derived from AAV1. In another preferred embodiment, the non-native capsid is derived from AAV5.

The method for modifying the tropism of a recombinant adeno-associated viral vector can further comprise increasing the efficiency of entry into a cell using a recombinant pseudotyped adeno-associated viral vector by providing a transgene flanked 5' and 3' by inverted terminal repeat sequences, where the inverted terminal repeat sequences are derived from a first adeno-associated virus type, and a non-native capsid derived from a second adeno-associated virus, where the capsid has a modified tropism; and contacting a cell with the recombinant pseudotyped adeno-associated viral vector having a modified capsid tropism such that the non-native capsid binds to an attachment site on the cell surface of a neural cell, and permits the vector to enter the neural cell more efficiently that a corresponding viral vector comprising a wild type capsid. In a preferred embodiment, the inverted terminal repeat sequences are derived from AAV2 and the non-native capsid is derived from AAV1. In another embodiment, the inverted terminal repeat sequences are derived from AAV2 and the non-native capsid is derived from AAV5. The attachment site can be a site on a neural cell, e.g., a neuronal cell in a region of a brain.

In another aspect, the invention features an isolated nucleic acid molecule encoding an AAV helper function. The nucleic acid molecule comprises a rep coding region derived from a first adeno-associated virus type, where the first adeno-associated virus is the wild type virus, and a cap coding region derived from a second adeno-associated virus type that is different from the first virus. The non-native capsid provides a modified tropism which permits binding to an attachment site present on a cell surface of a neural cells with a higher affinity than a corresponding adeno-associated virion with a wild type capsid, and which upon entry into a cell has a transduction rate that is about 2-fold to about 30-fold higher than the transduction rate of the corresponding wild type adeno-associated virion.

BRIEF DESCRIPTION OF FIGURES

FIG. 1 is a schematic showing the pseudotyped helper function constructs;

FIG. 2 is a bar graph showing the yields of AAV pseudotyped vectors; and

FIG. 3 is a bar graph showing the densitrometric analysis of EGFP expression in the hippocampus.

DETAILED DESCRIPTION

The present invention is based on the discovery that a recombinant pseudotyped adeno-associated virus (AAV) vector can be packaged efficiently producing a recombinant vector with a capsid that confers a modified tropism to the vector. The modified tropism allows the recombinant pseudotyped vector to bind to attachment sites on neural cells, with an altered affinity, e.g., a higher affinity, than a recombinant vector with wild type capsid. Alternatively, the modified tropism allows targeting of cells that would not typically be targeted by an AAV vector with a wild type capsid. These recombinant pseudotyped vectors with the modified tropism are produced by using a non-native capsid derived from an adeno-associated virus that is different from the wild type adeno-associated virus, and the genome of the wild type AAV is packaged within the non-native capsid. Alternatively, the altered tropism can be the result of recombinant vectors comprising chimeric capsids. The recombinant vector with chimeric capsids has at least one non-native amino acid sequence derived from a capsid protein from another member of the parvovirus family, and also contains a packaging sequence in the genome that can be derived from the wild type parvovirus or can be derived from another family member.

So that the invention is more clearly understood, the following terms are defined:

The term "parvoviruses" as used herein refers to any member of the subfamily Parvovirinae. It includes both autonomous parvovirus and dependovirus. The present invention include, but are not limited to, LuIII parvovirus (LuIII), minute virus of mice (MVM; e.g., MVMi and MVMp), hamster parvovirus (e.g., H1), feline panleukopenia virus, canine parvovirus, porcine parvovirus, latent rat virus, mink enteritis virus, human parvovirus (e.g., B19), bovine parvovirus, Aleutian mink disease parvovirus, adeno-associated viruses (e.g., AAV1, AAV2).

The term "pseudotyped" as used herein refers to mixed viral particles (or virions). These "pseudotyped" viral particles carry the core and genetic information of first virus, and in addition the surface capsid protein(s) of second different virus. The term "pseudotyped" is also intended to encompass surface capsid proteins of other viruses with point mutations (additions, substitutions, and deletions).

The term "pseudotyped adeno-associated virion" as used herein refers to mixed adeno-associated viral particles. These "pseudotyped" adeno-associated particles carry the core and genetic information of a first adeno-associated virus, and in addition the surface capsid protein(s) of a second different adeno-associated virus.

The term "chimeric capsid" as used herein refers to a viral protein coat with one or more non-native amino acid sequences. The chimeric capsid can comprise a combination of amino acid sequences from the same family. For example, a chimeric capsid comprising the VP1 domain of AAV2, in combination with the VP2 and VP3 domains of AAV5. The skilled artisan will appreciate that the chimeric capsid can be any combination of viral protein domains from the parvovirus family member such as, AAV1, AAV2, AAV3, AAV4, AAV5, AAV6 and the like. The term "chimeric capsid" also refers to a viral protein coat with at least one non-native amino acid sequence from a virus, such as herpesvirus, adenovirus, lentivirus, retrovirus, Epstein-Barr virus and vaccinia virus, and the like.

The term "non-native capsid" as used herein refers to an entire capsid protein that is not present in the wild type parvovirus. For example, the non-native capsid protein can be the entire capsid derived from an AAV, such as AAV1 that replaces the entire capsid of a wild type AAV, such as AAV2. The term "non-native capsid" is also intended to a include nucleic acid molecule encoding the non-native capsid protein.

The term "tropism" as used herein refers to the binding (or attachment) and entry (or internalization) of the virus into the cell, optionally and preferably, followed by expression of sequences carried by the viral genome in the cell.

The term "modified tropism" as used herein refers to a recombinant parvovirus that has an altered tropism, which allows the parvovirus to target cells that the wild type virus with a wild type capsid was unable to target. The term "modified tropism", includes reductions or enhancements in infectivity with respect to a particular cell type(s) as compared with the wild type parvovirus. These reductions or enhancements can arise due to a change in the binding or attachment of the virus to a target cell, that the wild type virus is unable to target. Alternatively, these reductions or enhancements can arise due to a change in the entry or internalization of the virus into the target cell.

The term "modified tropism" also encompasses the creation of a new tropism i.e., creating a parvovirus that infects a particular cell type(s) to a significant or a detectable extent that the wild type parvovirus was unable to infect. Preferred cell types are those of the central nervous system, e.g., neural cells of the brain. As a further alternative, a "modified tropism" also refers to a more efficient delivery of a targeted parvovirus as compared with the native parvovirus (e.g., a reduced Multiplicity of Infection, "MOI").

The term "affinity" as used herein refers to the art recognized use of the term for the attraction between a ligand and receptor. An "altered affinity" is one that has an increased (i.e., a stronger attraction) or decreased (i.e., a weaker attraction) between ligand and receptor.

The term "transduction rate" as used herein refers to its the introduction of a nucleic acid sequence contained in a pseudotyped viral vector into a number of cells. Transduction by a method of the invention involves contacting cells with a viral vector such that the viral nucleic acid enters the cell and can be expressed therein. The rate of transduction can be determined by measuring the number of the cells that are transduced and by examining the extent of expression of a protein at a target site by certain amount of virus (by particle). If a vector is administered, the extent of transduction of cells can be determined by examining the distance away from an injection site that protein expression occurs. The more further away from the point of injection that expression can occurs, the greater number of cells that are transduced. The transduction rate for the pseudotyped vectors can be determined by standard techniques. For example, the rate of transduction can be assessed sterologically by counting the number of cells expressing a marker protein, such as Green Fluorescent Protein (GFP) in a region of a brain into which the recombinant vectors of the invention have been delivered. Serial continuous brain sections can be made around the injection site, e.g., approximately 50 sections, and the number of cells expressing the GFP in each brain section counted using a microscope. The sum total number of transduced cells from each brain section can be counted to provide an evaluation of the transduction rate for each of the recombinant pseudotyped vectors, or recombinant chimeric capsid vectors.

Under circumstances where sterological counting is impractical, for example where there is strong expression of the marker protein that makes it difficult to assess the number of cells expressing the marker protein, fluorescent microscopic densitometry can be used to determine the fluorescence intensity of marker protein, e.g., GFP in the target nuclei. The fluorescent images of each brain section can be captured by a digital camera under the fluorescent microscope and the relative fluorescent intensity in the transduced nuclei of each image can be analyzed by using the NIH image software. With densiometry analysis, color images of a marker protein such as GFP, are analyzed as a black and white images. The area that appears as bright white indicates highest expression of the marker protein, a grey scale indicates a lower-expression, and a black scale indicates no expression of the marker protein. The rate of transduction can be determined by examining the area of "white" in a region of the brain. The greater the area of white in an image, the greater the expression of the marker protein in that region.

Another method of determining transduction rates can be by measuring luciferase activity of transduced cells using the Luciferase Assay Reagent Kit (Promega, Madison, Wis., U.S.A) according to the manufacturer's recommendations to measure the luciferase activity of cell lysates using a luminometer. Preferably the transduction rate is about 2 fold to about 30 fold higher in neural cells using the recombinant pseudotyped vectors or the recombinant chimeric capsid vectors, compared with the wild type vector having a wild type capsid.

The term "attachment site" as used herein refers to a site on a target cell to which the recombinant pseudotyped parvovirus binds to, or interacts with. The recombinant pseudotyped vectors have a modified tropism to facilitate binding of AAV to the cellular receptor, or to inhibit the binding to the receptor. In particular, the attachment site is one that is not typically targeted by a wild type virion, but is one that is targeted by the pseudotyped vector of the invention. For example, by binding to an attachment site on neural cells, e.g., an attachment site on a neural cell in a region of the brain or spinal cord.

The term "gene transfer" or "gene delivery" as used herein refers to methods or systems for reliably inserting foreign nucleic acids sequences, e.g., DNA into host cells. Such methods can result in transient expression of non-integrated transferred DNA, extra-chromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells (See, e.g., U.S. Pat. No. 5,399,346.)

The term "transgene", as used herein refers to a nucleic acid sequence of interest. Such transgenes, or gene sequences, may be derived form a variety of sources including DNA, cDNA, synthetic DNA, and RNA. Such transgenes may comprise genomic DNA which may or may not include naturally occurring introns. Moreover, such genomic DNA may be obtained in association with promoter regions or poly A sequences. The transgenes of the present invention are preferably cDNA. Genomic or cDNA may be obtained by means well known in the art. A transgene which may be any gene sequence whose expression produces a gene product that is to be expressed in a cell. The gene product may affect the physiology of the host cell. Alternatively the transgene may be a selectable marker gene or reporter gene.

The term "transgene expression cassette" refers to a transgene that is operably linked to a promoter or other regulatory sequence sufficient to direct transcription of the transgene. Suitable promoters include, for example, tissue specific promoters. Other regulatory sequences include post-regulatory sequences such as the woodchuck post-regulatory sequence.

The term "tissue-specific promoter" as used herein refers to a promoter that is operable in cells of the central nervous system (CNS), such as neural cells. Examples of promoters for the CNS include but are not limited to, neuron-specific promoters (e.g., the neurofilament promoter; Byrne and Ruddle (1989) *Proc. Natl. Acad. Sci. USA* 86:5473-5477) and glial specific promoters (Morii et al. (1991) *Biochem. Biophys Res. Commun.* 175: 185-191). Preferably, the promoter is tissue specific and is essentially not active outside the central nervous system, or the activity of the promoter is higher in the central nervous system that in other systems. For example, a promoter specific for the spinal cord, brainstem, (medulla, pons, and midbrain), cerebellum, diencephalon (thalamus, hypothalamus), telencephalon (corpus stratium, cerebral cortex, or within the cortex, the occipital, temporal, parietal or frontal lobes), subthalamic nucleus (STN), substantia nigra (SN), or combinations, thereof. Preferred promoters are the Chicken Beta Actin (CBA) promoter and the neuron-specific enolase (NSE) promoter. The promoter may also be one that can be used in combination with an AAV to result in higher expression. For example, a cytomegalovirus enhancer/Chicken-Beta-Actin (CBA) hybrid promoter that functions in cells of the CNS (Xu et al. (2001) *Hum Gene Ther.* 12:563-73).

A "nucleic acid sequence" refers to a DNA or RNA sequence. The term-captures sequences that include any of the known base analogues of DNA and RNA such as, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, 2-thiocytosine, and 2,6-diaminopurine.

The term "vector" as used herein refers to any genetic element, such as a plasmid, phage, transposon, cosmid, chromosome, virus, adeno-associated virus, parvovirus, virion, and the like, which is capable of replication when associated with the proper control elements and which can transfer gene sequences into cells. Thus, the term includes cloning and expression vehicles, as well as viral vectors.

The term "AAV vector" as used herein refers to a vector derived from an adeno-associated virus serotype, including but not limited to, AAV1, AAV2, AAV3, AAV4, AAV5, AAV6, and the like. AAV vectors can have one or more of the AAV wild-type genes deleted in whole or part, preferably the rep and/or cap genes, but retain functional flanking Inverted Terminal Repeat (ITR) sequences. Functional ITR sequences permit the rescue, replication and packaging of the AAV virion. Thus, an AAV vector is defined herein to include at least those sequences required for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

The term "regulatory sequence" is art-recognized and intended to include control elements such as promoters, enhancers and other expression control elements (e.g., polyadenylation signals), transcription termination sequences, upstream regulatory domains, origins of replication, internal ribosome entry sites ("IRES"), enhancers, enhancer sequences, post-regulatory sequences and the like, which collectively provide for the replication, transcription and translation of a coding sequence in a recipient cell. Not all of these regulatory sequences need always be present so long as the selected coding sequence is capable of being replicated, transcribed and translated in an appropriate host cell. Such regulatory sequences are known to those skilled in the art and are described in Goeddel, *Gene Expression Technology: Methods in Enzymology* 185, Academic Press, San Diego, Calif. (1990). It should be understood that the design of the viral vector may depend on such factors as the choice of the host cell to be transfected and/or the amount of protein to be expressed.

The term "operably linked" as used herein refers to an arrangement of elements wherein the components are configured so as to perform their usual function. Thus, control elements operably linked to a coding sequence are capable of effecting the expression of the coding sequence. The control elements need not be contiguous with the coding sequence, so long as they function to direct the expression of the coding sequence. For example, intervening untranslated yet transcribed can be present between a promoter sequence and the coding sequence and the promoter sequence can still be considered "operably linked" to the coding sequence.

The term "AAV rep coding region" as used herein refers to the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other exogenous) promoters. The Rep expression products are collectively required for replicating the XAV genome. For a description of the AAV rep coding region, see, e.g., Muzyczka (1992) *Current Topics in Microbiol. and Immunol.* 158:97-129; and Kotin (1994) *Human Gene Therapy* 5:793-801. Suitable homologues of the AAV rep coding region include the human herpesvirus 6 (HHV-6) rep gene which is also known to mediate AAV2 DNA replication (Thomson et al. (1994) *Virology* 204:304-311). In certain embodiment of the invention, the rep coding region can be derived from any AAV serotype including, but limited to AAV1, AAV2, AAV3, AAV4, AAV5, AAV6, etc. In a preferred embodiments, the rep coding region is derived from AAV2.

The term "AAV cap coding region" as used herein refers to the art-recognized region of the AAV genome which encodes the capsid proteins VP1, VP2, and VP3, or functional homologues thereof. These cap expression products supply the packaging functions which are collectively required for packaging the viral genome. For a description of the AAV cap coding region, See, e.g., Muzyczka (Supra). In certain embodiment, the AAV cap coding region can be derived from any AAV serotype, including, but not limited to AAV1, AAV2, AAV3, AAV4, AAV5, AAV6, etc. In a preferred embodiment, the entire cap coding region is derived from AAV1. In certain embodiment, the entire cap coding region is derived from AAV5.

The term "AAV helper functions" or "helpers" as used herein refer to AAV-derived coding sequences that can be expressed to provide AAV gene products that, in turn, function in trans for productive AAV replication. Thus, AAV helper functions include the rep and cap regions. The rep expression products have been shown to possess many functions, including, among others: recognition, binding and nicking of the AAV origin of DNA replication; DNA helicase activity; and modulation of transcription from AAV (or other heterologous) promoters. The cap expression products supply necessary packaging functions. AAV helper functions are used herein to complement AAV functions in trans that are missing from AAV vectors.

The term "pseudotyped AAV helper functions" as used herein refers to rep and cap regions where the cap region is derived from an AAV that is different from the wild type genome. In preferred embodiment, the helper functions comprise a rep coding region derived from a first adeno-associated virus, that is the wild type adeno-associated virus, and the non-native cap coding region is derived from a adeno-associated virus that is different from the wild type adeno-associated virus. In one embodiment, the AAV helper function comprises a wild type rep region derived from AAV2, and a non-native cap coding region derived from AAV1. In another embodiment, the AAV helper function comprises a wild type rep region from AAV2, and a non-native cap coding region from AAV5.

The term "accessory functions" as used herein refers to non-AAV derived viral and/or cellular functions upon which AAV is dependent for its replication (Carter, (1990) "Adeno-Associated Virus Helper Functions," in CRC Handbook of Parvoviruses, vol. I (P. Tijssen, ed.)). Thus, the term captures DNAs, RNAs and protein that are required for AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus (other than herpes simplex virus type-1) and vaccinia virus.

The term "accessory function vector" as used herein refers generally to a nucleic acid molecule that includes nucleotide sequences providing accessory functions. An accessory function vector can be transfected into a suitable host cell, wherein the vector is then capable of supporting AAV virion production in the host cell. Thus, accessory function vectors can be in the form of a plasmid, phage, transposon, cosmid or virus that has been modified from its naturally occurring form.

The term "recombinant virus" as used herein refers to a virus that has been genetically altered, e.g., by the addition or insertion of a heterologous nucleic acid construct into the particle.

The term "recombinant virion" as used herein refers to a complete infectious, replication-defective virus particle composed of a viral coat, encapsidating a transgene which is flanked on both sides by viral ITRs. The term "recombinant virion" is used synonymously with the term "recombinant particle."

The term "recombinant AAV virion," or "recombinant AAV particle" as used herein refers to an infectious, replication-defective virus composed of an AAV protein shell encapsidating a heterologous nucleotide sequence of interest that is flanked on both sides by AAV ITRs. A recombinant AAV virion is produced in a suitable host cell comprising an AAV vector, AAV helper functions, and/or accessory functions. In this manner, the host cell is rendered capable of encoding AAV polypeptides that are required for packaging the AAV vector (comprising a recombinant nucleotide sequence of interest) into infectious recombinant virion particles for subsequent gene delivery.

The terms "5'", "3'", "upstream" or "downstream" are art recognized terms that describe the relative position of nucleotide sequences in a particular nucleic acid molecule relative to another sequence.

The term "transfection" is used herein refers to the uptake of an exogenous nucleic acid molecule by a cell. A cell has been "transfected" when exogenous nucleic acid has been introduced inside the cell membrane. A number of transfection techniques are generally known in the art. See, e.g., Graham et al. (1973) *Virology,* 52:456, Sambrook et al. (1989) *Molecular Cloning, a laboratory manual*, Cold Spring Harbor Laboratories, New York, Davis et al. (1986) *Basic Methods in Molecular Biology,* Elsevier, and Chu et al. (1981) *Gene* 13:197. Such techniques can be used to introduce one or more exogenous nucleic acid molecules into suitable host cells. The term refers to both stable and transient uptake of the nucleic acid molecule, and is intended to capture captures chemical, electrical, and viral-mediated transfection procedures.

The term "coding sequence" or a sequence which "encodes" a particular protein, as used herein refers to a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

A "fragment" or "portion" of a nucleic acid encoding a capsid protein is defined as a nucleotide sequence having fewer nucleotides than the nucleotide sequence encoding the entire amino acid sequence of the capsid protein, such as VP1, VP2 or VP3. A fragment or portion of a nucleic acid molecule is about 10 nucleotides, about 20 nucleotides, about 30 nucleotides, about 40 nucleotides, and about 50 nucleotides in length. Also within the scope of the invention are nucleic acid fragments which are about 60, 70, 80, 90, 100 or more nucleotides in length. Preferred fragments or portions include nucleotide sequences encode a polypeptide that alters the tropism of the chimeric capsid. The term fragment or portion also refers to an amino acid sequence of the capsid protein that has fewer amino acids than the entire sequence of the viral protein domains VP1, VP2 and VP3. The fragment is about 10 amino acids, more preferably about 20, 30, 40, 50, 60, 70, 80, 90, 100, 120, 140, 160, 180 and 200 or more amino acids in length.

The terms "polypeptide" and "protein" are used interchangeably herein and refer to a polymer of amino acids and includes full-length proteins and fragments thereof. As will be appreciated by those skilled in the art, the invention also includes nucleic acids that encode those polypeptides having slight variations in amino acid sequences or other properties from a known amino acid sequence. Amino acid substitutions can be selected by known parameters to be neutral and can be introduced into the nucleic acid sequence encoding it by standard methods such as induced point, deletion, insertion and substitution mutants. Minor changes in amino acid sequence are generally preferred, such as conservative amino acid replacements, small internal deletions or insertions, and additions or deletions at the ends of the molecules. These modifications can result in changes in the amino acid sequence, provide silent mutations, modify a restriction site, or provide other specific mutations. Additionally, they can result in a beneficial change to the encoded protein.

The term "homology" or "identity" as used herein refers to the percentage of likeness between nucleic acid molecules. To determine the homology or percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) *J. Mol. Biol. (*48):444-453) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In another example, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In yet another example, the percent identity between two amino acid or nucleotide sequences is determined using the algorithm of E.

Meyers and W. Miller (CABIOS, 4:11-17 (1989)) which has been incorporated into the ALIGN program (version 2.0), using a PAM120 weight residue table, a gap length penalty of 12 and a gap penalty.

The term "host cell" as used herein refers to, for example microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement to the original parent, due to natural, accidental, or deliberate mutation.

The term "cell line" as used herein refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

The term "central nervous system" or "CNS" as used herein refers to the art recognized use of the term. The CNS pertains to the brain, cranial nerves and spinal cord. The CNS also comprises the cerebrospinal fluid, which fills the ventricles of the brain and the central canal of the spinal cord. Regions of the brain include, but are not limited to, the striatum, hippocampus, cortex, basal ganglia, subthalmic nucleus (STN), pedunculopontine nucleus (PPN), substantia nigra (SN), thalamus, putamen, or caudate regions of the brain, as well as the spinal cord or combinations thereof.

The term "neural cells" as used herein refers to cells that have been isolated from the brain, spinal cord or cells from any region of the central nervous system, as well as any cell present in the brain, spinal cord, or central nervous system of a subject, to which the recombinant psuedotype vectors, or the recombinant chimeric capsid vectors with a modified tropism, attach to, enter, and express a transgene, with a higher affinity or transduction rate than the corresponding vector with a vectors with a wild type capsid. Examples of neural cells include neuronal cells, such as nerve cells that transmit nerve or chemical signals to and from the brain, such as sensory neurons or bipolar neurons that carry messages from the body's sense receptors (eyes, ears, etc.) to the CNS; motoneurons or multipolar neurons cells that carry signals from the muscles and glands to the CNS (e.g., spinal motor neurons, pyramidal neurons, Purkinje cells.); interneurons or pseudopolare cells which form the neural wiring within the CNS. These have two axons (instead of an axon and a dendrite).

The term neural cells is also intended to include glial cells, which make up 90 percent of the brain's cells. Glial cells are nerve cells that do not carry nerve impulses. Types of glial cells include, but are not limited to, Schwann's cells, satellite cells, microglia, oligodendroglia, and astroglia.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

Further details of the invention are described in the following sections:

I Recombinant Vectors

The invention features a method of producing recombinant vectors comprising a chimeric capsid or recombinant pseudotyped vectors that are particularly suitable for targeting cells in the central nervous system, e.g., cells in a region of the brain. Recombinant vectors can be constructed using known techniques to provide operatively linked components of control elements including a transcriptional initiation region, a transgene, and a transcriptional termination region. The control elements are selected to be functional in the targeted cell. The resulting construct which contains the operatively linked components can be flanked at the 5' and 3' region with functional parvoviral ITR sequences.

In one aspect, the invention features a recombinant pseudotyped parvovirus vector that comprises a wild type parvovirus genome, and a non-native capsid derived from a parvovirus that is different from the wild type parvovirus. In one embodiment, the recombinant pseudotyped parvovirus vector is a recombinant pseudotyped AAV vector.

The parvovirus family includes adeno-associated viruses. Examples of adeno-associated virus serotypes include, but are not limited to, AAV1 (Xiao et al. (1999), *J. Virol.,* 73: 3994-4003, GenBank Accession No. AF063497; gi:9632547), AAV2 (Ruffing et al. (1994) *J. Gen. Virol.,* 75: 3385-3392, GenBank Accession No. gi:9626146), AAV3 (Muramatsu et al. (1996) *Virology* 221: 208-217, GenBank Accession No. U48704; Rutledge et al. (1998) *J. Virol.,* 72: 309-319, GenBank Accession No. AF028705), AAV4 (Chiorini et al. (1997), *J. Virol.,* 71: 6823-6833, GenBank Accession No. U89790), AAV5 (Bantel et al., (1999), *J. Virol.* 73: 939-947 GenBank Accession No. gi:4249656) and AAV6 (Rutledge et al. (1998), *J. Virol.,* 72: 309-319, GenBank Accession No. AF028704). The sequences of the capsid genes for such serotypes is reported in Srivastava et al., (1983) *J. Virol.* 45:555-564; Muzyczka (1992) *Curr. Top. Micro Immunol.* 158:97-129, and Ruffing et al. (1992) *J. Virol.* 66:6922-6930. Each serotype of AAV has a different cellular tropism and bind to different cell surface proteins. Some parvovirus family members are useful for transduction of particular cell types, but less useful for transduction of other cells.

Several serotypes of adeno-associated viruses AAV have been reported (Bantel-Schaal et al. (1999) *J. Virol.* 73:939-947 and Chiorini (1999) *J. Virol.* 73:1309-1319 (AAV5); Chiorini, et al. (1997) *J. Virol.* 71:6823-6833 (AAV4); Muramatsu et al. (1996) *Virology* 221:208-217 (AAV3); Rutledge et al. (1998) *J. Virol.* 72:309-319; and Xiao et al. (1999) *J. Virol.* 73:3994-4003 (AAV2)). Cloning and sequence characterization of these serotypes indicate that they share a similar genomic organization, which consists of two large open reading frames (ORFs) flanked by two inverted terminal repeats (ITRs). The ITR structure is the minimal sequence required for AAV DNA replication, provirus integration, and packaging of progeny AAV DNA into virus particles. The left ORF encodes four nonstructural Rep proteins. These proteins not only are the regulators of AAV transcription (Labow et al. (1986) *J. Virol.* 60:251-258) but also are involved in AAV replication (Snyder et al. (1990) *J. Virol.* 64:6204-6213) and virus assembly (King et al. (2001) *EMBO J.* 20:3282-3291) and play a role in site-specific integration of the viral genome into the host chromosome during latent infection (Linden et al. (1996) *Proc. Natl. Acad. Sci. USA* 93:11288-11294). The sequences of the Rep ORFs of AAV2, AAV3, AAV4, and AAV6 are approximately 85% identical, but AAV5 has only 54.5% homology with the other AAV serotypes (Chiorini et al. (1999) *J. Virol.* 73:1309-1319). The right half of the AAV genome encodes three viral capsid proteins referred to as VP1, VP2, and VP3 and is less conserved than the Rep ORF. AAV2, AAV3, and AAV6 share about 80% homology in the amino acid sequences of the capsid proteins. However, an alignment of the capsid protein ORFs of all six serotypes results in a reduction of the overall amino acid identity to less than 45% (Bantel-Schaal et al. (1999) *J. Virol.* 73:939-947). This diversity in the capsid protein sequences is likely the basis for differences in the serological characteristics and altered tissue tropism among the six AAV serotypes.

A particularly preferred parvovirus is the adeno-associated virus-2 (AAV2). The AAV2 sequence is available through Genbank under accession no. gi:9626146. AAV2 has a broad host range and until recently, all human cells were thought to be infectable. However, certain cells of the central nervous system are inaccessible with AAV2. For example, AAV2 has poor tropism for human myeloid stem cells, or cells from the lymphocyte lineage. AAV2 is not associated with any disease, therefore making it safe for gene transfer applications (Cukor et al. (1984), *The Parvoviruses, Ed. K. I. Bems, Plenum, N.Y.,* 33-36; Ostrove et al. (1981), *Virology* 113: 521). AAV2 integrates into the host genome upon infection so that transgene can be expressed indefinitely (Kotin et al. (1990), *Proc. Natl. Acad. Sci. USA* 87: 221; Samulski et al.(1991), *EMBO J.* 10: 3941). Integration of AAV2 into the cellular genome is independent of cell replication which is particularly important since AAV can thus transfer genes into quiescent cells (Lebkowski et al. (1988), *Mol. Cell. Biol.* 8: 3988).

Another particularly preferred parvovirus is the adeno-associated virus-1 (AAV1). The AAV 1 sequence is available through GenBank under accession no. gi:9632547. The AAV1 genome shows more than 80% identity with other known AAV and contains the characteristic structural features. There is approximately 80% homology in the nucleotide sequence between AAV1 and AAV2. The ITRs of AAV1 are predicted to form T-shaped hairpin structures. The right and left ITRs of AAV1 are identical and virtually the same as the right ITR of AAV6, except for 1 nucleotide in the A and A' sequences and the last nucleotide in the D sequence. The AAV2 Rep binding motif found in the AAV2 preintegration region in human chromosome 19 is well conserved in AAV1. The terminal repeats of AAV1 are 143 nucleotides long, while those of AAV2, AAV3, and AAV4 are 145 or 146 nucleotides long. The p5 promoter region of AAV1 shows some divergence from homologous regions of other AAV serotypes but maintains critical regulatory elements; the repeated YY1 sites are present throughout all known AAV serotypes, including AAV1. The p19 promoter, the p40 promoter, and poly(A) can also be identified in the AAV 1 genome by homology to those in known AAV serotypes, which are also highly conserved (See Xiao et al. (1999) *J Virol* 73:3994-4003).

Examples of a suitable transgene used in the recombinant vector of the invention include gene sequences for the disease or transgene that confers a therapeutic effect to diseases such as amyloid polyneuropathy, Alzheimer's Disease, Duchenne's muscular dystrophy, ALS, Parkinson's Disease (e.g., glutamic acid decarboxylase gene for therapeutic effect) and brain tumors. The transgene may also be a selectable marker gene which is any gene sequence capable of expressing a protein whose presence permits selective propagation of a cell which contains it. Examples of selectable markers include gene sequence capable of conferring host resistance to antibiotics (such as ampicillin, tetracycline, kanamycin, etc.), amino acid analogs, or permitting growth of bacteria on additional carbon sources or under otherwise impermissible culturing conditions.

The skilled artisan can appreciate that regulatory sequences to control expression of the transgene can often be provided from commonly used promoters derived from viruses such as, polyoma, Adenovirus 2, lentivirus, retrovirus, and Simian Virus 40. Use of viral regulatory elements to direct expression of the transgene can allow for high level constitutive expression of the protein in a variety of host cells. Ubiquitously expressing promoters can also be used include, for example, the early lentivirus, retrovirus, promoter Boshart et al. (1985) *Cell* 41:521-530, herpesvirus thymidine kinase (HSV-TK) promoter (McKnight et al. (1984) *Cell* 37: 253-262), β-actin promoters (e.g., the human e-actin promoter as described by Ng et al. (1985) *Mol. Cell Biol.* 5: 2720-2732) and colony stimulating factor-1 (CSF-1) promoter (Ladner et al., (1987) *EMBO J.* 6: 2693-2698).

Alternatively, the regulatory sequences can direct expression of the transgene preferentially in a particular cell type, i.e., tissue-specific regulatory elements can be used. Preferred promoters are those functional in the central nervous system. Particularly preferred promoters are Chicken beta Active (CBA), and neuron-specific elonase (NSE). The promoter can be any desired promoter, selected based on the level of expression required of the transgene operably linked to the promoter and the cell type in which the vector is used. The promoter may also be an AAV2 promoter selected from the group consisting of p5, p19 and p40. In a preferred embodiment, the promoter is an AAV2 p5 promoter.

The recombinant vectors can be packaged into a particle using a transgene flanked by the same parvovirus ITR sequences e.g., AAV2 ITR sequences. In another embodiment, the transgene can be flanked by inverted terminal repeat sequences from two different parvoviruses. For example, the 5' ITR can be derived from AAV2 and the 3' ITR can be derived from AAV5, as long as at least one ITR comprises a packaging sequence required to package the chimeric capsid. In one embodiment, the chimeric capsid is produced with one ITR sequence from a AAV2 and the second ITR from a parvovirus selected from the group consisting of AAV1, AAV2, AAV3, AAV4, AAV5, AAV6, and the like. In a preferred embodiment, the ITR sequences are from AAV2. In another embodiment, the transgene may also be flanked with an ITR sequence from a parvovirus and an ITR sequence from a virus. For example, the 5' ITR can be derived from AAV2 and the 3' ITR can be derived from an adenovirus as long as at least one ITR comprises a packaging sequence and functions as intended to package the virus.

The ITR sequences for AAV2 are described, for example by Kotin et al. (1994) *Human Gene Therapy* 5:793-801; Bems "Parvoviridae and their Replication" in Fundamental Virology, 2nd Edition, (B. N. Fields and D. M. Knipe, eds.) The skilled artisan will appreciate that AAV ITR's can be modified using standard molecular biology techniques. Accordingly, AAV ITRs used in the vectors of the invention need not have a wild-type nucleotide sequence, and may be altered, e.g., by the insertion, deletion or substitution of nucleotides. The ITR's flanking the transgene need not necessarily be identical or derived from the same AAV serotype or isolate, so long as the ITR's function as intended, i.e., to allow for excision and replication of the bounded nucleotide sequence of interest when AAV rep gene products are present in the cell. Modified ITR's have been generated and have been shown to function for their intended purpose. The modified terminal repeat sequences were competent for AAV DNA replication, encapsidation, infection, integration, and subsequent rescue from the chromosome when superinfected with Ad and wild-type AAV (See e.g., Xiao et al. (1997) *J Virol* 71:941-948, and U.S. Pat. No. 6,346,415).

Wild-type AAV ITRs provide a functional origin of replication (ori) and function in cis for AAV DNA replication and for rescue or excision from prokaryotic plasmids. An ITR comprises two regions, the hairpin (HP) region and the D sequence. The HP sequence comprises the terminal 125 nucleotides of the AAV2 ITR, while the D sequence comprises the adjoining 20 nucleotides. In addition, the terminal resolution site (trs) lies between the HP region and the D sequence. The HP region contains palindromic sequence elements in the order A, C', C, B', B, A', and thus can fold back on itself to form a T-shaped hairpin structure (Muzyczka, (1992) *Curr. Top. Microbiol. Immunol.* 158:97-129). The terminal HP structure is apparently used as a primer for initiation of viral DNA replication, converting the single-stranded genome into a double-stranded template with a covalently closed hairpin at one end (Bems and Bohenzky, (1987) *Adv. Vir. Res.* 32: 243-306; and Lusby et al., (1980) *J. Virol.* 34: 402409).

The D sequence, which is not involved in forming the T-shaped structure of the ITR, appears to play a crucial role in high-efficiency rescue, selective replication and encapsidation of the AAV genome (Wang et al., (1997) *J. Virol.* 71: 3077-3082). Analysis of several D sequence mutants has shown that, when the 10 nucleotides of the D sequence distal to the HP were removed, the AAV genome could undergo efficient rescue, replication and encapsidation. However, when the deletion was extended to 15 nucleotides, rescue, replication and packaging were severely compromised.

The trs lies at the junction of the D sequence and HP sequences. The trs appears to be specifically bound and cleaved by Rep78 and Rep68 (Im and Muzyczka, (1990), *Cell* 61: 447-457; Im and Muzyczka, (1992), *J. Virol.* 66: 1119-1128; Snyder et al., (1990) *Cell* 60: 105-113).

Not all of the ITR appears to be essential for its various functions. For example, the 10 nucleotides of the D sequence distal to the HP region can apparently be deleted without impairing rescue, replication and encapsidation. However, much of the terminal 125 nucleotides of the HP region appears to be needed for DNA replication and terminal resolution (Bohenzky et al., (1988) *Virology* 166:316-327).

The recombinant vector can be constructed by directly inserting the transgene into an AAV genome which has had the major AAV open reading frames ("ORFs") excised therefrom. Other portions of the AAV genome can also be deleted, as long as a sufficient portion of the ITRs remain to allow for replication and packaging functions. These constructs can be designed using techniques well known in the art. (See, e.g., Lebkowski et al. (1988) *Molec. Cell. Biol.* 8:3988-3996; Vincent et al. (1990) Vaccines 90 (Cold Spring Harbor Laboratory Press); Carter (1992) *Current Opinion in Biotechnology* 3:533-539; Muzyczka (1992) *Current Topics in Microbiol. and Immunol.* 158:97-129; Kotin (1994) *Human Gene Therapy* 5:793-801; Shelling et al. (1994) *Gene Therapy* 1:165-169; and Zhou et al. (1994) *J. Exp. Med.* 179:1867-1875).

Deletion or replacement of the AAV genome, e.g., the capsid region of the AAV2, results in an AAV2 nucleic acid which is incapable of encapsidating itself. The chimeric capsid proteins can be provided using a nucleic acid construct that encodes the chimeric capsid proteins. The chimeric capsid proteins are provided in one or more expression vector(s) which are introduced into a host cell along with the AAV2 nucleic acid.

Plasmid expression vectors can typically be designed and constructed such that they contain a transgene encoding a protein or a portion of a protein necessary for encapsidation of the recombinant AAV2 nucleic acid i.e., the chimeric capsid proteins, or capsids that modify the tropism of the vector. Generally, construction of such plasmids can be performed using standard methods, such as those described in Sambrook, J. et al. Molecular Cloning: A Laboratory Manual, 2nd edition (CSHL Press, Cold Spring Harbor, N.Y. 1989).

The conditions under which plasmid expression vectors are introduced into a host cell vary depending on certain factors. These factors include, for example, the size of the nucleic acid of the plasmid, the type of host cell, and the desired efficiency of transfection. There are several methods of introducing the recombinant nucleic acid into the host cells which are well-known and commonly employed by those of ordinary skill in the art. These transfection methods include, for example, calcium phosphate-mediated uptake of nucleic acids by a host cell and DEAE-dextran facilitated uptake of nucleic acid by a host cell. The methods that are most efficient in each case are typically determined empirically upon consideration of the above factors.

As with plasmid expression vectors, viral expression vectors can be designed and constructed such that they contain a foreign gene encoding a foreign protein or fragment thereof and the regulatory elements necessary for expressing the foreign protein. Examples of such viruses include retroviruses, adenoviruses and herpesvirus.

Vectors without the rep gene appear to replicate and integrate at random sites in the host cell genome, while expression of Rep proteins Rep 68 and Rep 78, can mediate genomic integration into a well-defined locus on human chromosome 19 (Kotin, et al., *Proc. Natl. Acad. Sci. USA* 87:2211-2215 (1990); Samulski, et al., (1991) *EMBO J* 10:3941-3950; Giraud, et al., (1994) *Proc. Natl. Acad. Sci. USA* 91:10039-10043; Weitzman et al., (1994) *Proc. Natl. Acad. Sci. USA* 91:5808-5812). The plasmid bearing the cap genes can encode a chimeric capsid comprising a cap gene from a parvovirus, e.g., AAV1, AAV2, AAV3, AAV4, AAV5 and AAV6, and the like, or a portion thereof, or a virus, e.g., herpesvirus, adenovirus, lentivirus, retrovirus, Epstein-Barr virus and vaccinia virus. Non-native cap genes can be derived from a parvovirus that is different from the wild type parvovirus. For example, by encapsulating a wildtype AAV vector with a capsid protein from an AAV that is different than the wild type AAV. In one embodiment, the wildtype AAV2 type vector is encapsulated with a capsid protein derived from an AAV1 type virus.

Suitable host cells for producing particles comprising the chimeric capsids or non-native capsids include, but are not limited to, microorganisms, yeast cells, insect cells, and mammalian cells, that can be, or have been, used as recipients of a exogenous nucleic acid molecule.

Cells from the stable human cell line, 293 (readily available through, e.g., the ATCC under Accession No. ATCC CRL1573) are preferred in the practice of the present invention. Particularly, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce virions.

The entry of viral expression vectors into host cells generally requires addition of the virus to the host cell media followed by an incubation period during which the virus enters the cell. Incubation conditions, such as the length of incubation and the temperature under which the incubation is carried out, vary depending on the type of host cell and the type of viral expression vector used. Determination of these parameters is well known to those having ordinary skill in the art. In most cases, the incubation conditions for the infection of cells with viruses typically involves the incubation of the virus in serum-free medium (minimal volume) with the tissue culture cells at 30° C. for a minimum of thirty minutes. For some viruses, such as retroviruses, a compound to facilitate the interaction of the virus with the host cell is added.

Recombinant AAV vectors can be packaged into particles by co-transfection of cells with a plasmid bearing the AAV replication and/or cap genes (e.g., chimeric cap genes or non-native cap genes). The replication and cap genes encode replication proteins or capsid proteins (e.g., chimeric capsids or non-native capsids), respectively and mediate replication and genomic integration of AAV sequence, as well as packaging and formation of AAV particles (Samulski (1993) *Current Opinion in Genetics and Development* 3:74-80; Muzyczka, (1992) *Curr. Top. Microbiol. Immunol.* 158:97-129).

Generally, AAV helper function vectors can be engineered using conventional recombinant techniques. Particularly, nucleic acid molecules can be readily assembled in any desired order by inserting one or more accessory function nucleotide sequences into a construct, such as by ligating restriction fragments or PCR-generated products into a cloning vector using polylinker oligonucleotides or the like. The newly formed nucleic acid molecule can then be excised from the vector and placed in an appropriate expression construct using restriction enzymes or other techniques that are well known in the art.

The AAV helper function vectors can be used in a variety of systems for recombinant AAV virion production. For example, suitable host cells that have been transfected with an AAV helper function vector are capable of producing recombinant AAV virions when co-transfected with an AAV vector. One or more accessory function vectors capable of being expressed in the cell may also be co-transfected to provide accessory functions. The AAV vector, AAV helper construct and the accessory function vector(s) can be introduced into the host cell, either simultaneously or serially, using transfection techniques described above.

The chimeric capsid or non-native capsid can also be produced in a suitable host cell and can be used as a delivery vehicle for an operatively linked transgene.

Standard methods of infectivity known to the skilled artisan can be used to test for the altered tropism (See e.g., Grimm et al. (1998) *Hum Gene Ther* 10: 2745-60). For example, efficiency of entry can be quantitated by introducing a recombinant vector with a chimeric capsid or non-native capsid into the wild type AAV vector and monitoring transduction as a function of multiplicity of infection (MOI). A reduced MOI of the recombinant vector comprising chimeric capsid, or recombinant pseudotyped vector comprising a non-native capsid, compared to a recombinant vector with a wild type capsid indicates a more efficient vector. For example, fewer AAV5 particles than AAV2 are required to get transduction into a cell in a target organ, e.g., brain.

Examples of attachment sites present on a surface cell types that can be targeted by the recombinant vector with the chimeric capsid or a recombinant pseudotyped vector with native capsid include, but are not limited to heparin and chondroitin sulfate moities found on glycosaminoglycans, sialic acid moieties found on mucins, glycoproteins, gangliosides, MHC class I glycoproteins, common carbohydrate components found in the cell membrane glycoproteins including mannose, N-acetyl-galactosamine, N-acetyl-glucosacmine, fucose, galactose and the like. Particularly preferred attachments sites are those present on neural cells.

II Recombinant Pseudotyped Vectors

In one aspect the invention features recombinant pseudotyped vectors comprising a non-native capsid that is derived form a parvovirus other than the wild type parvovirus. In a preferred embodiment, the recombinant pseudotyped parvovirus are recombinant pseudotyped AAV virion vectors. The recombinant pseudotyped adeno-associated virion comprises a transgene flanked 5' and 3' by inverted terminal repeat sequences that can be derived from a first adeno-associated virus, where the first adeno-associated virus is a wild type adeno-associated virus. The transgene is encapsulated in a non-native capsid derived from a second adeno-associated virus that is different from the first adeno-associated virus, such that the transgene is packaged within the non-native capsid. Once packaged, the non-native capsid provides a modified tropism and can bind to an attachment site present on a cell surface in the central nervous system of a subject with a higher affinity than a corresponding adeno-associated virion with a wild type capsid. Upon entry into the cell the transduction rate of the pseudotyped virion is at least about 2 fold to about 100 fold higher than the corresponding wild type virion, preferably about 3-fold, 4-fold, 5-fold, 6-fold, 7-fold, 8-fold, 9-fold, 10-fold, 11-fold, 12-fold, 13-fold, 14-fold, 15-fold, 20-fold, 30-fold, 40-fold, 50-fold, 60-fold, 70-fold, 80-fold, 90-fold, and 100-fold higher than the corresponding wild type virion.

With the recombinant pseudotyped vectors, the AAV capsid packages an AAV genome of a different AAV type. For example, a recombinant AAV1, AAV2, AAV3, AAV4, AAV5, AAV6 and the like type genome may be encapsidated within an AAV1, AAV2, AAV3, AAV4, AAV5, AAV6 capsid, provided that the AAV capsid and genome are of different types.

In particularly preferred embodiments, the recombinant pseudotyped AAV of vector has an AAV-2 genome encapsulated within an AAV1, AAV3, AAV4, AAV5, AAV6, and the like capsid. In particular preferred embodiment, the recombinant pseudotyped AAV vector comprises an AAV2 type genome encapsulated with an AAV1 capsid. In another embodiment, the recombinant pseudotyped AAV virions comprises an AAV2 type genome encapsulated with an AAV5 capsid.

The recombinant pseudotyped vectors can be prepared by using the same methodology described above using the pseudotyped helper functions. The pseudotyped AAV helper function vectors can be engineered using conventional recombinant techniques. These pseudotyped AAV helper functions comprise a capsid region that can be derived from any AAV serotype that is different from the wild type AAV. The cap coding region can be derived from AAV serotypes that include, but are not limited to, AAV1, AAV2, AAV3, AAV4, AAV5, AAV6, and the like. In one embodiment, the entire capsid region of the wild type AAV vector is replaced with the entire capsid region of a different AAV vector. In another embodiment, the entire capsid region of a different AAV vector can be altered by mutations (point, additions, substitutions). Other natural variants of the capsid region are also within the scope of the invention. Preferred capsids are derived from the AAV 1, or the AAV5 serotype.

The pseudotyped AAV helper function vectors also comprise a rep coding region. The rep coding region can be derived from any AAV serotypes that include, but are not limited to, AAV1, AAV2, AAV3, AAV4, AAV5, AAV6, and the like, as long as it functions for its intended purpose. In one embodiment, the rep coding region is derived from the wild type AAV vector. For example, if the wild type AAV is AAV2, then the rep coding region can be derived from AAV2. In another embodiment, the rep coding region is derived from a AAV vector that is different from the wild type AAV. Examples of pseudotyped helper constructs are described in detail in Example 1 and shown in FIG. 1.

The pseudotyped AAV helper function vectors can be used in a variety of systems for recombinant pseudotyped AAV virion production. For example, suitable host cells that have been transfected with a pseudotyped AAV helper function vector are capable of producing recombinant pseudotyped AAV virions when cotransfected with an AAV vector comprising a transgene or transgene expression cassette. One or more accessory function vectors capable of being expressed in the cell may also be cotransfected to provide accessory functions. The AAV vector comprising a transgene or transgene expression cassette, the pseudotyped AAV helper construct and the accessory function vector(s) can be introduced into the host cell, either simultaneously or serially, using transfection techniques described above.

Suitable host cells for producing particles comprising the pseudotyped AAV helper constructs include, but are not limited to, microorganisms, yeast cells, insect cells, and mammalian cells, that can be, or have been, used as recipients of a exogenous nucleic acid molecule. Cells from the stable human cell line, 293 (readily available through, e.g., the ATCC under Accession No. ATCC CRL1573) are preferred in the practice of the present invention. Particularly, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce virions. Example 2 describes how to produce recombinant pseudotyped virions by cotransfection into 293 kidney cells.

Standard methods of infectivity known to the skilled artisan can be used to test for the alter tropism (See e.g., Grimm et al. (1998) *Hum Gene Ther* 10: 2745-60). For example, efficiency of entry can be quantitated by introducing a recombinant pseudo typed into a cell and monitoring transduction as a function of multiplicity of infection (MOI). A reduced MOI of the recombinant pseudotyped vector comprising a non-native capsid, compared to a recombinant vector with a wild type capsid indicates a more efficient vector. For example, fewer AAV1-AAV2 particles are required than wild type AAV2, to get transduction into a cell in a target organ, e.g., brain.

The Examples show that infectious recombinant pseudotyped vectors can be produced using the pseudotyped helper constructs of the invention. The yields of the different serotypes are shown in the FIG. 2. The yield of pseudotyped AAV1-AAV2 was about 5 to 10 times higher than the yield of AAV2-AAV2 (wild type). These higher yields are important particularly when the vectors are to be delivered to the central nervous system, e.g., regions of the brain. Due to the high yields of genomic particles which makes the vectors highly concentrated, the pseudotyped vector can be delivered to the central nervous system, e.g., a region of the brain, in smaller volume of a suitable carrier.

The pseudotyped vectors also transfected different regions of the brain, such as the as the stratium and hippocampus. The transduction results demonstrate that the AAV1-AAV2 pseudotype vector transduced almost all the hippocampus area and stratium. The AAV1-AAV2 pseudotyped vector diffused a greater distance from the injection site than the wild type vector, and transduces a more extensive cell number and volume in the central nervous system, than the other pseuodotyped vectors.

The pseudotyped AAV vectors of the invention can be used to escape pre-existing immune responses in a subject. For example, the AAV1-AAV2 pseudotyped vector containing the AAV1 capsid can be used is to escape the pre-existing immune responses to the AAV2 vector. The AAV1-AAV2 pseudotyped vector can be used in the patients who already has AAV2 neutralizing antibodies by natural infection or by previous administration of AAV2 vectors. The pseudotyped vectors of the invention can also be co-administration with one or more other pseudotyped vectors. For example, if two or more genes are required to be transduced into same cells, separating one gene from the other and placing them in different pseudotyped vectors, may increase the co-transduction rate because each pseudotyped vector uses a different receptor to bind to, and enter the cell.

III Recombinant Vectors Comprising Chimeric Capsids

The invention also features a method of producing recombinant vectors comprising a chimeric capsid. Recombinant vectors can be constructed using known techniques to provide operatively linked components of control elements including a transcriptional initiation region, a transgene, and a transcriptional termination region, as described above.

The recombinant viral vectors comprising a chimeric capsid have at least one non-native amino acid sequence, where the non-native amino acid sequence is derived from a capsid protein domain of a parvovirus, a virus, or a combination thereof, and where the chimeric capsid is capable of binding to an attachment site present on a cell surface of a neural cell; and a transgene flanked 5' and 3' by inverted terminal repeat sequences. The inverted terminal repeat sequences can be derived from a parvovirus, a virus, or a combination thereof, as long as at least one inverted terminal repeat sequence comprises a packaging signal that allows assembly of the chimeric capsid.

In one embodiment, the invention features a recombinant AAV2 vector comprising a chimeric capsid having at least one native AAV2 amino acid sequence and at least one non-native amino acid sequence derived from a parvovirus other than AAV2, wherein the chimeric capsid is capable of binding to an attachment site present on a cell surface; and a transgene flanked 5' and 3' by a first inverted terminal repeat sequences derived from AAV2 and a second inverted terminal repeat sequence derived from a parvovirus.

The chimeric capsids can be constructed in which the capsid region comprising the capsid viral protein subunits, VP1, VP2 and VP3 of a first AAV, can be replaced entirely with the VP1, VP2 and VP3 subunits of a second AAV. Alternatively, the chimeric capsid can be constructed so that a portion of a capsid subunits can be replaced. The nucleotide sequences for the various AAV serotypes are available from Genbank using the accession numbers provided above, as well as from a number of references such as Chiorini et al. (1999) *J. Virol.* 73: 1309-1319; Xiao et al. (1999) *J. Virol.* 73: 3994-4003 and Rutledge et al. (1998) *J. Virol.* 72: 309-319.

The entire capsid region of the AAV, or the individual VP regions, can be generated using standard molecular biology techniques such as PCR amplification, as described, for example, Sambrook J., Fritsch E. F., Maniatis T.: Molecular cloning: a laboratory manual. Cold Spring Harbor, N.Y., Cold Spring Harbor Laboratory, 1989) and the Examples section.

The entire capsid coding region (i.e. VP1, VP2, and VP3) for AAV1 spans from nucleotide positions 2222 (ATG) through 4433 (TAA) of SEQ ID NO: 1. More specifically, the VP1 region begins at nucleotide position 2222 (ATG) and ends at nucleotide position 2827. The VP2 region begins at nucleotide position 2828 (ACG) and ends at nucleotide position 2806. The VP3 region begins at nucleotide position 2807 (ATG) and ends at nucleotide position 4410.

The entire capsid coding region (i.e. VP1, VP2, and VP3) for AAV2 spans from nucleotide positions 2203 (ATG) through 4410 (TAA) of SEQ ID NO: 2. More specifically, the VP1 region begins at nucleotide position 2203 (ATG) and ends at nucleotide position 2613. The VP2 region begins at nucleotide position 2614 (ACG) and ends at nucleotide position 2808. The VP3 region begins at nucleotide position 2809 (ATG) and ends at nucleotide position 4410.

The entire capsid coding region (i.e. VP1, VP2, and VP3) for AAV3 spans from nucleotide positions 2209 (ATG) through 4410 (TAA) of SEQ ID NO: 3. More specifically, the VP1 region begins at nucleotide position 2209 (ATG) and ends at nucleotide position 2619. The VP2 region begins at nucleotide position 2620 (ACG) and ends at nucleotide position 2814. The VP3 region begins at nucleotide position 2815 (ATG) and ends at nucleotide position 4419.

The entire capsid coding region (i.e. VP1, VP2, and VP3) for AAV4 spans from nucleotide positions 2260 (ATG) through 4464 (TAA) of SEQ ID NO: 4. More specifically, the VP1 region begins at nucleotide position 2260 (ATG) and ends at nucleotide position 2667. The VP2 region begins at nucleotide position 2668 (ACG) and ends at nucleotide position 2853. The VP3 region begins at nucleotide position 2854 (ATG) and ends at nucleotide position 4464.

The entire capsid coding region (i.e. VP1, VP2, and VP3) for AAV5 spans from nucleotide positions 2207 (ATG) through 4381 (TAA) of SEQ ID NO: 5. More specifically, the VP1 region begins at nucleotide position 2207 (ATG) and ends at nucleotide position 2614. The VP2 region begins at nucleotide position 2615 (ACG) and ends at nucleotide position 2782. The VP3 region begins at nucleotide position 2783 (ATG) and ends at nucleotide position 4381.

The entire capsid coding region (i.e. VP1, VP2, and VP3) for AAV6 spans from nucleotide positions 2208 (ATG) through 4418 (TAA) of SEQ ID NO: 6. More specifically, the VP1 region begins at nucleotide position 2208 (ATG) and ends at nucleotide position 2618. The VP2 region begins at nucleotide position 2619 (ACG) and ends at nucleotide position 2813. The VP3 region begins at nucleotide position 2814 (ATG) and ends at nucleotide position 4418.

In one embodiment, the chimeric capsids of the recombinant vectors are produced by "complete substitutions", this term as used herein refers to replacing the entire capsid viral protein domain of the host with a non-native amino acid sequence. For example, a recombinant AAV2 vector in which the amino acid sequence of the VP1 domain of AAV2 is retained, but the entire amino acid sequence of the VP2 and VP3 domain of AAV2 is replaced with the entire amino acid sequence of the VP2 domain from another parvovirus, such as AAV5.

In another embodiment, the chimeric capsids of the recombinant vectors are produced by "patch substitution" this term as used herein refers to replacing a fragment of the capsid viral protein domain of the host with a fragment of non-native amino acid sequence from another parvovirus. For example, a recombinant AAV2 vector in which a fragment of the amino acid sequence of the VP1 domain of AAV2 is replaced with a corresponding fragment of a non-native amino acid sequence from AAV5. The non-native amino acid sequence preferably comprises a determinant that alters the tropism of the capsid. The altered tropism can allow the chimeric capsid to bind to an attachment site on cell surface with a higher affinity than a wild type capsid. The modified tropism of the chimeric capsid allows a wider range of host cells to be targeted. The infective properties of such a particle can be improved above those of a recombinant vector containing a wild type capsid. Alternatively, the altered tropism can prevent the chimeric capsid from binding to an attachment site on a cell surface. This provides for a method of selecting cell types for specific targeting of a transgene, while excluding expression of the transgene where it is not wanted. Other embodiments include mutations (single amino acid substitution or deletion mutations) within the capsid viral protein domain that alter the tropism.

In one embodiment, the invention features recombinant vectors with a chimeric capsid where the chimeric capsid comprises fragments of the entire AAV2 capsid protein, VP1, VP2, or VP3 sequences. The fragments can be an amino acid sequence comprising about 10 amino acids, more preferably about 20, 30, 40, 50, 60, 70, 80, 90, 100, 120, 140, 160, 180 and 200 or more amino acids in length.

Additionally, modifications can be made to the nucleic acid molecule encoding the capsid protein or fragment thereof, such that modifications to the nucleotide sequences that encode a capsid protein produce a capsid protein with a modified amino acid sequence. Such means of generating modification to a sequence are standard in the art (See e.g., Sambrook J., Fritsch E. F., Maniatis T.: Molecular cloning: a laboratory manual. Cold Spring Harbor, N.Y., Cold Spring Harbor Laboratory, 1989) and can be performed.

Also within the scope of the invention are AAV2 recombinant vectors with a chimeric capsid comprising VP1, VP2, VP3 proteins that can have at least 60% homology to the polypeptide encoded by nucleotides at position 2202 to nucleotide at position 4412 of AAV2 (Genbank accession no. gi:9626146). The capsid protein can have about 70% homology, about 75% homology, about 80% homology, about 85% homology, about 90% homology, about 95% homology, about 99% homology to the polypeptide encoded by nucleotides at position 2202 to nucleotide at position 4412.

In another aspect, the invention features a recombinant pseudotyped parvovirus vector that comprises a wild type parvovirus genome, and a non-native capsid derived from a parvovirus that is different from the wild type parvovirus. In one embodiment, the recombinant pseudotyped parvovirus vector is a recombinant pseudotyped AAV vector.

It is also preferred that the wild type AAV genome comprises one or more AAV inverted terminal repeat(s). Typically, a recombinant AAV genome will retain only those elements required in cis (e.g., one or more AAV ITRs), with the rest of the genome (e.g., the rep/cap genes) being provided in trans.

In another embodiment, the recombinant vector of the invention can be a vector comprising a chimeric capsid containing amino acid sequences from a parvovirus, and a non-native amino acid sequence from a virus that can be used to target a neural cell. Examples of a suitable virus include, but are not limited to, AAV1, AAV2, AAV3, AAV4, AAV5, and AAV6. Examples of a suitable virus include, but are not limited to, herpesvirus, adenovirus, lentivirus, retrovirus, Epstein-Barr virus and vaccinia virus. The recombinant vector with a chimeric capsid can have an altered tropism that allows the capsid coat to bind to the surface of cell types with a higher affinity than a recombinant vector with a wild type capsid. Alternatively, the modified tropism prevents the capsid from targeting particular cell types.

The skilled artisan can appreciate there are numerous viruses that can comprise capsid proteins which can be used to construct the recombinant vector with the chimeric capsid.

For example, the herpesviruses is a large double stranded DNA viruses consisting of an icosahedral capsid surrounded by an envelope. The group has been classified as alpha, beta and gamma herpesviruses on the basis of genome structure and biological properties (See e.g., Roizman. et al. (1981) *Int. virology* 16, 201-217). The herpes particle constitutes over 30 different proteins which are assembled within the host cell. About 6-8 are used in the capsid.

The herpes simplex virus 1 (HSV-1) genome specifies an abundant capsid protein complex which in denaturing gels forms multiple bands due to different molecular weights of the component proteins. Details of the HSV-1 capsid have been well documented, see for example, Davison et al. (1992) *J. Gen. Virol.* 73:2709-2713; Gibson et al. (1972) *J. Virol.* 10: 1044-1052; and Newcomb et al., (1991) *J. Virol.,* 65:613-620). Several herpesvirus sequences are available from GenBank.

The human adenovirus is comprised of a linear 36 kilobase double-stranded DNA genome, which is divided into 100 map units, each of which is 360 base pair in length. The DNA contains short inverted terminal repeats (ITR) at each end of the genome that are required for viral DNA replication. The gene products are organized into early (E1 through E4) and late (L1 through L5) regions, based on expression before or after the initiation of viral DNA synthesis (See, e.g., Horwitz, Virology, 2d edit., ed. B. N. Fields, Raven Press, Ltd. New York (1990)).

The adenovirus capsid has been well characterized and nucleic acid molecules of various adenoviruses are available in GenBank. Adenovirus interacts with eukaryotic cells by virtue of specific receptor recognition by domains in the knob portion of the fiber protein which protrude from each of the twelve vertices of the icosahedral capsid (See e.g., Henry et al. (1994) *J. Virol.* 68:5239-5246; Stevenson et al. (1995) *J. Virol.* 69:2850-2857; and Louis et al. (1994) *J. Virol.* 68:4104-4106). These or other regions of the adenovirus capsid may be used to construct the chimeric capsid of the invention. Nucleic acid sequences of many lentivirus, retrovirus types are available from GenBank.

IV Administration of Recombinant Vectors

Administration of the recombinant vectors of the invention (i.e., recombinant vectors comprising a chimeric capsid or recombinant pseudotyped vectors comprising a non-native capsid) to a cell (e.g., a neural cell) can be accomplished by standard methods in the art. Preferably, the vector is packaged into a particle and the particle is added to the cells at the appropriate multiplicity of infection. The modified tropism of the recombinant vector allows the capsid to interact with an attachment site on a cell surface of a neural cell that a wild type capsid fails to interact with, for example, the AAV2 has a poor tropism for human myeloid stem cells. However, a recombinant vector with a chimeric capsid comprising non-native capsid proteins from different member of the parvovirus family, or the recombinant pseudotyped vectors may confer the ability to AAV2 to interact with human myeloid stem cells. Alternatively, the modified tropism can prevent the capsid from interacting with a particular cell type, to thereby selectively target desired cell types.

Administration of the recombinant vectors of the invention to the cell can be by any means, including contacting the recombinant vector with the cell. For such in vitro method, the vector can be administered to the cell by standard transduction methods. (See e.g., Sambrook, Supra.) The cells being transduced can be derived from a human, and other mammals such as primates, horse, sheep, goat, pig, dog, rat, and mouse. Cell types and tissues that can be targeted include, but are not limited to, adipocytes, adenocyte, adrenal cortex, amnion, aorta, ascites, astrocytes, bladder, bone, bone marrow, brain, breast, bronchus, cells of the central nervous system (CNS), cardiac muscle, cecum, cervix, chorion, colon, conjunctiva, connective tissue, cornea, dermis, duodenum, endometrium, endothelium, epithelial tissue, epidermis, ependymal, esophagus, eye, fascia, fibroblasts, foreskin, gastric, glial cells, glioblast, gonad, hepatic cells, histocyte, ileum, intestine, small intestine, jejumim, keratinocytes, kidney, larynx, leukocytes, lipocyte, liver, lung, lymph node, lymphoblast, lymphocytes, macrophages, mammary alveolar nodule, mammary gland, mastocyte, maxilla, melanocytes, monocytes, mouth, microglia, myelin, nervous tissue, neural cells, neuroblast, neurons, neuroglia, oligodendrocytes, osteoblasts, osteogenic cells, ovary, palate, pancreas, papilloma, cells of the peripheral nervous system, peritoneum, pituicytes, pharynx, placenta, plasma cells, pleura, prostate, rectum, salivary gland, skeletal muscle, skin, smooth muscle, somatic, spleen, squamous, stomach, submandibular gland, submaxillary gland, synoviocytes, testis, thymus, thyroid, trabeculae, trachea, turbinate, umbilical cord, ureter, and uterus. In a preferred embodiment, the cells are neural cells.

The recombinant vectors of the invention can be incorporated into pharmaceutical compositions suitable for administration to a subject. Typically, the pharmaceutical composition comprises the recombinant vectors of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The recombinant vectors of the invention can be incorporated into a pharmaceutical composition suitable for parenteral administration. Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antigen, antibody or antibody portion) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The pharmaceutical compositions of the invention may include a "therapeutically effective amount" or a "prophylactically effective amount" of the recombinant vector. A "therapeutically effective amount" refers to an amount effective, at dosages and for periods of time necessary, to achieve the desired therapeutic result. A therapeutically effective amount of the recombinant vector may vary according to factors such as the disease state, age, sex, and weight of the individual and the ability of the vector to elicit a desired response in the individual. A therapeutically effective amount is also one in which any toxic or detrimental effects of the recombinant vector is outweighed by the therapeutically beneficial effects. A "prophylactically effective amount" refers to an amount effective, at dosages and for periods of time necessary, to achieve the desired prophylactic result.

For in vitro administration of the vectors of the invention into a neural cells, standard procedures such as transduction can be performed. (See e.g., Sambrook, id.). For in vivo administration of the vectors of the invention, broad distribution of the vectors into the CNS can be accomplished by injecting the vector into the cerebrospinal fluid, e.g., by lumbar puncture (See e.g., Kapadia et al. (1996) *Neurosurg* 10: 585-587). Alternatively, precise delivery of the vector into specific sites of the brain to target a neural cell, can be conducted using stereotactic microinjection techniques. For example, the subject being treated can be placed within a stereotactic frame base (MRI-compatible) and then imaged using high resolution MRI to determine the three-dimensional positioning of the particular region to be treated. The MRI images can then be transferred to a computer having the appropriate stereotactic software, and a number of images are used to determine a target site and trajectory for antibody microinjection. The software translates the trajectory into three-dimensional coordinates that are precisely registered for the stereotactic frame. In the case of intracranial delivery, the skull will be exposed, burr holes will be drilled above the entry site, and the stereotactic apparatus used to position the needle and ensure implantation at a predetermined depth. The vector can be delivered to regions, such as the cells of the stratium, hippocampus, spinal cord, brainstem, (medulla, pons, and midbrain), cerebellum, diencephalon (thalamus, hypothalamus), telencephalon (corpus stratium, cerebral cortex, or within the cortex, the occipital, temporal, parietal or frontal lobes), or combinations, thereof. In another preferred embodiment, the vector is delivered using other delivery methods suitable for localized delivery, such as localized permeation of the blood-brain barrier. Particularly preferred delivery methods are those that deliver the vector to regions of the brain that require modification.

Modification as used herein refers to a change in the cellular activity in the region of the brain injected with the vector. The change in cellular activity can result from changing the expression, or production of genes responsible for stimulating, activating, or inhibiting, a cell. For example, delivery of a vector comprising a nucleotide sequence encoding GAD, to a region of the brain that is overstimulated, such as the basal ganglia. In particular, delivery of the vector to the STN which are overactive in diseases such as Parkinson's, will result in expression of GAD in this region.

V. Therapeutic Uses of Recombinant Vectors

The recombinant vectors with the chimeric capsids, or the recombinant pseudotyped vectors of the invention offer the advantage over current vector systems for delivery into cells, in particular into neural cells. Due to their modified tropism, the recombinant vectors can efficiently and safely deliver transgenes to cells that are not normally targeted by vectors with a wild type capsid. The recombinant vectors of the invention may also be used to selectively target desired cell types, while excluded of the cell types based on the modified tropism. The pseudotyped vectors of the invention are particularly suitable for delivering transgenes to cells of the central nervous system. In particular to the brain or different regions of the brain.

The recombinant vector with a chimeric capsid, or the recombinant pseudotyped vectors can comprise a transgene sequence that is associated with a disease or a disorder such that expression of the transgene would result in amelioration of the disease or disorder. There are a number of neurological and neurodegenerative diseases that can benefit from such a therapy, which include, but are not limited to, Parkinson's disease, Huntington disease, Alzheimer disease, ALS, epilepsy, stroke and central nervous system tumors. These include astrocytomas, oligodendrogliomas, meningiomas, neurofibromas, ependymomas, Schwannomas, neurofibrosarcomas, glioblastomas, and the like.

The term "neurodegenerative disorder" "neurological disorder" as used herein refers to a disorder which causes morphological and/or functional abnormality of a neural cell or a population of neural cells. The neurodegenerative disorder can result in an impairment or absence of a normal neurological function or presence of an abnormal neurological function in a subject. For example, neurodegenerative disorders can be the result of disease, injury, and/or aging. Non-limiting examples of morphological and functional abnormalities include physical deterioration and/or death of neural cells, abnormal growth patterns of neural cells, abnormalities in the physical connection between neural cells, under- or over production of a substance or substances, e.g., a neurotransmitter, by neural cells, failure of neural cells to produce a substance or substances which it normally produces, production of substances, e.g., neurotransmitters, and/or transmission of electrical impulses in abnormal patterns or at abnormal times. Neurodegeneration can occur in any area of the brain of a subject and is seen with many disorders including, for example, head trauma, stroke, ALS, multiple sclerosis, Huntington's disease, Parkinson's disease, and Alzheimer's disease.

The recombinant vectors of the invention are particularly useful for diseases such as Parkinson's disease which is associated with a disturbances of posture, locomotion, facial expression or speech. Symptoms of Parkinson's disease are caused by loss of nerve cells in the pigmented substantia nigra pars compacta (SNPC) and the locus coeruleus in the midbrain. The stratium or corpus stratium is a structure in the cerebral hemispheres consisting of two basal ganglia (the caudate nucleus and the putnam) and the fibre of the internal capsule that separate them. Parkinson's disease in humans primarily effects the subcortical structures, especially the substantai nigra and the locus ceruleus. It is characterized by the loss of dopamine neurons in the substanta nigra, which have the basal ganglia as their major target organ. Cell loss also occurs in the globus pallidus and putamen.

Parkinson's disease is also associated with eosinophilic intraneural inclusion granules (Lewy bodies) which are present in the basal ganglia, brainstem, spinal cord, and sympathetic ganglia. The pars compacta neurons of the substantia nigra (SN) provide dopaminergic input into the stratium, which is part of the basal ganglia. These dopaminergic neurons modulate a monosynaptic gamma-aminobutyric acid (GABA) inhibitory output in the globus pallidus interna and pars reticulata of the substantia nigra. In Parkinson's disease, loss of dopaminergic cells in the substantia nigra leads to stratial dopamine depletion. This loss of dopamine alters the activity of neurons within the basal ganglia circuitry, including excessive firing and activity of these cells. Accordingly, the recombinant vectors of the invention can be used to deliver a therapeutic gene to the site of domaminergic cell loss or other regions of the basal ganglia and output nuclei.

Several animal models of Parkinson's disease have been generated in which effective therapies are indicative of therapeutic efficacy in humans. These animal models include three rat models (the rats having lesions in substantia nigral dopaminergic cells caused by treatment with 6-hydroxydopamine, 1-methyl-4-phenyl-1,2,3,6-tetrahydropyridine (MPTP), or surgical transection of the nigral striatal pathway) (See, e.g. Björklund et al. (1982) *Nature* 298:652-654), a rhesus monkey model (the monkeys having lesions in substantia nigral dopaminergic cells caused by treatment with MPTP) (See, e.g., Smith, et al. (1993) *Neuroscience* 52):7-16; Bakay et al. (1985) *Appl. Neurophysiol.* 48:358-361; Zamir. et al. (1984) *Brain Res.* 322:356-360), and a sheep model (the sheep having lesions in substantia nigral dopaminergic cells caused by treatment with MPTP) (Baskin, et al. (1994) *Life Sci.* 54:471-479). In another embodiment, the antigen, antibody or antibody portion of the invention can be used to treat a subject with Parkinson's disease. To assess therapeutic strategies, morphological and immunohistochemical studies can be performed by conventional techniques and behavioral tests can also be performed to determine the efficacy of the therapy, such as the Barnes Circular Maze test, or the lisne crossing mobility test, as described previously (Barnes et al. (1979) *J. Comp. Physiol. Psychol.* 93: 74-104; and (Carlsson et al. (1990) *Life Sci.* 47: 1729).

The recombinant vectors of the invention can also be used to ameliorate the symptoms of Huntington's disease. Models of Huntington's diseases have been developed in several different animals. For example, rat (Isacson et al. (1985) *Neuroscience* 16:799-817), monkey (Kanazawa, et al. (1986) Neurosci. Lett. 71:241-246), and baboon (Hantraye. et al. (1992) *Proc. Natl. Acad. Sci. USA* 89:4187-4191; Hantraye, et al. (1990) *Exp. Neurol.* 108:91-014; Isacson, et al.(1989) *Exp. Brain Res.* 75(1):213-220). Neurodegeneration in Huntington's disease typically involves degeneration in one or both nuclei forming the stratium or corpus stratium, the caudate nucleus and putamen. To assess therapeutic strategies, morphological and immunohistochemical studies can be performed by conventional techniques and behavioral tests can also be performed to determine the efficacy of the therapy, such as the Barnes Circular Maze test, or the lisne crossing mobility test, as described previously (Barnes et al. (1979) *J. Comp. Physiol. Psychol.* 93: 74-104; and (Carlsson et al. (1990) *Life Sci.* 47: 1729).

The recombinant vectors of the invention can also be used to ameliorate the symptoms of Amyloid Lateral Sclerosis (ALS). Several models of ALS are available. Mutations in the superoxide dismutase gene 1 (SOD-1) are found in patients with familial amyotrophic lateral sclerosis (FALS). Overexpression of a mutated human SOD-1 gene in mice results in neurodegenerative disease as result of motor neuron loss in lumbar spinal cord, providing a suitable model for FALS (See e.g., Mohajeri et al. (1998) *Exp Neurol* 150:329-336). Transgenic models of ALS are also described (See e.g., Gurney (1997) *J Neurol Sci* 152:S67-73). Expression of mutant SOD1 genes in transgenic mice causes a progressive paralytic disease whose general features resemble ALS in humans. These models can be used to examine the effect of an antigen, antibody or antibody portion that can be used to modify the function of receptors or transporter proteins associated with ALS (e.g., EAAT2 transporter protein). A gain-of-function in these models can monitored, for example, improvement in motor impairments of the animal's limbs.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

EXAMPLES

Example 1

Construction of Pseudotyped Adeno-Associated Helper Plasmids

The pseudotyped adeno-associated helper plasmids for AAV1 and AAV5 are shown in FIG. 1. These pseudotyped helper plasmids were constructed using an AAV2 helper plasmid, referred to as p5E18 (Xiao, et al (1998). *J. Virol.* 72:10222-10226 & Xiao, et al, (1999) *J. Virol.* 73:3994-4003), as the backbone, and replacing its AAV2 capsid gene with either an AAV1 or AAV5 capsid gene. The primer nucleotide sequences used to generate the psueodtyped AAV vectors are based on AAV1 (Genbank accession no:gi:9632547), AAV2 (Genbank accession no: gi:9626146), and AAV5 (Genbank accession no: gi:4249656).

The AAV2 rep region (partial) was amplified using forward primer 5'-CGAGTCAGTTGCGCAGCCATCGACGTCAGA-3' (SEQ ID NO: 7) which corresponded with nucleotide positions 1847-1876 in the AAV2 genome and reverse primer 5'-CTGGAAGATAACCATCGGCAGCCATACCTGATTTAAATCATTTATTGTTC-3' (SEQ ID NO: 8) which correspond with nucleotide positions 2178-2202 in AAV2 genome using plasmid P5E18 as template. The 5' 25 nucleotides of the reverse primer (SEQ ID NO. 8) corresponded with the AAV1 genome at positions 2223-2247.

The AAV1 capsid gene was amplified using primers that corresponded with nucleotide positions 2223-2247 in AAV 1 genome using forward primer 5'-GAACAATAAATGATTTAAATCAGGTATGGCTGCCGATGGTTATCTTCCAG-3'

(SEQ ID NO: 9) and nucleotide positions 4550-4579 using the reverse primer 5'GGACTCTAGAGTAACCCGATGACGTAAGTCTTTTATCGCG-3' (SEQ ID NO: 10).

The subsequent PCR products were linked together by PCR amplification using the rep forward primer (SEQ ID NO: 7) and the cap reverse primer (SEQ ID NO: 10). After the PCR reaction, the PCR product was digested with HindIII and XbaI and the fragment subcloned into into p5E18 at the HindIII and XbaI cloning sites as described by Xiao et al. (1999) *J. Virol.* 73:3994-4003. The resulting plasmid is designated pHyb2t, a recombinant pseudotyped adeno-associated virus with an AAV1 capsid and AAV2 rep sequences, and is shown in SEQ ID NO: 11.

The same procedure was used to generate a recombinant pseudotyped adeno-associated virus with an AAV5 capsid and AAV2 rep sequences. The AAV2 rep region was amplified using primers that corresponded with nucleotide positions 1847-1876 in AAV2 genome with forward primer 5'-CGAGTCAGTTGCGCAGCCATCGACGTCAGA-3' (SEQ ID NO: 7) and nucleotide positions 2178-2202 in AAV2 genome with reverse primer 5'-CTGGAGGGTGATCAACAAAAGACATACCTGATTTAAATCATTTATTGTTC-3' (SEQ ID NO: 8) to amplify the rep sequence using plasmid P5E18 as template (The 5' 25 nucleotides of this primer corresponded with positions 2207-2231 of AAV5 genome) The AAV5 capsid gene was amplified using primers that corresponded with nucleotide positions 2207-2231 in AAV5 genome using forward primer 5'-GAACAATAAATGATTTAAATCAGGTATGTCTTTTGTTGATCACCCTCCAG-3' (SEQ ID NO: 12). The 5' 25 nucleotides of this primer corresponded with nucleotide positions 2178-2202 of AAV2 genome). The reverse primer corresponded with nucleotide positions 4419-4448 and has a sequence of 5'-GGACTCTAGAGACCACAAGAGGCAGTATTTTACTGACACG-3' (SEQ ID NO: 13).

The subsequent PCR products were linked together by PCR amplification using the rep forward primer (SEQ ID NO: 7) and the cap reverse primer (SEQ ID NO: 13). After the PCR reaction, the PCR product was digested with HindIII and XbaI and the fragment subcloned into pSE18 at the HindIII and XbaI cloning sites as described by Xiao et al. (1999) *J. Virol.* 73:3994-4003. The resulting plasmid is designated pHyb25, a recombinant pseudotyped adeno-associated virus with an AAV5 capsid and AAV2 rep sequences, and is shown in SEQ ID NO: 14. The helper plasmid with AAV-2 rep and AAV-2 capsid is shown in SEQ ID NO: 15.

Example 2

Construction of Pseudotyped Vectors

To test the packaging of the virus using the pseudotyped helper plasmids, expression cassettes containing detectable markers were generated. Enhanced green fluorecent protein (EGFP) and luciferase were used as markers. The CBA-EGFP-WPRE-BGH poly A vector was constructed by cloning the enhanced green fluorecent protein (EGFP) into an AAVs genome plasmid under the control of a chicken beta actin (CBA) promoter followed by a woodchuck post-regulatory element (WPRE), with a bovine growth hormone (bGH) polyadenylation site between the two AAV2 inverted terminal repeat sequences, as previously described (During et al. (1998) *Nature Med.* 4:1131-1135). The CBA-luciferase-WPRE-BGH poly A vector was constructed by cloning the luciferase gene into the AAV plasmid under the control of a chicken beta actin (CBA) promoter followed by a woodchuck post-regulatory element (WPRE), with a bovine growth hormone (bGH) polyadenylation site between the two AAV2 inverted terminal repeat sequences.

To determine whether the these expression cassettes could be packaged into recombinant virions using the pseudotyped helper plasmids, triple plasmid experiments were performed. Recombinant AAV EGFP or AAV luciferase viruses were generated by cotransfecting into 293 cells, the pseudotyped helper constructs described in Example 1, along with the CBA-EGFP-WPRE-BGH poly A and CBA-luciferase-WPRE-BGH poly A vectors described in Example 2, and an adeno helper plasmid at a ratio of 1:1:2, using calcium phosphate precipitation methods. Cells were incubated at 37° C. for 72-96 hours after transfection. After incubation, the cells were harvested and the viruses purified by double CsCl gradient. The viral titer was determined by Quantitative PCR.

Example 3

In-vitro Infectivity of the Pseudotyped Vectors

To test the in-vitro infectivity of the recombinant pseudotyped vectors, and to determine whether the AAV helpers supported recombinant AAV production, the pseudotyped helper constructs described in Example 1 were cotransfected into 293 cells, along with the CBA-EGFP-WPRE-BGH poly A and CBA-luciferase-WPRE-BGH poly A vectors described in Example 2, and an adeno helper plasmid at a ratio of 1:1:2, using calcium phosphate precipitation methods in a triple transfection. Cells were incubated at 37° C. for 72-96 hours post transfection. After incubation, the cells were harvested and the viruses purified by double CsCl gradient. The vector yield was determined by measuring the GFP and luciferase expression in 293 cells using cell lysate from the above preparation. At MOIs of 10-1000, robust expression was seen with the recombinant pseudotyped viruses.

The yields of the different serotypes are shown in the FIG. 2. From 15 dishes of 293 cell transfections (15 cm diameter), the yield for recombinant pseudotype AAV1-AAV2 was $1.17\times10^{13}$ genomic particles encoding luciferase and $5.06\times10^{12}$ genomic particles encoding EGFP. For the recombinant AAV2-AAV2 (wild type) virus, the yield was $5.60\times10^{11}$ genomic particles encoding luciferase and $1.03\times10^{12}$ genomic particles encoding EGFP. For recombinant pseudotype AAV5-AAV2, the yield was $1.80\times10^{12}$ genomic particles luciferase, and $1.62\times10^{12}$ genomic particles encoding EGFP. The results showed that the yield of AAV1-AAV2 was about 5 to 10 times higher than the yield of AAV2-AAV2 or AAV5-AAV2. These higher yields are important particularly when the vectors are to be delivered to the central nervous system, e.g., regions of the brain. Due to the high yields of genomic particles which makes the vectors highly concentrated, the pseudotyped vector can be delivered to the brain in smaller volume of a suitable carrier.

Example 4

In vivo Effect of the Pseudotyped Vector

To test the in vivo effect of the pseudotyped virions, the pseudotyped virions were prepared as described in Example 2, purified by CsCl gradient, and delivered to the brain. The pseudotyped vector were delivered specifically to the mid-stratium and hippocampus regions of the brain.

For delivery into the stratium, 3 μl ($1.5\times10^{10}$ genomic particles) of CBA-EGFP-WPRE-BGH vector plus 1.51 μl of mannitol were stereotaxically injected into the left mid-stratum of male Sprawl Dawley rats (275-325 g) (n=3) that had been anaesthetized with a mixture of Ketamine (67 mg/kg)/Xylazine (6.7 mg/kg) given interperitonially (ip). The experiment was not repeated with the CBA-luciferase-WPRE-BGH poly A vector.

For delivery into the hippocampus, 2 μl ($1\times10^{10}$ genomic particles) of each vector (recombinant CBA-EGFP-WPRE-BGH poly A or CBA-luciferase-WPRE-BGH poly A, packaged in AAV1, AAV2 or AAV5 capsids) plus 1 μl of mannitol were injected into the right hippocampus. The intracerebral infusion was administered at the rate of 0.2 μl/min. The needle was left in situ for additional 5 min before removal.

The brain tissue of the animals were examined using standard histology methods. Four weeks after in vivo administration of the pseudotyped vectors, the animals were perfused intracardially with phosphate buffered saline followed by 4% paraformaldehyde. The brain was removed and postfixed by 4% paraformaldehyde for about 4 hours and then transferred to 20% and 30% sucrose solution until the brain sank. The brain was cut coronally into 20 μm sections using a freezing cryostat (Leica, Germany). The section was then examined by fluorescent and confocal microscopy. Transgene expression was assessed by using stereology for cell counting. Individual brain slices (e.g., 50 brain slices) were examined to determine the region and number of cells that were transduced, the total number of cells from each slice was then added together from each one of the slides to provide a 3-dimensional configuration of the total area of the brain that had been transduced. The sum total number of transduced cells from each brain section was counted to provide an evaluation of the transduction rate for each of the recombinant pseudotyped vectors, or recombinant chimeric capsid vectors.

Under circumstances where sterological counting was impractical, for example where there is strong expression of the marker protein, fluorescent microscopic densitometry was used to determine the fluorescence intensity of marker protein in the target nuclei. The fluorescent images of each brain section were captured by a digital camera under the fluorescent microscope and the relative fluorescent intensity in the transduced nuclei of each image was analyzed by using the NIH image software. With densiometry analysis, color images of a marker protein were analyzed as a black and white images. The area that appeared as bright white indicated a region of the highest expression of the marker protein, a grey scale indicated a lower expression, and a black scale indicated no expression of the marker protein. The rate of transduction was determined by examining the area of "white" in a region of the brain. The greater the area of white in an image, the greater the expression of the marker protein in that region.

The transduction results of the difference pseudotyped vectors in different regions of the brain were by examining the fluorescence of GFP in the hippocampus (data not shown), four weeks after transduction. The data showed that in the hippocampus and in the hippocampus the AAV1-AAV2 pseudotype vector transduced almost all the hippocampus area. The neuron like cells in the CA1, CA2, CA3, dentate gyrus regions all strongly expressed GFP florescence, with the entire region turning green. Moreover, numerous fibers also turned green. This data demonstrates that the AAV1-AAV2 pseudotype vector transduced well in the brain, and transduced a greater number of cells further away from the needle tract than the other pseudotyped vectors. For the AAV2-AAV2 vector and AAV5-AAV2 pseudotyped vector, the transduced area was limited to the area near the needle tract. The AAV5-AAV2 pseudotyped vector showed more green fluorescence than the AAV2-AAV2 (wild type vector).

A similar result was observed in the stratium with the pseudotyped vectors. Again, in the striatum, more cells and fiber were transduced by the AAV1-AAV2 pseudotyped vector compared with other two stereotypes vectors. The AAV1-AAV2 pseudotyped vector also diffused further away from the needle tract, thereby transducing a greater number of cells which appeared green.

In order to quantitate the transduction difference of different pseudotyped vectors in the hippocampus, NIH imagine analysis was used to quantify the relative densitometry of the hippocampus, and the results depicted in FIG. 3. The results show that the GFP expression using the psuedotyped AAV 1-AAV2 vector was significantly stronger than the GFP expression observed with the AAV2-AAV2 and the AAV2-AAV5 pseudotyped vectors ($P<0.05$, one way ANOVA, post hoc). The data shows that based on densitometric analysis, the rate of transduction and expression of the AAV1-AAV2 pseudotyped vector is about 8-10 fold higher than the AAV2-AAV2 vector. The rate of transduction and expression of the AAV5-AAV2 pseudotyped vector is about 2-fold higher than the AAV2-AAV2 vector.

Example 5

Analysis of Markers for Different Cell Types in the Brain

To further examine the types of cells that were transduced with the pseudotyped vectors, antibodies to specific markers present on different cell types were used. In particular, primary antibodies against the neuronal specific marker, NeuN, and glial cell specific marker, GFAP, were used. The EGFP transduced cells in the brain were examined by incubating sections of the brain with primary antibodies NeuN diluted in buffer (1:200, Chemicon), and GFAP (1:1000, Chemicon). The secondary fluorescent antibody, Cy3 (1:100, Jackson) was used to bind to the primary antibody. The sections of the brain were observed under the Confocal microscope.

The results demonstrate that the major cells infected by both the AAV2-AAV2 and AAV5-AAV2 pseudotyped vectors were NeuN positive cells, i.e., hippocampus pyramidal cells, grannul cells, inter neurons, and striatum neurons of different shapes and sizes. These cells appeared red in both the ipsilateral hippocampus and collateral hippocampus examined at ×40 magnification. Similarly, the AAV1-AAV2 pseudotyped vector also transduced almost exclusively to the neurons.

In the hippocampus, AAV1-AAV2 pseudotyped vector infected pyramidal neurons in the region CA1, CA2 and CA3, grannule cell layer in the dentate gyrus. The fibers in the contralateral sites of the hippocampus also turned green, suggesting that these fibers arise from the transduced neurons from injected sites. Moreover, some of the neuron cell bodies in the contralateral sites were also GFP positive, although much weaker compared with ipisilateral sites. These contralateral transduced cells were located in the CA2, CA3 and halius area. The CA1 region and granule cells in the dentate gyrus remained uninfected at the same time. One reasonable explanation as to why the neurons were transduced, was that these cells had terminals in the injected sites and virus entered into the cells from their terminal and slowed traveled to the soma.

These results also demonstrate that the transduction rate with the AAV1-AAV2 pseudotyped vector was much higher than the transduction rate with AAV2-AAV2. When the same amounts of CBA-EGFP, AAV1-AAV2 and AAV2-AAV2 vectors were delivered into the hippocampus, and striatum of the brain, the EGFP expression level with the AAV1-AAV2 pseudotyped vector was 10 fold higher than that of AAV2-AAV2. The AAV1-AAV2 pseudotyped vector also diffused a greater distance from the injection site than the AAV2-AAV2 vector. When AAV 1-AAV2 was delivered into the hippocampus, the whole hippocampus was transduced, while only small area around needle tract was transduced by AAV2-AAV2 vector. Collectively, these results demonstrate that the AAV 1-AAV2 pseudotype vector is a suitable vector for gene delivery in the CNS. The AAV1-AAV2 pseudotype vector shows a higher yield, efficient transduction rate, and transduces a more extensive cell number and volume in the CNS, than the other pseuodotyped vectors. For all these reasons, the AAV1-AAV2 pseudotype vector is suitable for delivering genes to a target site in the CNS.

---

We claim:

1. A recombinant virion comprising SEQ ID NO:11.

2. The recombinant virion of claim 1, wherein the virion further comprises a transgene.

3. The recombinant virion of claim 1, wherein the virion further comprises a transgene expression cassette.

4. The recombinant virion of claim 3, wherein the transgene expression cassette comprises a transgene.

5. The recombinant virion of claim 3, wherein the transgene expression cassette comprises a tissue-specific promoter.

6. The recombinant virion of claim 5, wherein the tissue-specific promoter is operable in cells of the central nervous system.

7. The recombinant virion of claim 5, wherein the tissue-specific promoter is a neuron-specific promoter.

8. The recombinant virion of claim 5, wherein the tissue-specific promoter is a pyramidal cell-specific promoter.

9. The recombinant virion of claim 1, wherein the virion further comprises control elements that are functional in a brain neuron.

10. The recombinant virion of claim 1, wherein the virion further comprises control elements that are functional in a striatum.

11. The recombinant virion of claim 1, wherein the virion further comprises control elements that are functional in a hippocampus.

* * * * *

SEQUENCE LISTING

```
<160> NUMBER OF SEQ ID NOS: 15

<210> SEQ ID NO 1
<211> LENGTH: 4718
<212> TYPE: DNA
<213> ORGANISM: adeno-associated virus 2

<400> SEQUENCE: 1

ttgcccactc cctctctgcg cgctcgctcg ctcggtgggg cctgcggacc aaaggtccgc      60

agacggcaga gctctgctct gccggcccca ccgagcgagc gagcgcgcag agagggagtg     120

ggcaactcca tcactagggg taatcgcgaa gcgcctccca cgctgccgcg tcagcgctga     180

cgtaaattac gtcatagggg agtggtcctg tattagctgt cacgtgagtg cttttgcgac     240

attttgcgac accacgtggc catttagggt atatatggcc gagtgagcga gcaggatctc     300

cattttgacc gcgaaatttg aacgagcagc agccatgccg ggcttctacg agatcgtgat     360

caaggtgccg agcgacctgg acgagcacct gccgggcatt tctgactcgt ttgtgagctg     420

ggtggccgag aaggaatggg agctgccccc ggattctgac atggatctga atctgattga     480

gcaggcaccc ctgaccgtgg ccgagaagct gcagcgcgac ttcctggtcc aatggcgccg     540

cgtgagtaag gccccggagg ccctcttctt tgttcagttc gagaagggcg agtcctactt     600

ccacctccat attctggtgg agaccacggg ggtcaaatcc atggtgctgg gccgcttcct     660

gagtcagatt agggacaagc tggtgcagac catctaccgc gggatcgagc cgaccctgcc     720

caactggttc gcggtgacca agacgcgtaa tggcgccgga gggggaaca aggtggtgga      780

cgagtgctac atccccaact acctcctgcc caagactcag cccgagctgc agtgggcgtg     840

gactaacatg gaggagtata taagcgcctg tttgaacctg gccgagcgca aacggctcgt     900

ggcgcagcac ctgacccacg tcagccagac ccaggagcag aacaaggaga atctgaaccc     960

caattctgac gcgcctgtca tccggtcaaa aacctccgcg cgctacatgg agctggtcgg    1020

gtggctggtg gaccggggca tcacctccga gaagcagtgg atccaggagg accaggcctc    1080

gtacatctcc ttcaacgccg cttccaactc gcggtcccag atcaaggccg ctctggacaa    1140

tgccggcaag atcatggcgc tgaccaaatc cgcgcccgac tacctggtag gccccgctcc    1200

gcccgcggac attaaaacca accgcatcta ccgcatcctg gagctgaacg gctacgaacc    1260

tgcctacgcc ggctccgtct ttctcggctg ggcccagaaa aggttcggga agcgcaacac    1320

catctggctg tttgggccgg ccaccacggg caagaccaac atcgcggaag ccatcgccca    1380

cgccgtgccc ttctacggct gcgtcaactg gaccaatgag aactttccct tcaatgattg    1440

cgtcgacaag atggtgatct ggtgggagga gggcaagatg acggccaagg tcgtggagtc    1500

cgccaaggcc attctcggcg gcagcaaggt gcgcgtggac caaaagtgca agtcgtccgc    1560

ccagatcgac cccacccccg tgatcgtcac ctccaacacc aacatgtgcg ccgtgattga    1620

cgggaacagc accaccttcg agcaccagca gccgttgcag gaccggatgt tcaaatttga    1680
```

-continued

```
actcacccgc cgtctggagc atgactttgg caaggtgaca aagcaggaag tcaaagagtt   1740
cttccgctgg gcgcaggatc acgtgaccga ggtggcgcat gagttctacg tcagaaaggg   1800
tggagccaac aaaagacccg cccccgatga cgcggataaa agcgagccca agcgggcctg   1860
cccctcagtc gcggatccat cgacgtcaga cgcggaagga gctccggtgg actttgccga   1920
caggtaccaa aacaaatgtt ctcgtcacgc gggcatgctt cagatgctgt ttccctgcaa   1980
gacatgcgag agaatgaatc agaatttcaa catttgcttc acgcacggga cgagagactg   2040
ttcagagtgc ttccccggcg tgtcagaatc tcaaccggtc gtcagaaaga ggacgtatcg   2100
gaaactctgt gccattcatc atctgctggg gcgggctccc gagattgctt gctcggcctg   2160
cgatctggtc aacgtggacc tggatgactg tgtttctgag caataaatga cttaaaccag   2220
gtatggctgc cgatggttat cttccagatt ggctcgagga caacctctct gagggcattc   2280
gcgagtggtg ggacttgaaa cctggagccc cgaagcccaa agccaaccag caaaagcagg   2340
acgacggccg gggtctggtg cttcctggct acaagtacct cggacccttc aacggactcg   2400
acaaggggga gcccgtcaac gcggcggacg cagcggccct cgagcacgac aaggcctacg   2460
accagcagct caaagcgggt gacaatccgt acctgcggta taaccacgcc gacgccgagt   2520
ttcaggagcg tctgcaagaa gatacgtctt ttgggggcaa cctcgggcga gcagtcttcc   2580
aggccaagaa gcgggttctc gaacctctcg gtctggttga ggaaggcgct aagacggctc   2640
ctggaaagaa acgtccggta gagcagtcgc cacaagagcc agactcctcc tcgggcatcg   2700
gcaagacagg ccagcagccc gctaaaaaga gactcaattt tggtcagact ggcgactcag   2760
agtcagtccc cgatccacaa cctctcggag aacctccagc aacccccgct gctgtgggac   2820
ctactacaat ggcttcaggc ggtggcgcac caatggcaga caataacgaa ggcgccgacg   2880
gagtgggtaa tgcctcagga aattggcatt gcgattccac atggctgggc gacagagtca   2940
tcaccaccag cacccgcacc tgggccttgc ccacctacaa taaccacctc tacaagcaaa   3000
tctccagtgc ttcaacgggg gccagcaacg acaaccacta cttcggctac agcaccccct   3060
gggggtattt tgatttcaac agattccact gccacttttc accacgtgac tggcagcgac   3120
tcatcaacaa caattgggga ttccggccca agagactcaa cttcaaactc ttcaacatcc   3180
aagtcaagga ggtcacgacg aatgatggcg tcacaaccat cgctaataac cttaccagca   3240
cggttcaagt cttctcggac tcggagtacc agcttccgta cgtcctcggc tctgcgcacc   3300
agggctgcct ccctccgttc ccggcggacg tgttcatgat tccgcaatac ggctacctga   3360
cgctcaacaa tggcagccaa gccgtgggac gttcatcctt ttactgcctg gaatatttcc   3420
cttctcagat gctgagaacg ggcaacaact ttaccttcag ctacaccttt gaggaagtgc   3480
ctttccacag cagctacgcg cacagccaga gcctggaccg gctgatgaat cctctcatcg   3540
accaatacct gtattacctg aacagaactc aaaatcagtc cggaagtgcc caaaacaagg   3600
acttgctgtt tagccgtggg tctccagctg gcatgtctgt tcagcccaaa aactggctac   3660
ctggaccctg ttatcggcag cagcgcgttt ctaaaacaaa aacagacaac aacaacagca   3720
attttacctg gactggtgct tcaaaatata acctcaatgg gcgtgaatcc atcatcaacc   3780
ctggcactgc tatggcctca cacaaagacg acgaagacaa gttctttccc atgagcggtg   3840
tcatgatttt tggaaaagag agcgccggag cttcaaacac tgcattggac aatgtcatga   3900
ttacagacga agaggaaatt aaagccacta accctgtggc caccgaaaga tttgggaccg   3960
tggcagtcaa tttccagagc agcagcacag accctgcgac cggagatgtg catgctatgg   4020
gagcattacc tggcatggtg tggcaagata gagacgtgta cctgcagggt cccatttggg   4080
```

-continued

```
ccaaaattcc tcacacagat ggacactttc acccgtctcc tcttatgggc ggctttggac   4140
tcaagaaccc gcctcctcag atcctcatca aaaacacgcc tgttcctgcg aatcctccgg   4200
cggagttttc agctacaaag tttgcttcat tcatcaccca atactccaca ggacaagtga   4260
gtgtggaaat tgaatgggag ctgcagaaag aaaacagcaa gcgctggaat cccgaagtgc   4320
agtacacatc caattatgca aaatctgcca acgttgattt tactgtggac aacaatggac   4380
tttatactga gcctcgcccc attggcaccc gttaccttac ccgtcccctg taattacgtg   4440
ttaatcaata aaccggttga ttcgtttcag ttgaactttg gtctcctgtc cttcttatct   4500
tatcggttac catggttata gcttacacat taactgcttg gttgcgcttc gcgataaaag   4560
acttacgtca tcgggttacc cctagtgatg gagttgccca ctccctctct gcgcgctcgc   4620
tcgctcggtg gggcctgcgg accaaaggtc cgcagacggc agagctctgc tctgccggcc   4680
ccaccgagcg agcgagcgcg cagagaggga gtgggcaa                           4718
```

<210> SEQ ID NO 2
<211> LENGTH: 4675
<212> TYPE: DNA
<213> ORGANISM: adeno-associated virus 2

<400> SEQUENCE: 2

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctggagg ggtggagtcg tgacgtgaat tacgtcatag    180
ggttagggag gtcctgtatt agaggtcacg tgagtgtttt gcgacatttt gcgacaccat    240
gtggtcacgc tgggtattta agcccgagtg agcacgcagg gtctccattt tgaagcggga    300
ggtttgaacg cgcagccgcc atgccggggt tttacgagat tgtgattaag gtccccagcg    360
accttgacgg gcatctgccc ggcatttctg acagctttgt gaactgggtg gccgagaagg    420
aatgggagtt gccgccagat tctgacatgg atctgaatct gattgagcag gcacccctga    480
ccgtggccga gaagctgcag cgcgactttc tgacggaatg gcgccgtgtg agtaaggccc    540
cggaggccct tttctttgtg caatttgaga agggagagag ctacttccac atgcacgtgc    600
tcgtggaaac caccggggtg aaatccatgg ttttgggacg tttcctgagt cagattcgcg    660
aaaaactgat tcagagaatt taccgcggga tcgagccgac tttgccaaac tggttcgcgg    720
tcacaaagac cagaaatggc gccggaggcg ggaacaaggt ggtggatgag tgctacatcc    780
ccaattactt gctccccaaa acccagcctg agctccagtg ggcgtggact aatatggaac    840
agtatttaag cgcctgtttg aatctcacgg agcgtaaacg gttggtggcg cagcatctga    900
cgcacgtgtc gcagacgcag gagcagaaca aagagaatca gaatcccaat tctgatgcgc    960
cggtgatcag atcaaaaact tcagccaggt acatggagct ggtcgggtgg ctcgtggaca   1020
aggggattac ctcggagaag cagtggatcc aggaggacca ggcctcatac atctccttca   1080
atgcggcctc caactcgcgg tcccaaatca aggctgcctt ggacaatgcg ggaaagatta   1140
tgagcctgac taaaaccgcc cccgactacc tggtgggcca gcagcccgtg gaggacattt   1200
ccagcaatcg gatttataaa attttggaac taaacgggta cgatccccaa tatgcggctt   1260
ccgtctttct gggatgggcc acgaaaaagt tcggcaagag gaacaccatc tggctgtttg   1320
ggcctgcaac taccgggaag accaacatcg cggaggccat agcccacact gtgcccttct   1380
acgggtgcgt aaactggacc aatgagaact ttcccttcaa cgactgtgtc gacaagatgg   1440
```

-continued

```
tgatctggtg ggaggagggg aagatgaccg ccaaggtcgt ggagtcggcc aaagccattc   1500
tcggaggaag caaggtgcgc gtggaccaga aatgcaagtc ctcggcccag atagacccga   1560
ctcccgtgat cgtcacctcc aacaccaaca tgtgcgccgt gattgacggg aactcaacga   1620
ccttcgaaca ccagcagccg ttgcaagacc ggatgttcaa atttgaactc acccgccgtc   1680
tggatcatga ctttgggaag gtcaccaagc aggaagtcaa agactttttc cggtgggcaa   1740
aggatcacgt ggttgaggtg gagcatgaat tctacgtcaa aaagggtgga gccaagaaaa   1800
gacccgcccc cagtgacgca gatataagtg agcccaaacg ggtgcgcgag tcagttgcgc   1860
agccatcgac gtcagacgcg gaagcttcga tcaactacgc agacaggtac caaaacaaat   1920
gttctcgtca cgtgggcatg aatctgatgc tgtttccctg cagacaatgc gagagaatga   1980
atcagaattc aaatatctgc ttcactcacg gacagaaaga ctgtttagag tgctttcccg   2040
tgtcagaatc tcaacccgtt tctgtcgtca aaaaggcgta tcagaaactg tgctacattc   2100
atcatatcat gggaaaggtg ccagacgctt gcactgcctg cgatctggtc aatgtggatt   2160
tggatgactg catctttgaa caataaatga tttaaatcag gtatggctgc cgatggttat   2220
cttccagatt ggctcgagga cactctctct gaaggaataa gacagtggtg gaagctcaaa   2280
cctggcccac caccaccaaa gcccgcagag cggcataagg acgacagcag gggtcttgtg   2340
cttcctgggt acaagtacct cggacccttc aacggactcg acaagggaga gccggtcaac   2400
gaggcagacg ccgcggccct cgagcacgta caaagcctac gaccggcagc tcgacagcgg   2460
agacaacccg tacctcaagt acaaccacgc cgacgcggag tttcaggagc gccttaaaga   2520
agatacgtct tttgggggca acctcggacg agcagtcttc caggcgaaaa agagggttct   2580
tgaacctctg ggcctggttg aggaacctgt taagacggct ccgggaaaaa agaggccggt   2640
agagcactct cctgtggagc cagactcctc ctcgggaacc ggaaaggcgg gccagcagcc   2700
tgcaagaaaa agattgaatt ttggtcagac tggagacgca gactcagtac ctgaccccca   2760
gcctctcgga cagccaccag cagccccctc tggtctggga actaatacga tggctacagg   2820
cagtggcgca ccaatggcag acaataacga gggcgccgac ggagtgggta attcctccgg   2880
aaattggcat tgcgattcca catggatggg cgacagagtc atcaccacca gcacccgaac   2940
ctgggccctg cccacctaca acaaccacct ctacaaacaa atttccagcc aatcaggagc   3000
ctcgaacgac aatcactact ttggctacag caccccttgg gggtattttg acttcaacag   3060
attccactgc cacttttcac cacgtgactg gcaaagactc atcaacaaca actggggatt   3120
ccgacccaag agactcaact tcaagctctt taacattcaa gtcaaagagg tcacgcagaa   3180
tgacggtacg acgacgattg ccaataacct taccagcacg gttcaggtgt ttactgactc   3240
ggagtaccag ctcccgtacg tcctcggctc ggcgcatcaa ggatgcctcc cgccgttccc   3300
agcagacgtc ttcatggtgc cacagtatgg atacctcacc ctgaacaacg ggagtcaggc   3360
agtaggacgc tcttcatttt actgcctgga gtactttcct tctcagatgc tgcgtaccgg   3420
aaacaacttt accttcagct acacttttga ggacgttcct ttccacagca gctacgctca   3480
cagccagagt ctggaccgtc tcatgaatcc tctcatcgac cagtacctgt attacttgag   3540
cagaacaaac actccaagtg gaaccaccac gcagtcaagg cttcagtttt ctcaggccgg   3600
agcgagtgac attcgggacc agtctaggaa ctggcttcct ggaccctgtt accgccagca   3660
gcgagtatca aagacatctg cggataacaa caacagtgaa tactcgtgga ctggagctac   3720
caagtaccac ctcaatggca gagactctct ggtgaatccg gccatggcaa gccacaagga   3780
cgatgaagaa aagtttttc ctcagagcgg ggttctcatc tttgggaagc aaggctcaga   3840
```

-continued

```
gaaaacaaat gtgaacattg aaaaggtcat gattacagac gaagaggaaa tcggaacaac   3900
caatcccgtg gctacggagc agtatggttc tgtatctacc aacctccaga gaggcaacag   3960
acaagcagct accgcagatg tcaacacaca aggcgttctt ccaggcatgg tctggcagga   4020
cagagatgtg taccttcagg ggcccatctg ggcaaagatt ccacacacgg acggacattt   4080
tcacccctct cccctcatgg gtggattcgg acttaaacac cctcctccac agattctcat   4140
caagaacacc ccggtacctg cgaatccttc gaccaccttc agtgcggcaa agtttgcttc   4200
cttcatcaca cagtactcca cgggacacgg tcagcgtgga gatcgagtgg gagctgcaga   4260
aggaaaacag caaacgctgg aatcccgaaa ttcagtacac ttccaactac aacaagtctg   4320
ttaatcgtgg acttaccgtg gatactaatg gcgtgtattc agagcctcgc cccattggca   4380
ccagatacct gactcgtaat ctgtaattgc ttgttaatca ataaaccgtt taattcgttt   4440
cagttgaact ttggtctctg cgtatttctt tcttatctag tttccatggc tacgtagata   4500
agtagcatgg cgggttaatc attaactaca aggaacccct agtgatggag ttggccactc   4560
cctctctgcg cgctcgctcg ctcactgagg ccgggcgacc aaaggtcgcc cgacgcccgg   4620
gctttgcccg ggcggcctca gtgagcgagc gagcgcgcag agagggagtg gccaa        4675
```

```
<210> SEQ ID NO 3
<211> LENGTH: 4722
<212> TYPE: DNA
<213> ORGANISM: adeno-associated virus 2

<400> SEQUENCE: 3

tggccactcc ctctatgcgc actcgctcgc tcggtggggc ctggcgacca aaggtcgcca     60
gacggacgtg ctttgcacgt ccggccccac cgagcgagcg agtgcgcata gagggagtgg    120
ccaactccat cactagaggt atggcagtga cgtaacgcga agcgcgcgaa gcgagaccac    180
gcctaccagc tgcgtcagca gtcaggtgac ccttttgcga cagtttgcga caccacgtgg    240
ccgctgaggg tatatattct cgagtgagcg aaccaggagc tccattttga ccgcgaaatt    300
tgaacgagca gcagccatgc cggggttcta cgagattgtc ctgaaggtcc cgagtgacct    360
ggacgagcac ctgccgggca tttctaactc gtttgttaac tgggtggccg agaaggaatg    420
ggagctgccg ccggattctg acatggatcc gaatctgatt gagcaggcac ccctgaccgt    480
ggccgaaaag cttcagcgcg agttcctggt ggagtggcgc cgcgtgagta aggccccgga    540
ggccctcttt tttgtccagt tcgaaaaggg ggagacctac ttccacctgc acgtgctgat    600
tgagaccatc ggggtcaaat ccatggtggt cggccgctac gtgagccaga ttaaagagaa    660
gctggtgacc cgcatctacc gcggggtcga gccgcagctt ccgaactggt tcgcggtgac    720
caaaacgcga aatggcgccg gggcgggaa caaggtggtg gacgactgct acatccccaa     780
ctacctgctc cccaagaccc agcccgagct ccagtgggcg tggactaaca tggaccagta    840
tttaagcgcc tgtttgaatc tcgcggagcg taaacggctg gtggcgcagc atctgacgca    900
cgtgtcgcag acgcaggagc agaacaaaga gaatcagaac cccaattctg acgcgccggt    960
catcaggtca aaaacctcag ccaggtacat ggagctggtc gggtggctgg tggaccgcgg   1020
gatcacgtca gaaaagcaat ggattcagga ggaccaggcc tcgtacatct ccttcaacgc   1080
cgcctccaac tcgcggtccc agatcaaggc cgcgctggac aatgcctcca agatcatgag   1140
cctgacaaag acggctccgg actacctggt gggcagcaac ccgccggagg acattaccaa   1200
aaatcggatc taccaaatcc tggagctgaa cgggtacgat ccgcagtacg cggcctccgt   1260
```

-continued

```
cttcctgggc tgggcgcaaa agaagttcgg gaagaggaac accatctggc tctttgggcc   1320
ggccacgacg ggtaaaacca acatcgcgga agccatcgcc cacgccgtgc ccttctacgg   1380
ctgcgtaaac tggaccaatg agaactttcc cttcaacgat tgcgtcgaca agatggtgat   1440
ctggtgggag gagggcaaga tgacggccaa ggtcgtggag agcgccaagg ccattctggg   1500
cggaagcaag gtgcgcgtgg accaaaagtg caagtcatcg gcccagatcg aacccactcc   1560
cgtgatcgtc acctccaaca ccaacatgtg cgccgtgatt gacgggaaca gcaccacctt   1620
cgagcatcag cagccgctgc aggaccggat gtttaaattt gaacttaccc gccgtttgga   1680
ccatgacttt gggaaggtca ccaaacagga agtaaaggac tttttccggt gggcttccga   1740
tcacgtgact gacgtggctc atgagttcta cgtcagaaag ggtggagcta agaaacgccc   1800
cgcctccaat gacgcggatg taagcgagcc aaaacggcag tgcacgtcac ttgcgcagcc   1860
gacaacgtca gacgcggaag caccggcgga ctacgcggac aggtaccaaa acaaatgttc   1920
tcgtcacgtg ggcatgaatc tgatgctttt tccctgtaaa acatgcgaga gaatgaatca   1980
aatttccaat gtctgtttta cgcatggtca aagagactgt ggggaatgct tccctggaat   2040
gtcagaatct caacccgttt ctgtcgtcaa aaagaagact tatcagaaac tgtgtccaat   2100
tcatcatatc ctgggaaggg cacccgagat tgcctgttcg gcctgcgatt tggccaatgt   2160
ggacttggat gactgtgttt ctgagcaata aatgacttaa accaggtatg gctgctgacg   2220
gttatcttcc agattggctc gaggacaacc tttctgaagg cattcgtgag tggtgggctc   2280
tgaaacctgg agtccctcaa cccaaagcga accaacaaca ccaggacaac cgtcggggtc   2340
ttgtgcttcc gggttacaaa tacctcggac ccggtaacgg actcgacaaa ggagagccgg   2400
tcaacgaggc ggacgcggca gccctcgaac acgacaaagc ttacgaccag cagctcaagg   2460
ccggtgacaa cccgtacctc aagtacaacc acgccgacgc cgagtttcag gagcgtcttc   2520
aagaagatac gtcttttggg ggcaaccttg gcagagcagt cttccaggcc aaaaagagga   2580
tccttgagcc tcttggtctg gttgaggaag cagctaaaac ggctcctgga aagaagaggc   2640
ctgtagatca gtctcctcag gaaccggact catcatctgg tgttggcaaa tcgggcaaac   2700
agcctgccag aaaaagacta aatttcggtc agactggcga ctcagagtca gtcccagacc   2760
ctcaacctct cggagaacca ccagcagccc ccacaagttt gggatctaat acaatggctt   2820
caggcggtgg cgcaccaatg gcagacaata acgagggtgc cgatggagtg ggtaattcct   2880
caggaaattg gcattgcgat tcccaatggc tgggcgacag agtcatcacc accagcacca   2940
gaacctgggc cctgcccact tacaacaacc atctctacaa gcaaatctcc agccaatcag   3000
gagcttcaaa cgacaaccac tactttggct acagcacccc ttgggggtat tttgacttta   3060
acagattcca ctgccacttc tcaccacgtg actggcagcg actcattaac aacaactggg   3120
gattccggcc caagaaactc agcttcaagc tcttcaacat ccaagttaaa gaggtcacgc   3180
agaacgatgg cacgacgact attgccaata accttaccag cacggttcaa gtgtttacgg   3240
actcggagta tcagctcccg tacgtgctcg ggtcggcgca ccaaggctgt ctcccgccgt   3300
ttccagcgga cgtcttcatg gtccctcagt atggatacct caccctgaac aacggaagtc   3360
aagcggtggg acgctcatcc ttttactgcc tggagtactt cccttcgcag atgctaagga   3420
ctggaaataa cttccaattc agctatacct tcgaggatgt accttttcac agcagctacg   3480
ctcacagcca gagtttggat cgcttgatga atcctcttat tgatcagtat ctgtactacc   3540
tgaacagaac gcaaggaaca acctctggaa caaccaacca atcacggctg ctttttagcc   3600
aggctgggcc tcagtctatg tctttgcagg ccagaaattg gctacctggg ccctgctacc   3660
```

-continued

```
ggcaacagag actttcaaag actgctaacg acaacaacaa cagtaacttt ccttggacag   3720

cggccagcaa atatcatctc aatggccgcg actcgctggt gaatccagga ccagctatgg   3780

ccagtcacaa ggacgatgaa gaaaaatttt tccctatgca cggcaatcta atatttggca   3840

aagaagggac aacggcaagt aacgcagaat tagataatgt aatgattacg gatgaagaag   3900

agattcgtac caccaatcct gtggcaacag agcagtatgg aactgtggca aataacttgc   3960

agagctcaaa tacagctccc acgactagaa ctgtcaatga tcaggggggcc ttacctggca   4020

tggtgtggca agatcgtgac gtgtaccttc aaggacctat ctgggcaaag attcctcaca   4080

cggatggaca ctttcatcct tctcctctga tgggaggctt tggactgaaa catccgcctc   4140

ctcaaatcat gatcaaaaat actccggtac cggcaaatcc tccgacgact ttcagcccgg   4200

ccaagtttgc ttcatttatc actcagtact ccactggaca ggtcagcgtg gaaattgagt   4260

gggagctaca gaaagaaaac agcaaacgtt ggaatccaga gattcagtac acttccaact   4320

acaacaagtc tgttaatgtg gactttactg tagacactaa tggtgtttat agtgaacctc   4380

gccctattgg aacccggtat ctcacacgaa acttgtaatc ctggttaatc aataaaccgt   4440

ttaattcgtt tcagttgaac tttggctctt gtgcacttct tatcttatct tgtttccatg   4500

gctactgcgt agataagcag cggcctgcgg cgcttgcgct tcgcggttta caactgctgg   4560

ttaatattta actctcgcca tacctctagt gatggagttg gccactccct ctatgcgcac   4620

tcgctcgctc ggtggggccg gacgtgcaaa gcacgtccgt ctggcgacct ttggtcgcca   4680

ggccccaccg agcgagcgag tgcgcataga gggagtggcc aa                      4722
```

<210> SEQ ID NO 4
<211> LENGTH: 4767
<212> TYPE: DNA
<213> ORGANISM: adeno-associated virus 2

<400> SEQUENCE: 4

```
ttggccactc cctctatgcg cgctcgctca ctcactcggc cctggagacc aaaggtctcc     60

agactgccgg cctctggccg gcagggccga gtgagtgagc gagcgcgcat agagggagtg    120

gccaactcca tcatctaggt ttgcccactg acgtcaatgt gacgtcctag ggttagggag    180

gtccctgtat tagcagtcac gtgagtgtcg tatttcgcgg agcgtagcgg agcgcatacc    240

aagctgccac gtcacagcca cgtggtccgt ttgcgacagt ttgcgacacc atgtggtcag    300

gagggtatat aaccgcgagt gagccagcga ggagctccat tttgcccgcg aattttgaac    360

gagcagcagc catgccgggg ttctacgaga tcgtgctgaa ggtgcccagc gacctggacg    420

agcacctgcc cggcatttct gactcttttg tgagctgggt ggccgagaag gaatgggagc    480

tgccgccgga ttctgacatg gacttgaatc tgattgagca ggcacccctg accgtggccg    540

aaaagctgca acgcgagttc ctggtcgagt ggcgccgcgt gagtaaggcc ccggaggccc    600

tcttctttgt ccagttcgag aaggggggaca gctacttcca cctgcacatc ctggtggaga    660

ccgtgggcgt caaatccatg gtggtgggcc gctacgtgag ccagattaaa gagaagctgg    720

tgacccgcat ctaccgcggg gtcgagccgc agcttccgaa ctggttcgcg gtgaccaaga    780

cgcgtaatgg cgccggaggc gggaacaagg tggtggacga ctgctacatc cccaactacc    840

tgctccccaa gacccagccc gagctccagt gggcgtggac taacatggac cagtatataa    900

gcgcctgttt gaatctcgcg gagcgtaaac ggctggtggc gcagcatctg acgcacgtgt    960

cgcagacgca ggagcagaac aaggaaaacc agaaccccaa ttctgacgcg ccggtcatca   1020
```

-continued

```
ggtcaaaaac ctccgccagg tacatggagc tggtcgggtg gctggtggac cgcgggatca   1080
cgtcagaaaa gcaatggatc caggaggacc aggcgtccta catctccttc aacgccgcct   1140
ccaactcgcg gtcacaaatc aaggccgcgc tggacaatgc ctccaaaatc atgagcctga   1200
caaagacggc tccggactac ctggtgggcc agaacccgcc ggaggacatt tccagcaacc   1260
gcatctaccg aatcctcgag atgaacgggt acgatccgca gtacgcggcc tccgtcttcc   1320
tgggctgggc gcaaaagaag ttcgggaaga ggaacaccat ctggctcttt gggccggcca   1380
cgacgggtaa aaccaacatc gcggaagcca tcgcccacgc cgtgcccttc tacggctgcg   1440
tgaactggac caatgagaac tttccgttca acgattgcgt cgacaagatg gtgatctggt   1500
gggaggaggg caagatgacg gccaaggtcg tagagagcgc caaggccatc ctgggcggaa   1560
gcaaggtgcg cgtggaccaa aagtgcaagt catcggccca gatcgaccca actcccgtga   1620
tcgtcacctc caacaccaac atgtgcgcgg tcatcgacgg aaactcgacc accttcgagc   1680
accaacaacc actccaggac cggatgttca agttcgagct caccaagcgc ctggagcacg   1740
actttggcaa ggtcaccaag caggaagtca aagacttttt ccggtgggcg tcagatcacg   1800
tgaccgaggt gactcacgag ttttacgtca gaaagggtgg agctagaaag aggcccgccc   1860
ccaatgacgc agatataagt gagcccaagc gggcctgtcc gtcagttgcg cagccatcga   1920
cgtcagacgc ggaagctccg gtggactacg cggacaggta ccaaaacaaa tgttctcgtc   1980
acgtgggtat gaatctgatg ctttttccct gccggcaatg cgagagaatg aatcagaatg   2040
tggacatttg cttcacgcac ggggtcatgg actgtgccga gtgcttcccc gtgtcagaat   2100
ctcaacccgt gtctgtcgtc agaaagcgga cgtatcagaa actgtgtccg attcatcaca   2160
tcatggggag ggcgcccgag gtggcctgct cggcctgcga actggccaat gtggacttgg   2220
atgactgtga catggaacaa taaatgactc aaaccagata tgactgacgg ttaccttcca   2280
gattggctag aggacaacct ctctgaaggc gttcgagagt ggtgggcgct gcaacctgga   2340
gcccctaaac ccaaggcaaa tcaacaacat caggacaacg ctcggggtct tgtgcttccg   2400
ggttacaaat acctcggacc cggcaacgga ctcgacaagg gggaacccgt caacgcagcg   2460
gacgcggcag ccctcgagca cgacaaggcc tacgaccagc agctcaaggc cggtgacaac   2520
ccctacctca agtacaacca cgccgacgcg gagttccagc agcggcttca gggcgacaca   2580
tcgtttgggg gcaacctcgg cagagcagtc ttccaggcca aaaagagggt tcttgaacct   2640
cttggtctgg ttgagcaagc gggtgagacg gctcctggaa agaagagacc gttgattgaa   2700
tccccccagc agcccgactc ctccacgggt atcggcaaaa aaggcaagca gccggctaaa   2760
aagaagctcg ttttcgaaga cgaaactgga gcaggcgacg gacccccctga gggatcaact   2820
tccggagcca tgtctgatga cagtgagatg cgtgcagcag ctggcggagc tgcagtcgag   2880
ggcggacaag gtgccgatgg agtgggtaat gcctcgggtg attggcattg cgattccacc   2940
tggtctgagg gccacgtcac gaccaccagc accagaacct gggtcttgcc cacctacaac   3000
aaccacctct acaagcgact cggagagagc ctgcagtcca acacctacaa cggattctcc   3060
accccctggg gatactttga cttcaaccgc ttccactgcc acttctcacc acgtgactgg   3120
cagcgactca tcaacaacaa ctggggcatg cgacccaaag ccatgcgggt caaaatcttc   3180
aacatccagg tcaaggaggt cacgacgtcg aacggcgaga caacggtggc taataacctt   3240
accagcacgg ttcagatctt tgcggactcg tcgtacgaac tgccgtacgt gatggatgcg   3300
ggtcaagagg gcagcctgcc tccttttccc aacgacgtct ttatggtgcc ccagtacggc   3360
tactgtggac tggtgaccgg caacacttcg cagcaacaga ctgacagaaa tgccttctac   3420
```

-continued tgcctggagt actttccttc gcagatgctg cggactggca acaactttga aattacgtac 3480
agttttgaga aggtgccttt ccactcgatg tacgcgcaca gccagagcct ggaccggctg 3540
atgaaccctc tcatcgacca gtacctgtgg ggactgcaat cgaccaccac cggaaccacc 3600
ctgaatgccg ggactgccac caccaacttt accaagctgc ggcctaccaa cttttccaac 3660
tttaaaaaga actggctgcc cgggccttca atcaagcagc agggcttctc aaagactgcc 3720
aatcaaaact acaagatccc tgccaccggg tcagacagtc tcatcaaata cgagacgcac 3780
agcactctgg acggaagatg gagtgccctg acccccggac ctccaatggc cacggctgga 3840
cctgcggaca gcaagttcag caacagccag ctcatctttg cggggcctaa acagaacggc 3900
aacacggcca ccgtacccgg gactctgatc ttcacctctg aggaggagct ggcagccacc 3960
aacgccaccg atacggacat gtggggcaac ctacctggcg gtgaccagag caacagcaac 4020
ctgccgaccg tggacagact gacagccttg ggagccgtgc ctggaatggt ctggcaaaac 4080
agagacattt actaccaggg tcccatttgg gccaagattc ctcataccga tggacacttt 4140
cacccctcac cgctgattgg tgggtttggg ctgaaacacc cgcctcctca aatttttatc 4200
aagaacaccc cggtacctgc gaatcctgca acgaccttca gctctactcc ggtaaactcc 4260
ttcattactc agtacagcac tggccaggtg tcggtgcaga ttgactggga gatccagaag 4320
gagcggtcca aacgctggaa ccccgaggtc cagtttacct ccaactacgg acagcaaaac 4380
tctctgttgt gggctcccga tgcggctggg aaatacactg agcctagggc tatcggtacc 4440
cgctacctca cccaccacct gtaataacct gttaatcaat aaaccggttt attcgtttca 4500
gttgaacttt ggtctccgtg tccttcttat cttatctcgt ttccatggct actgcgtaca 4560
taagcagcgg cctgcggcgc ttgcgcttcg cggtttacaa ctgccggtta atcagtaact 4620
tctggcaaac cagatgatgg agttggccac attagctatg cgcgctcgct cactcactcg 4680
gccctggaga ccaaaggtct ccagactgcc ggcctctggc cggcagggcc gagtgagtga 4740
gcgagcgcgc atagagggag tggccaa 4767

<210> SEQ ID NO 5
<211> LENGTH: 4652
<212> TYPE: DNA
<213> ORGANISM: adeno-associated virus 2

<400> SEQUENCE: 5
tggcactctc ccccctgtcg cgttcgctcg ctcgctggct cgtttggggg ggtggcagct 60
caaagagctg ccagacgacg gccctctggc cgtcgccccc ccaaacgagc cagcgagcga 120
gcgaacgcga cagggggag agtgccacac tctcaagcaa gggggttttg taagcagtga 180
tgtcataatg atgtaatgct tattgtcacg cgatagttaa tgattaacag tcatgtgatg 240
tgttttatcc aataggaaga aagcgcgcgt atgagttctc gcgagacttc cggggtataa 300
aagaccgagt gaacgagccc gccgccattc tttgctctgg actgctagag gaccctcgct 360
gccatggcta ccttctatga agtcattgtt cgcgtcccat ttgacgtgga ggaacatctg 420
cctggaattt ctgacagctt tgtggactgg gtaactggtc aaatttggga gctgcctcca 480
gagtcagatt taaatttgac tctggttgaa cagcctcagt tgacggtggc tgatagaatt 540
cgccgcgtgt tcctgtacga gtggaacaaa ttttccaagc aggagtccaa attctttgtg 600
cagtttgaaa agggatctga atattttcat ctgcacacgc ttgtggagac ctccggcatc 660
tcttccatgg tcctcggccg ctacgtgagt cagattcgcg cccagctggt gaaagtggtc 720

-continued

```
ttccagggaa ttgaacccca gatcaacgac tgggtcgcca tcaccaaggt aaagaagggc    780
ggagccaata aggtggtgga ttctgggtat attcccgcct acctgctgcc gaaggtccaa    840
ccggagcttc agtgggcgtg gacaaacctg gacgagtata aattggccgc cctgaatctg    900
gaggagcgca aacggctcgt cgcgcagttt ctggcagaat cctcgcagcg ctcgcaggag    960
gcggcttcgc agcgtgagtt ctcggctgac ccggtcatca aaagcaagac ttcccagaaa   1020
tacatggcgc tcgtcaactg gctcgtggag cacggcatca cttccgagaa gcagtggatc   1080
caggaaaatc aggagagcta cctctccttc aactccaccg gcaactctcg gagccagatc   1140
aaggccgcgc tcgacaacgc gaccaaaatt atgagtctga caaaaagcgc ggtggactac   1200
ctcgtgggga gctccgttcc cgaggacatt tcaaaaaaca gaatctggca aatttttgag   1260
atgaatggct acgacccggc ctacgcggga tccatcctct acggctggtg tcagcgctcc   1320
ttcaacaaga ggaacaccgt ctggctctac ggacccgcca cgaccggcaa gaccaacatc   1380
gcggaggcca tcgcccacac tgtgcccttt tacggctgcg tgaactggac caatgaaaac   1440
tttcccttta atgactgtgt ggacaaaatg ctcatttggt gggaggaggg aaagatgacc   1500
aacaaggtgg ttgaatccgc caaggccatc ctgggggggct caaaggtgcg ggtcgatcag   1560
aaatgtaaat cctctgttca aattgattct accccctgtca ttgtaacttc caatacaaac   1620
atgtgtgtgg tggtggatgg gaattccacg acctttgaac accagcagcc gctggaggac   1680
cgcatgttca aatttgaact gactaagcgg ctcccgccag attttggcaa gattactaag   1740
caggaagtca aggacttttt tgcttgggca aaggtcaatc aggtgccggt gactcacgag   1800
tttaaagttc ccagggaatt ggcgggaact aaaggggcgg agaaatctct aaaacgccca   1860
ctgggtgacg tcaccaatac tagctataaa agtctggaga agcgggccag gctctcattt   1920
gttcccgaga cgcctcgcag ttcagacgtg actgttgatc ccgctcctct gcgaccgctc   1980
aattggaatt caaggtatga ttgcaaatgt gactatcatg ctcaatttga caacatttct   2040
aacaaatgtg atgaatgtga atatttgaat cggggcaaaa atggatgtat ctgtcacaat   2100
gtaactcact gtcaaatttg tcatgggatt cccccctggg aaaaggaaaa cttgtcagat   2160
tttggggatt ttgacgatgc caataaagaa cagtaaataa agcgagtagt catgtctttt   2220
gttgatcacc ctccagattg gttggaagaa gttggtgaag gtcttcgcga gtttttgggc   2280
cttgaagcgg gcccaccgaa accaaaaccc aatcagcagc atcaagatca agcccgtggt   2340
cttgtgctgc ctggttataa ctatctcgga cccggaaacg gtctcgatcg aggagagcct   2400
gtcaacaggg cagacgaggt cgcgcgagag cacgacatct cgtacaacga gcagcttgag   2460
gcgggagaca accccctacct caagtacaac cacgcggacg ccgagtttca ggagaagctc   2520
gccgacgaca catccttcgg gggaaacctc ggaaaggcag tctttcaggc caagaaaagg   2580
gttctcgaac cttttggcct ggttgaagag ggtgctaaga cggcccctac cggaaagcgg   2640
atagacgacc actttccaaa aagaaagaag gctcggaccg aagaggactc caagccttcc   2700
acctcgtcag acgccgaagc tggacccagc ggatcccagc agctgcaaat cccagcccaa   2760
ccagcctcaa gtttgggagc tgatacaatg tctgcgggag gtggcggccc attgggcgac   2820
aataaccaag gtgccgatgg agtgggcaat gcctcgggag attggcattg cgattccacg   2880
tggatggggg acagagtcgt caccaagtcc acccgaacct gggtgctgcc cagctacaac   2940
aaccaccagt accgagagat caaaagcggc tccgtcgacg gaagcaacgc caacgcctac   3000
tttggataca gcaccccctg gggtactttt gactttaacc gcttccacag ccactggagc   3060
ccccgagact ggcaaagact catcaacaac tactggggct tcagaccccg gtccctcaga   3120
```

-continued

```
gtcaaaatct tcaacattca agtcaaagag gtcacggtgc aggactccac caccaccatc   3180

gccaacaacc tcacctccac cgtccaagtg tttacggacg acgactacca gctgccctac   3240

gtcgtcggca acgggaccga gggatgcctg ccggccttcc ctccgcaggt ctttacgctg   3300

ccgcagtacg gttacgcgac gctgaaccgc gacaacacag aaaatcccac cgagaggagc   3360

agcttcttct gcctagagta ctttcccagc aagatgctga gaacgggcaa caactttgag   3420

tttacctaca actttgagga ggtgcccttc cactccagct tcgctcccag tcagaacctg   3480

ttcaagctgg ccaacccgct ggtggaccag tacttgtacc gcttcgtgag cacaaataac   3540

actggcggag tccagttcaa caagaacctg gccgggagat acgccaacac ctacaaaaac   3600

tggttcccgg ggcccatggg ccgaacccag ggctggaacc tgggctccgg ggtcaaccgc   3660

gccagtgtca gcgccttcgc cacgaccaat aggatggagc tcgagggcgc gagttaccag   3720

gtgcccccgc agccgaacgg catgaccaac aacctccagg gcagcaacac ctatgccctg   3780

gagaacacta tgatcttcaa cagccagccg gcgaacccgg gcaccaccgc cacgtacctc   3840

gagggcaaca tgctcatcac cagcgagagc gagacgcagc cggtgaaccg cgtggcgtac   3900

aacgtcggcg ggcagatggc caccaacaac cagagctcca ccactgcccc cgcgaccggc   3960

acgtacaacc tccaggaaat cgtgcccggc agcgtgtgga tggagaggga cgtgtacctc   4020

caaggaccca tctgggccaa gatcccagag acgggggcgc actttcaccc ctctccggcc   4080

atgggcggat tcggactcaa acacccaccg cccatgatgc tcatcaagaa cacgcctgtg   4140

cccggaaata tcaccagctt ctcggacgtg cccgtcagca gcttcatcac ccagtacagc   4200

accgggcagg tcaccgtgga gatggagtgg gagctcaaga aggaaaactc caagaggtgg   4260

aacccagaga tccagtacac aaacaactac aacgaccccc agtttgtgga ctttgccccg   4320

gacagcaccg gggaatacag aaccaccaga cctatcggaa cccgatacct tacccgaccc   4380

ctttaaccca ttcatgtcgc ataccctcaa taaaccgtgt attcgtgtca gtaaaatact   4440

gcctcttgtg gtcattcaat gaataacagc ttacaacatc tacaaaacct ccttgcttga   4500

gagtgtggca ctctcccccc tgtcgcgttc gctcgctcgc tggctcgttt gggggggtgg   4560

cagctcaaag agctgccaga cgacggccct ctggccgtcg cccccccaaa cgagccagcg   4620

agcgagcgaa cgcgacaggg gggagagtgc ca                                 4652

<210> SEQ ID NO 6
<211> LENGTH: 4683
<212> TYPE: DNA
<213> ORGANISM: adeno-associated virus 2

<400> SEQUENCE: 6

ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctggagg ggtggagtcg tgacgtgaat tacgtcatag    180

ggttagggag gtcctgtatt agaggtcacg tgagtgtttt gcgacatttt gcgacaccat    240

gtggtcacgc tgggtattta agcccgagtg agcacgcagg gtctccattt tgaagcggga    300

ggtttgaacg cgcagcgcca tgccggggtt ttacgagatt gtgattaagg tccccagcga    360

ccttgacgag catctgcccg gcatttctga cagctttgtg aactgggtgg ccgagaagga    420

atgggagttg ccgccagatt ctgacatgga tctgaatctg attgagcagg cacccctgac    480

cgtggccgag aagctgcagc gcgacttcct ggtccagtgg cgccgcgtga gtaaggcccc    540
```

-continued

```
ggaggccctc ttctttgttc agttcgagaa gggcgagtcc tacttccacc tccatattct    600
ggtggagacc acgggggtca aatccatggt gctgggccgc ttcctgagtc agattaggga    660
caagctggtg cagaccatct accgcgggat cgagccgacc ctgcccaact ggttcgcggt    720
gaccaagacg cgtaatggcg ccggaggggg gaacaaggtg gtggacgagt gctacatccc    780
caactacctc ctgcccaaga ctcagcccga gctgcagtgg gcgtggacta acatggagga    840
gtatataagc gcgtgtttaa acctggccga gcgcaaacgg ctcgtggcgc acgacctgac    900
ccacgtcagc cagacccagg agcagaacaa ggagaatctg aaccccaatt ctgacgcgcc    960
tgtcatccgg tcaaaaacct ccgcacgcta catggagctg gtcgggtggc tggtggaccg   1020
gggcatcacc tccgagaagc agtggatcca ggaggaccag gcctcgtaca tctccttcaa   1080
cgccgcctcc aactcgcggt cccagatcaa ggccgctctg gacaatgccg gcaagatcat   1140
ggcgctgacc aaatccgcgc ccgactacct ggtaggcccc gctccgcccg ccgacattaa   1200
aaccaaccgc atttaccgca tcctggagct gaacggctac gaccctgcct acgccggctc   1260
cgtctttctc ggctgggccc agaaaaggtt cggaaaacgc aacaccatct ggctgtttgg   1320
gccggccacc acgggcaaga ccaacatcgc ggaagccatc gcccacgccg tgcccttcta   1380
cggctgcgtc aactggacca atgagaactt tcccttcaac gattgcgtcg acaagatggt   1440
gatctggtgg gaggagggca agatgacggc caaggtcgtg gagtccgcca aggccattct   1500
cggcggcagc aaggtgcgcg tggaccaaaa gtgcaagtcg tccgcccaga tcgatcccac   1560
ccccgtgatc gtcacctcca acaccaacat gtgcgccgtg attgacggga acagcaccac   1620
cttcgagcac cagcagccgt tgcaggaccg gatgttcaaa tttgaactca cccgccgtct   1680
ggagcatgac tttggcaagg tgacaaagca ggaagtcaaa gagttcttcc gctgggcgca   1740
ggatcacgtg accgaggtgg cgcatgagtt ctacgtcaga aagggtggag ccaacaagag   1800
acccgccccc gatgacgcgg ataaaagcga gcccaagcgg gcctgcccct cagtcgcgga   1860
tccatcgacg tcagacgcgg aaggagctcc ggtggacttt gccgacaggt accaaaacaa   1920
atgttctcgt cacgcgggca tgcttcagat gctgtttccc tgcaaaacat gcgagagaat   1980
gaatcagaat ttcaacattt gcttcacgca cgggaccaga gactgttcag aatgtttccc   2040
cggcgtgtca gaatctcaac cggtcgtcag aaagaggacg tatcggaaac tctgtgccat   2100
tcatcatctg ctggggcggg ctcccgagat tgcttgctcg gcctgcgatc tggtcaacgt   2160
ggatctggat gactgtgttt ctgagcaata aatgacttaa accaggtatg gctgccgatg   2220
gttatcttcc agattggctc gaggacaacc tctctgaggg cattcgcgag tggtgggact   2280
tgaaacctgg agccccgaaa cccaaagcca accagcaaaa gcaggacgac ggccggggtc   2340
tggtgcttcc tggctacaag tacctcggac ccttcaacgg actcgacaag ggggagcccg   2400
tcaacgcggc ggatgcagcg gccctcgagc acgacaaggc ctacgaccag cagctcaaag   2460
cgggtgacaa tccgtacctg cggtataacc acgccgacgc cgagtttcag gagcgtctgc   2520
aagaagatac gtcttttggg ggcaacctcg ggcgagcagt cttccaggcc aagaagaggg   2580
ttctcgaacc ttttggtctg gttgaggaag gtgctaagac ggctcctgga aagaaacgtc   2640
cggtagagca gtcgccacaa gagccagact cctcctcggg cattggcaag acaggccagc   2700
agcccgctaa aaagagactc aattttggtc agactggcga ctcagagtca gtccccgacc   2760
cacaacctct cggagaacct ccagcaaccc ccgctgctgt gggacctact acaatggctt   2820
caggcggtgg cgcaccaatg gcagacaata acgaaggcgc cgacggagtg ggtaatgcct   2880
caggaaattg gcattgcgat tccacatggc tgggcgacag agtcatcacc accagcaccc   2940
```

-continued

```
gaacatgggc cttgcccacc tataacaacc acctctacaa gcaaatctcc agtgcttcaa   3000

cgggggccag caacgacaac cactacttcg gctacagcac cccctggggg tattttgatt   3060

tcaacagatt ccactgccat ttctcaccac gtgactggca gcgactcatc aacaacaatt   3120

ggggattccg gcccaagaga ctcaacttca agctcttcaa catccaagtc aaggaggtca   3180

cgacgaatga tggcgtcacg accatcgcta ataaccttac cagcacggtt caagtcttct   3240

cggactcgga gtaccagttg ccgtacgtcc tcggctctgc gcaccagggc tgcctccctc   3300

cgttcccggc ggacgtgttc atgattccgc agtacggcta cctaacgctc aacaatggca   3360

gccaggcagt gggacggtca tccttttact gcctggaata tttcccatcg cagatgctga   3420

gaacgggcaa taactttacc ttcagctaca ccttcgagga cgtgcctttc cacagcagct   3480

acgcgcacag ccagagcctg gaccggctga tgaatcctct catcgaccag tacctgtatt   3540

acctgaacag aactcagaat cagtccggaa gtgcccaaaa caaggacttg ctgtttagcc   3600

gggggtctcc agctggcatg tctgttcagc ccaaaaactg gctacctgga ccctgttacc   3660

ggcagcagcg cgtttctaaa acaaaaacag acaacaacaa cagcaacttt acctggactg   3720

gtgcttcaaa atataacctt aatgggcgtg aatctataat caaccctggc actgctatgg   3780

cctcacacaa agacgacaaa gacaagttct ttcccatgag cggtgtcatg atttttggaa   3840

aggagagcgc cggagcttca aacactgcat tggacaatgt catgatcaca gacgaagagg   3900

aaatcaaagc cactaacccc gtggccaccg aaagatttgg gactgtggca gtcaatctcc   3960

agagcagcag cacagaccct gcgaccggag atgtgcatgt tatgggagcc ttacctggaa   4020

tggtgtggca agacagagac gtatacctgc agggtcctat ttgggccaaa attcctcaca   4080

cggatggaca ctttcacccg tctcctctca tgggcggctt tggacttaag cacccgcctc   4140

ctcagatcct catcaaaaac acgcctgttc ctgcgaatcc tccggcagag ttttcggcta   4200

caaagtttgc ttcattcatc acccagtatt ccacaggaca agtgagcgtg gagattgaat   4260

gggagctgca gaaagaaaac agcaaacgct ggaatcccga agtgcagtat acatctaact   4320

atgcaaaatc tgccaacgtt gatttcactg tggacaacaa tggactttat actgagcctc   4380

gccccattgg cacccgttac ctcacccgtc ccctgtaatt gtgtgttaat caataaaccg   4440

gttaattcgt gtcagttgaa ctttggtctc atgtcgttat tatcttatct ggtcaccata   4500

gcaaccggtt acacattaac tgcttagttg cgcttcgcga atacccctag tgatggagtt   4560

gcccactccc tctatgcgcg ctcgctcgct cggtggggcc ggcagagcag agctctgccg   4620

tctgcggacc tttggtccgc aggccccacc gagcgagcga gcgcgcatag agggagtggg   4680

caa                                                                 4683
```

```
<210> SEQ ID NO 7
<211> LENGTH: 30
<212> TYPE: DNA
<213> ORGANISM: adeno-associated virus 2

<400> SEQUENCE: 7

cgagtcagtt gcgcagccat cgacgtcaga                                      30


<210> SEQ ID NO 8
<211> LENGTH: 50
<212> TYPE: DNA
<213> ORGANISM: adeno-associated virus 2

<400> SEQUENCE: 8
```

-continued

```
ctggaagata accatcggca gccatacctg atttaaatca tttattgttc              50


<210> SEQ ID NO 9
<211> LENGTH: 50
<212> TYPE: DNA
<213> ORGANISM: adeno-associated virus 2

<400> SEQUENCE: 9

gaacaataaa tgatttaaat caggtatggc tgccgatggt tatcttccag              50


<210> SEQ ID NO 10
<211> LENGTH: 40
<212> TYPE: DNA
<213> ORGANISM: adeno-associated virus 2

<400> SEQUENCE: 10

ggactctaga gtaacccgat gacgtaagtc ttttatcgcg                         40


<210> SEQ ID NO 11
<211> LENGTH: 13804
<212> TYPE: DNA
<213> ORGANISM: adeno-associated virus 2

<400> SEQUENCE: 11

cgggcccccc ctcgaggtcg acggtatcgg gggagctcgc agggtctcca ttttgaagcg     60

ggaggtttga acgcgcagcc gccatgccgg ggttttacga gattgtgatt aaggtcccca    120

gcgaccttga cgggcatctg cccggcattt ctgacagctt tgtgaactgg gtggccgaga    180

aggaatggga gttgccgcca gattctgaca tggatctgaa tctgattgag caggcacccc    240

tgaccgtggc cgagaagctg cagcgcgact ttctgacgga atggcgccgt gtgagtaagg    300

ccccggaggc cctttttcttt gtgcaatttg agaagggaga gagctacttc cacatgcacg    360

tgctcgtgga aaccaccggg gtgaaatcca tggttttggg acgtttcctg agtcagattc    420

gcgaaaaact gattcagaga atttaccgcg ggatcgagcc gactttgcca aactggttcg    480

cggtcacaaa gaccagaaat ggcgccggag gcgggaacaa ggtggtggat gagtgctaca    540

tccccaatta cttgctcccc aaaacccagc ctgagctcca gtgggcgtgg actaatatgg    600

aacagtattt aagcgcctgt ttgaatctca cggagcgtaa acggttggtg gcgcagcatc    660

tgacgcacgt gtcgcagacg caggagcaga acaaagagaa tcagaatccc aattctgatg    720

cgccggtgat cagatcaaaa acttcagcca ggtacatgga gctggtcggg tggctcgtgg    780

acaaggggat tacctcggag aagcagtgga tccaggagga ccaggcctca tacatctcct    840

tcaatgcggc ctccaactcg cggtcccaaa tcaaggctgc cttggacaat gcgggaaaga    900

ttatgagcct gactaaaacc gcccccgact acctggtggg ccagcagccc gtggaggaca    960

tttccagcaa tcggatttat aaaattttgg aactaaacgg gtacgatccc caatatgcgg   1020

cttccgtctt tctgggatgg gccacgaaaa agttcggcaa gaggaacacc atctggctgt   1080

ttgggcctgc aactaccggg aagaccaaca tcgcggaggc catagcccac actgtgccct   1140

tctacgggtg cgtaaactgg accaatgaga actttccctt caacgactgt gtcgacaaga   1200

tggtgatctg gtgggaggag gggaagatga ccgccaaggt cgtggagtcg gccaaagcca   1260

ttctcggagg aagcaaggtg cgcgtggacc agaaatgcaa gtcctcggcc cagatagacc   1320

cgactcccgt gatcgtcacc tccaacacca acatgtgcgc cgtgattgac gggaactcaa   1380

cgaccttcga acaccagcag ccgttgcaag accggatgtt caaatttgaa ctcacccgcc   1440

gtctggatca tgactttggg aaggtcacca agcaggaagt caaagacttt ttccggtggg   1500
```

-continued

```
caaaggatca cgtggttgag gtggagcatg aattctacgt caaaaagggt ggagccaaga   1560
aaagacccgc ccccagtgac gcagatataa gtgagcccaa acgggtgcgc gagtcagttg   1620
cgcagccatc gacgtcagac gcggaagctt cgatcaacta cgcagacagg taccaaaaca   1680
aatgttctcg tcacgtgggc atgaatctga tgctgtttcc ctgcagacaa tgcgagagaa   1740
tgaatcagaa ttcaaatatc tgcttcactc acggacagaa agactgttta gagtgctttc   1800
ccgtgtcaga atctcaaccc gtttctgtcg tcaaaaaggc gtatcagaaa ctgtgctaca   1860
ttcatcatat catgggaaag gtgccagacg cttgcactgc ctgcgatctg gtcaatgtgg   1920
atttggatga ctgcatcttt gaacaataaa tgatttaaat caggtatggc tgccgatggt   1980
tatcttccag attggctcga ggacaacctc tctgagggca ttcgcgagtg gtgggacttg   2040
aaacctggag ccccgaagcc caaagccaac cagcaaaagc aggacgacgg ccggggtctg   2100
gtgcttcctg gctacaagta cctcggaccc ttcaacggac tcgacaaggg ggagcccgtc   2160
aacgcggcgg acgcagcggc cctcgagcac gacaaggcct acgaccagca gctcaaagcg   2220
ggtgacaatc cgtacctgcg gtataaccac gccgacgccg agtttcagga gcgtctgcaa   2280
gaagatacgt cttttggggg caacctcggg cgagcagtct tccaggccaa gaagcgggtt   2340
ctcgaacctc tcggtctggt tgaggaaggc gctaagacgg ctcctggaaa gaaacgtccg   2400
gtagagcagt cgccacaaga gccagactcc tcctcgggca tcggcaagac aggccagcag   2460
cccgctaaaa agagactcaa ttttggtcag actggcgact cagagtcagt ccccgatcca   2520
caacctctcg gagaacctcc agcaaccccc gctgctgtgg gacctactac aatggcttca   2580
ggcggtggcg caccaatggc agacaataac gaaggcgccg acggagtggg taatgcctca   2640
ggaaattggc attgcgattc cacatggctg ggcgacagag tcatcaccac cagcacccgc   2700
acctgggcct tgcccaccta caataaccac ctctacaagc aaatctccag tgcttcaacg   2760
ggggccagca acgacaacca ctacttcggc tacagcaccc cctgggggta ttttgatttc   2820
aacagattcc actgccactt ttcaccacgt gactggcagc gactcatcaa caacaattgg   2880
ggattccggc ccaagagact caacttcaaa ctcttcaaca tccaagtcaa ggaggtcacg   2940
acgaatgatg gcgtcacaac catcgctaat aaccttacca gcacggttca agtcttctcg   3000
gactcggagt accagcttcc gtacgtcctc ggctctgcgc accagggctg cctccctccg   3060
ttcccggcgg acgtgttcat gattccgcaa tacggctacc tgacgctcaa caatggcagc   3120
caagccgtgg gacgttcatc cttttactgc ctggaatatt tcccttctca gatgctgaga   3180
acgggcaaca actttacctt cagctacacc tttgaggaag tgcctttcca cagcagctac   3240
gcgcacagcc agagcctgga ccggctgatg aatcctctca tcgaccaata cctgtattac   3300
ctgaacagaa ctcaaaatca gtccggaagt gcccaaaaca aggacttgct gtttagccgt   3360
gggtctccag ctggcatgtc tgttcagccc aaaaactggc tacctggacc ctgttatcgg   3420
cagcagcgcg tttctaaaac aaaaacagac aacaacaaca gcaattttac ctggactggt   3480
gcttcaaaat ataacctcaa tgggcgtgaa tccatcatca accctggcac tgctatggcc   3540
tcacacaaag acgacgaaga caagttcttt cccatgagcg gtgtcatgat tttggaaaa    3600
gagagcgccg gagcttcaaa cactgcattg gacaatgtca tgattacaga cgaagaggaa   3660
attaaagcca ctaaccctgt ggccaccgaa agatttggga ccgtggcagt caatttccag   3720
agcagcagca cagaccctgc gaccggagat gtgcatgcta tgggagcatt acctggcatg   3780
gtgtggcaag atagagacgt gtacctgcag ggtcccattt gggccaaaat tcctcacaca   3840
```

-continued

```
gatggacact ttcacccgtc tcctcttatg ggcggctttg gactcaagaa cccgcctcct   3900
cagatcctca tcaaaaacac gcctgttcct gcgaatcctc cggcggagtt ttcagctaca   3960
aagtttgctt cattcatcac ccaatactcc acaggacaag tgagtgtgga aattgaatgg   4020
gagctgcaga aagaaaacag caagcgctgg aatcccgaag tgcagtacac atccaattat   4080
gcaaaatctg ccaacgttga ttttactgtg gacaacaatg gactttatac tgagcctcgc   4140
cccattggca cccgttacct tacccgtccc ctgtaattac gtgttaatca ataaaccggt   4200
tgattcgttt cagttgaact ttggtctcct gtccttctta tcttatcggt taccatggtt   4260
atagcttaca cattaactgc ttggttgcgc ttcgcgataa aagacttacg tcgtagccat   4320
gctctagagg tcctgtatta gaggtcacgt gagtgttttg cgacattttg cgacaccatg   4380
tggtcacgct gggtatttaa gcccgagtga gcacgcaggg tctccatttt gaagcgggag   4440
gtttgaacgc gcagccgcca agccgaattc tgcagatatc catcacactg gcggccgctc   4500
gactagagcg gccgccaccg cggtggagct ccagcttttg ttccctttag tgagggttaa   4560
ttgcgcgctt ggcgtaatca tggtcatagc tgtttcctgt gtgaaattgt tatccgctca   4620
caattccaca caacatacga gccggaagca taaagtgtaa agcctggggt gcctaatgag   4680
tgagctaact cacattaatt gcgttgcgct cactgcccgc tttccagtcg ggaaacctgt   4740
cgtgccagct gcattaatga atcggccaac gcgcggggag aggcggtttg cgtattgggc   4800
gctcttccgc ttcctcgctc actgactcgc tgcgctcggt cgttcggctg cggcgagcgg   4860
tatcagctca ctcaaaggcg gtaatacggt tatccacaga atcaggggat aacgcaggaa   4920
agaacatgtg agcaaaaggc cagcaaaagg ccaggaaccg taaaaaggcc gcgttgctgg   4980
cgtttttcca taggctccgc ccccctgacg agcatcacaa aaatcgacgc tcaagtcaga   5040
ggtggcgaaa cccgacagga ctataaagat accaggcgtt tccccctgga agctccctcg   5100
tgcgctctcc tgttccgacc ctgccgctta ccggatacct gtccgccttt ctcccttcgg   5160
gaagcgtggc gctttctcat agctcacgct gtaggtatct cagttcggtg taggtcgttc   5220
gctccaagct gggctgtgtg cacgaacccc ccgttcagcc cgaccgctgc gccttatccg   5280
gtaactatcg tcttgagtcc aacccggtaa gacacgactt atcgccactg gcagcagcca   5340
ctggtaacag gattagcaga gcgaggtatg taggcggtgc tacagagttc ttgaagtggt   5400
ggcctaacta cggctacact agaaggacag tatttggtat ctgcgctctg ctgaagccag   5460
ttaccttcgg aaaaagagtt ggtagctctt gatccggcaa acaaaccacc gctggtagcg   5520
gtggtttttt tgtttgcaag cagcagatta cgcgcagaaa aaaaggatct caagaagatc   5580
ctttgatctt ttctacgggg tctgacgctc agtggaacga aaactcacgt taagggattt   5640
tggtcatgag attatcaaaa aggatcttca cctagatcct tttaaattaa aaatgaagtt   5700
ttaaatcaat ctaaagtata tatgagtaaa cttggtctga cagttaccaa tgcttaatca   5760
gtgaggcacc tatctcagcg atctgtctat ttcgttcatc catagttgcc tgactccccg   5820
tcgtgtagat aactacgata cgggagggct taccatctgg ccccagtgct gcaatgatac   5880
cgcgagaccc acgctcaccg gctccagatt tatcagcaat aaaccagcca gccggaaggg   5940
ccgagcgcag aagtggtcct gcaactttat ccgcctccat ccagtctatt aattgttgcc   6000
gggaagctag agtaagtagt tcgccagtta atagtttgcg caacgttgtt gccattgcta   6060
caggcatcgt ggtgtcacgc tcgtcgtttg gtatggcttc attcagctcc ggttcccaac   6120
gatcaaggcg agttacatga tcccccatgt tgtgcaaaaa agcggttagc tccttcggtc   6180
ctccgatcgt tgtcagaagt aagttggccg cagtgttatc actcatggtt atggcagcac   6240
```

-continued

```
tgcataattc tcttactgtc atgccatccg taagatgctg cccggcgtca atacgggata   6300
ataccgcgcc acatagcaga actttaaaag tgctcatcat tggaaaacgt tcttcggggc   6360
gaaaactctc aaggatctta ccgctgttga gatccagttc gatgtaaccc actcgtgcac   6420
ccaactgatc ttcagcatct tttactttca ccagcgtttc tgggtgagca aaaacaggaa   6480
ggcacgggcc ccccctcgag gtcgacggta tcgggggagc tcgcagggtc tccattttga   6540
agcgggaggt ttgaacgcgc agccgccatg ccggggtttt acgagattgt gattaaggtc   6600
cccagcgacc ttgacgggca tctgcccggc atttctgaca gctttgtgaa ctgggtggcc   6660
gagaaggaat gggagttgcc gccagattct gacatggatc tgaatctgat tgagcaggca   6720
cccctgaccg tggccgagaa gctgcagcgc gactttctga cggaatggcg ccgtgtgagt   6780
aaggccccgg aggccctttt ctttgtgcaa tttgagaagg gagagagcta cttccacatg   6840
cacgtgctcg tggaaaccac cggggtgaaa tccatggttt tgggacgttt cctgagtcag   6900
attcgcgaaa aactgattca gagaatttac cgcgggatcg agccgacttt gccaaactgg   6960
ttcgcggtca caaagaccag aaatggcgcc ggaggcggga acaaggtggt ggatgagtgc   7020
tacatcccca attacttgct ccccaaaacc cagcctgagc tccagtgggc gtggactaat   7080
atggaacagt atttaagcgc ctgtttgaat ctcacggagc gtaaacggtt ggtggcgcag   7140
catctgacgc acgtgtcgca gacgcaggag cagaacaaag agaatcagaa tcccaattct   7200
gatgcgccgg tgatcagatc aaaaacttca gccaggtaca tggagctggt cgggtggctc   7260
gtggacaagg ggattacctc ggagaagcag tggatccagg aggaccaggc ctcatacatc   7320
tccttcaatg cggcctccaa ctcgcggtcc caaatcaagg ctgccttgga caatgcggga   7380
aagattatga gcctgactaa aaccgccccc gactacctgg tgggccagca gcccgtggag   7440
gacatttcca gcaatcggat ttataaaatt ttggaactaa acgggtacga tccccaatat   7500
gcggcttccg tctttctggg atgggccacg aaaaagttcg gcaagaggaa caccatctgg   7560
ctgtttgggc ctgcaactac cgggaagacc aacatcgcgg aggccatagc ccacactgtg   7620
cccttctacg ggtgcgtaaa ctggaccaat gagaactttc ccttcaacga ctgtgtcgac   7680
aagatggtga tctggtggga ggaggggaag atgaccgcca aggtcgtgga gtcggccaaa   7740
gccattctcg gaggaagcaa ggtgcgcgtg gaccagaaat gcaagtcctc ggcccagata   7800
gacccgactc ccgtgatcgt cacctccaac accaacatgt gcgccgtgat tgacgggaac   7860
tcaacgacct tcgaacacca gcagccgttg caagaccgga tgttcaaatt tgaactcacc   7920
cgccgtctgg atcatgactt tgggaaggtc accaagcagg aagtcaaaga ctttttccgg   7980
tgggcaaagg atcacgtggt tgaggtggag catgaattct acgtcaaaaa gggtggagcc   8040
aagaaaagac ccgcccccag tgacgcagat ataagtgagc ccaaacgggt gcgcgagtca   8100
gttgcgcagc catcgacgtc agacgcggaa gcttcgatca actacgcaga caggtaccaa   8160
aacaaatgtt ctcgtcacgt gggcatgaat ctgatgctgt ttccctgcag acaatgcgag   8220
agaatgaatc agaattcaaa tatctgcttc actcacggac agaaagactg tttagagtgc   8280
tttcccgtgt cagaatctca acccgtttct gtcgtcaaaa aggcgtatca gaaactgtgc   8340
tacattcatc atatcatggg aaaggtgcca gacgcttgca ctgcctgcga tctggtcaat   8400
gtggatttgg atgactgcat ctttgaacaa taaatgattt aaatcaggta tggctgccga   8460
tggttatctt ccagattggc tcgaggacaa cctctctgag ggcattcgcg agtggtggga   8520
cttgaaacct ggagccccga agcccaaagc caaccagcaa aagcaggacg acggccgggg   8580
```

-continued

```
tctggtgctt cctggctaca agtacctcgg acccttcaac ggactcgaca agggggagcc   8640
cgtcaacgcg gcggacgcag cggccctcga gcacgacaag gcctacgacc agcagctcaa   8700
agcgggtgac aatccgtacc tgcggtataa ccacgccgac gccgagtttc aggagcgtct   8760
gcaagaagat acgtcttttg gggcaacct cgggcgagca gtcttccagg ccaagaagcg   8820
ggttctcgaa cctctcggtc tggttgagga aggcgctaag acggctcctg gaaagaaacg   8880
tccggtagag cagtcgccac aagagccaga ctcctcctcg ggcatcggca agacaggcca   8940
gcagcccgct aaaaagagac tcaattttgg tcagactggc gactcagagt cagtccccga   9000
tccacaacct ctcggagaac ctccagcaac ccccgctgct gtgggaccta ctacaatggc   9060
ttcaggcggt ggcgcaccaa tggcagacaa taacgaaggc gccgacggag tgggtaatgc   9120
ctcaggaaat tggcattgcg attccacatg gctgggcgac agagtcatca ccaccagcac   9180
ccgcacctgg gccttgccca cctacaataa ccacctctac aagcaaatct ccagtgcttc   9240
aacgggggcc agcaacgaca accactactt cggctacagc accccctggg ggtattttga   9300
tttcaacaga ttccactgcc acttttcacc acgtgactgg cagcgactca tcaacaacaa   9360
ttggggattc cggcccaaga gactcaactt caaactcttc aacatccaag tcaaggaggt   9420
cacgacgaat gatggcgtca caaccatcgc taataacctt accagcacgg ttcaagtctt   9480
ctcggactcg gagtaccagc ttccgtacgt cctcggctct gcgcaccagg gctgcctccc   9540
tccgttcccg gcggacgtgt tcatgattcc gcaatacggc tacctgacgc tcaacaatgg   9600
cagccaagcc gtgggacgtt catcctttta ctgcctggaa tatttccctt ctcagatgct   9660
gagaacgggc aacaacttta ccttcagcta cacctttgag gaagtgcctt tccacagcag   9720
ctacgcgcac agccagagcc tggaccggct gatgaatcct ctcatcgacc aatacctgta   9780
ttacctgaac agaactcaaa atcagtccgg aagtgcccaa aacaaggact tgctgtttag   9840
ccgtgggtct ccagctggca tgtctgttca gcccaaaaac tggctacctg gaccctgtta   9900
tcggcagcag cgcgtttcta aaacaaaaac agacaacaac aacagcaatt ttacctggac   9960
tggtgcttca aaatataacc tcaatgggcg tgaatccatc atcaaccctg gcactgctat  10020
ggcctcacac aaagacgacg aagacaagtt ctttcccatg agcggtgtca tgatttttgg  10080
aaaagagagc gccggagctt caaacactgc attggacaat gtcatgatta cagacgaaga  10140
ggaaattaaa gccactaacc ctgtggccac cgaaagattt gggaccgtgg cagtcaattt  10200
ccagagcagc agcacagacc ctgcgaccgg agatgtgcat gctatgggag cattacctgg  10260
catggtgtgg caagatagag acgtgtacct gcagggtccc atttgggcca aaattcctca  10320
cacagatgga cactttcacc cgtctcctct tatgggcggc tttggactca agaacccgcc  10380
tcctcagatc ctcatcaaaa acacgcctgt tcctgcgaat cctccggcgg agttttcagc  10440
tacaaagttt gcttcattca tcacccaata ctccacagga caagtgagtg tggaaattga  10500
atgggagctg cagaaagaaa acagcaagcg ctggaatccc gaagtgcagt acacatccaa  10560
ttatgcaaaa tctgccaacg ttgattttac tgtggacaac aatggacttt atactgagcc  10620
tcgccccatt ggcacccgtt accttacccg tcccctgtaa ttacgtgtta atcaataaac  10680
cggttgattc gtttcagttg aactttggtc tcctgtcctt cttatcttat cggttaccat  10740
ggttatagct tacacattaa ctgcttggtt gcgcttcgcg ataaaagact tacgtcgtag  10800
ccatgctcta gaggtcctgt attagaggtc acgtgagtgt tttgcgacat tttgcgacac  10860
catgtggtca cgctgggtat ttaagcccga gtgagcacgc agggtctcca ttttgaagcg  10920
ggaggtttga acgcgcagcc gccaagccga attctgcaga tatccatcac actggcggcc  10980
```

-continued

```
gctcgactag agcggccgcc accgcggtgg agctccagct tttgttccct ttagtgaggg  11040
ttaattgcgc gcttggcgta atcatggtca tagctgtttc ctgtgtgaaa ttgttatccg  11100
ctcacaattc cacacaacat acgagccgga agcataaagt gtaaagcctg gggtgcctaa  11160
tgagtgagct aactcacatt aattgcgttg cgctcactgc ccgctttcca gtcgggaaac  11220
ctgtcgtgcc agctgcatta atgaatcggc caacgcgcgg ggagaggcgg tttgcgtatt  11280
gggcgctctt ccgcttcctc gctcactgac tcgctgcgct cggtcgttcg gctgcggcga  11340
gcggtatcag ctcactcaaa ggcggtaata cggttatcca cagaatcagg ggataacgca  11400
ggaaagaaca tgtgagcaaa aggccagcaa aaggccagga accgtaaaaa ggccgcgttg  11460
ctggcgtttt tccataggct ccgcccccct gacgagcatc acaaaaatcg acgctcaagt  11520
cagaggtggc gaaacccgac aggactataa agataccagg cgtttccccc tggaagctcc  11580
ctcgtgcgct ctcctgttcc gaccctgccg cttaccggat acctgtccgc ctttctccct  11640
tcgggaagcg tggcgctttc tcatagctca cgctgtaggt atctcagttc ggtgtaggtc  11700
gttcgctcca agctgggctg tgtgcacgaa ccccccgttc agcccgaccg ctgcgcctta  11760
tccggtaact atcgtcttga gtccaacccg gtaagacacg acttatcgcc actggcagca  11820
gccactggta acaggattag cagagcgagg tatgtaggcg gtgctacaga gttcttgaag  11880
tggtggccta actacggcta cactagaagg acagtatttg gtatctgcgc tctgctgaag  11940
ccagttacct tcggaaaaag agttggtagc tcttgatccg gcaaacaaac caccgctggt  12000
agcggtggtt tttttgtttg caagcagcag attacgcgca gaaaaaaagg atctcaagaa  12060
gatcctttga tcttttctac ggggtctgac gctcagtgga acgaaaactc acgttaaggg  12120
attttggtca tgagattatc aaaaaggatc ttcacctaga tccttttaaa ttaaaaatga  12180
agttttaaat caatctaaag tatatatgag taaacttggt ctgacagtta ccaatgctta  12240
atcagtgagg cacctatctc agcgatctgt ctatttcgtt catccatagt tgcctgactc  12300
cccgtcgtgt agataactac gatacgggag ggcttaccat ctggccccag tgctgcaatg  12360
ataccgcgag acccacgctc accggctcca gatttatcag caataaacca gccagccgga  12420
agggccgagc gcagaagtgg tcctgcaact ttatccgcct ccatccagtc tattaattgt  12480
tgccgggaag ctagagtaag tagttcgcca gttaatagtt tgcgcaacgt tgttgccatt  12540
gctacaggca tcgtggtgtc acgctcgtcg tttggtatgg cttcattcag ctccggttcc  12600
caacgatcaa ggcgagttac atgatccccc atgttgtgca aaaaagcggt tagctccttc  12660
ggtcctccga tcgttgtcag aagtaagttg gccgcagtgt tatcactcat ggttatggca  12720
gcactgcata attctcttac tgtcatgcca tccgtaagat gctgcccggc gtcaatacgg  12780
gataataccg cgccacatag cagaacttta aaagtgctca tcattggaaa acgttcttcg  12840
gggcgaaaac tctcaaggat cttaccgctg ttgagatcca gttcgatgta acccactcgt  12900
gcacccaact gatcttcagc atcttttact ttcaccagcg tttctgggtg agcaaaaaca  12960
ggaaggcaaa atgccgcaaa aaagggaata agggcgacac ggaaatgttg aatactcata  13020
ctcttccttt ttcaatatta ttgaagcatt tatcagggtt attgtctcat gagcggatac  13080
atatttgaat gtatttagaa aaataaacaa ataggggttc cgcgcacatt tccccgaaaa  13140
gtgccaccta aattgtaagc gttaatattt tgttaaaatt cgcgttaaat ttttgttaaa  13200
tcagctcatt ttttaaccaa taggccgaaa tcggcaaaat cccttataaa tcaaaagaat  13260
agaccgagat agggttgagt gttgttccag tttggaacaa gagtccacta ttaaagaacg  13320
```

-continued

```
tggactccaa cgtcaaaggg cgaaaaaccg tctatcaggg cgatggccca ctacgtgaac  13380

catcacccta atcaagtttt ttggggtcga ggtgccgtaa agcactaaat cggaacccta  13440

aagggagccc ccgatttaga gcttgacggg gaaagccggc gaacgtggcg agaaaggaag  13500

ggaagaaagc gaaaggagcg ggcgctaggg cgctggcaag tgtagcggtc acgctgcgcg  13560

taaccaccac acccgccgcg cttaatgcgc cgctacaggg cgcgtcccat tcgccattca  13620

ggctgcgcaa ctgttgggaa gggcgatcgg tgcgggcctc ttcgctatta cgccagctgg  13680

cgaaaggggg atgtgctgca aggcgattaa gttgggtaac gccagggttt tcccagtcac  13740

gacgttgtaa aacgacggcc agtgagcgcg cgtaatacga ctcactatag ggcgaattgg  13800

gtac                                                                13804
```

<210> SEQ ID NO 12
<211> LENGTH: 50
<212> TYPE: DNA
<213> ORGANISM: adeno-associated virus 2

<400> SEQUENCE: 12

```
gaacaataaa tgatttaaat caggtatgtc ttttgttgat caccctccag                 50
```

<210> SEQ ID NO 13
<211> LENGTH: 40
<212> TYPE: DNA
<213> ORGANISM: adeno-associated virus 2

<400> SEQUENCE: 13

```
ggactctaga gaccacaaga ggcagtattt tactgacacg                            40
```

<210> SEQ ID NO 14
<211> LENGTH: 13676
<212> TYPE: DNA
<213> ORGANISM: adeno-associated virus 2

<400> SEQUENCE: 14

```
cgggcccccc ctcgaggtcg acggtatcgg gggagctcgc agggtctcca ttttgaagcg     60

ggaggtttga acgcgcagcc gccatgccgg ggttttacga gattgtgatt aaggtcccca    120

gcgaccttga cgggcatctg cccggcattt ctgacagctt tgtgaactgg gtggccgaga    180

aggaatggga gttgccgcca gattctgaca tggatctgaa tctgattgag caggcacccc    240

tgaccgtggc cgagaagctg cagcgcgact ttctgacgga atggcgccgt gtgagtaagg    300

ccccggaggc ccttttcttt gtgcaatttg agaagggaga gagctacttc cacatgcacg    360

tgctcgtgga aaccaccggg gtgaaatcca tggttttggg acgtttcctg agtcagattc    420

gcgaaaaact gattcagaga atttaccgcg ggatcgagcc gactttgcca aactggttcg    480

cggtcacaaa gaccagaaat ggcgccggag gcgggaacaa ggtggtggat gagtgctaca    540

tccccaatta cttgctcccc aaaacccagc ctgagctcca gtgggcgtgg actaatatgg    600

aacagtattt aagcgcctgt ttgaatctca cggagcgtaa acggttggtg gcgcagcatc    660

tgacgcacgt gtcgcagacg caggagcaga acaaagagaa tcagaatccc aattctgatg    720

cgccggtgat cagatcaaaa acttcagcca ggtacatgga gctggtcggg tggctcgtgg    780

acaaggggat tacctcggag aagcagtgga tccaggagga ccaggcctca tacatctcct    840

tcaatgcggc ctccaactcg cggtcccaaa tcaaggctgc cttggacaat gcgggaaaga    900

ttatgagcct gactaaaacc gcccccgact acctggtggg ccagcagccc gtggaggaca    960

tttccagcaa tcggatttat aaaattttgg aactaaacgg gtacgatccc caatatgcgg   1020
```

-continued

```
cttccgtctt tctgggatgg gccacgaaaa agttcggcaa gaggaacacc atctggctgt   1080
ttgggcctgc aactaccggg aagaccaaca tcgcggaggc catagcccac actgtgccct   1140
tctacgggtg cgtaaactgg accaatgaga actttccctt caacgactgt gtcgacaaga   1200
tggtgatctg gtgggaggag gggaagatga ccgccaaggt cgtggagtcg gccaaagcca   1260
ttctcggagg aagcaaggtg cgcgtggacc agaaatgcaa gtcctcggcc cagatagacc   1320
cgactcccgt gatcgtcacc tccaacacca acatgtgcgc cgtgattgac gggaactcaa   1380
cgaccttcga acaccagcag ccgttgcaag accggatgtt caaatttgaa ctcacccgcc   1440
gtctggatca tgactttggg aaggtcacca agcaggaagt caaagacttt ttccggtggg   1500
caaaggatca cgtggttgag gtggagcatg aattctacgt caaaaagggt ggagccaaga   1560
aaagacccgc ccccagtgac gcagatataa gtgagcccaa acgggtgcgc gagtcagttg   1620
cgcagccatc gacgtcagac gcggaagctt cgatcaacta cgcagacagg taccaaaaca   1680
aatgttctcg tcacgtgggc atgaatctga tgctgtttcc ctgcagacaa tgcgagagaa   1740
tgaatcagaa ttcaaatatc tgcttcactc acggacagaa agactgttta gagtgctttc   1800
ccgtgtcaga atctcaaccc gtttctgtcg tcaaaaaggc gtatcagaaa ctgtgctaca   1860
ttcatcatat catgggaaag gtgccagacg cttgcactgc ctgcgatctg gtcaatgtgg   1920
atttggatga ctgcatcttt gaacaataaa tgatttaaat caggtatgtc ttttgttgat   1980
caccctccag attggttgga agaagttggt gaaggtcttc gcgagttttt gggccttgaa   2040
gcgggcccac cgaaaccaaa acccaatcag cagcatcaag atcaagcccg tggtcttgtg   2100
ctgcctggtt ataactatct cggacccgga aacggtctcg atcgaggaga gcctgtcaac   2160
agggcagacg aggtcgcgcg agagcacgac atctcgtaca acgagcagct tgaggcggga   2220
gacaacccct acctcaagta caaccacgcg gacgccgagt ttcaggagaa gctcgccgac   2280
gacacatcct tcgggggaaa cctcggaaag gcagtctttc aggccaagaa aagggttctc   2340
gaaccttttg gcctggttga agagggtgct aagacggccc ctaccggaaa gcggatagac   2400
gaccactttc caaaaagaaa gaaggctcgg accgaagagg actccaagcc ttccacctcg   2460
tcagacgccg aagctggacc cagcggatcc cagcagctgc aaatcccagc ccaaccagcc   2520
tcaagtttgg gagctgatac aatgtctgcg ggaggtggcg gcccattggg cgacaataac   2580
caaggtgccg atggagtggg caatgcctcg ggagattggc attgcgattc cacgtggatg   2640
ggggacagag tcgtcaccaa gtccacccga acctgggtgc tgcccagcta caacaaccac   2700
cagtaccgag agatcaaaag cggctccgtc gacggaagca acgccaacgc ctactttgga   2760
tacagcaccc cctgggggta ctttgacttt aaccgcttcc acagccactg gagcccccga   2820
gactggcaaa gactcatcaa caactactgg ggcttcagac cccggtccct cagagtcaaa   2880
atcttcaaca ttcaagtcaa agaggtcacg gtgcaggact ccaccaccac catcgccaac   2940
aacctcacct ccaccgtcca agtgtttacg gacgacgact accagctgcc ctacgtcgtc   3000
ggcaacggga ccgagggatg cctgccggcc ttccctccgc aggtctttac gctgccgcag   3060
tacggttacg cgacgctgaa ccgcgacaac acagaaaatc ccaccgagag gagcagcttc   3120
ttctgcctag agtactttcc cagcaagatg ctgagaacgg gcaacaactt tgagtttacc   3180
tacaactttg aggaggtgcc cttccactcc agcttcgctc ccagtcagaa cctgttcaag   3240
ctggccaacc cgctggtgga ccagtacttg taccgcttcg tgagcacaaa taacactggc   3300
ggagtccagt tcaacaagaa cctggccggg agatacgcca acacctacaa aaactggttc   3360
```

-continued

```
ccggggccca tgggccgaac ccagggctgg aacctgggct ccggggtcaa ccgcgccagt   3420
gtcagcgcct tcgccacgac caataggatg gagctcgagg gcgcgagtta ccaggtgccc   3480
ccgcagccga acggcatgac caacaacctc cagggcagca acacctatgc cctggagaac   3540
actatgatct tcaacagcca gccggcgaac ccgggcacca ccgccacgta cctcgagggc   3600
aacatgctca tcaccagcga gagcgagacg cagccggtga accgcgtggc gtacaacgtc   3660
ggcgggcaga tggccaccaa caaccagagc tccaccactg cccccgcgac cggcacgtac   3720
aacctccagg aaatcgtgcc cggcagcgtg tggatggaga gggacgtgta cctccaagga   3780
cccatctggg ccaagatccc agagacgggg gcgcactttc acccctctcc ggccatgggc   3840
ggattcggac tcaaacaccc accgcccatg atgctcatca agaacacgcc tgtgcccgga   3900
aatatcacca gcttctcgga cgtgcccgtc agcagcttca tcacccagta cagcaccggg   3960
caggtcaccg tggagatgga gtgggagctc aagaaggaaa actccaagag gtggaaccca   4020
gagatccagt acacaaacaa ctacaacgac ccccagtttg tggactttgc cccggacagc   4080
accggggaat acagaaccac cagacctatc ggaacccgat accttacccg acccctttaa   4140
cccattcatg tcgcataccc tcaataaacc gtgtattcgt gtcagtaaaa tactgcctct   4200
tgtggtcatt caatgaataa cagcttacaa catcgtagcc atgctctaga ggtcctgtat   4260
tagaggtcac gtgagtgttt tgcgacattt tgcgacacca tgtggtcacg ctgggtattt   4320
aagcccgagt gagcacgcag ggtctccatt ttgaagcggg aggtttgaac gcgcagccgc   4380
caagccgaat tctgcagata tccatcacac tggcggccgc tcgactagag cggccgccac   4440
cgcggtggag ctccagcttt tgttcccttt agtgagggtt aattgcgcgc ttggcgtaat   4500
catggtcata gctgtttcct gtgtgaaatt gttatccgct cacaattcca cacaacatac   4560
gagccggaag cataaagtgt aaagcctggg gtgcctaatg agtgagctaa ctcacattaa   4620
ttgcgttgcg ctcactgccc gctttccagt cgggaaacct gtcgtgccag ctgcattaat   4680
gaatcggcca acgcgcgggg agaggcggtt tgcgtattgg gcgctcttcc gcttcctcgc   4740
tcactgactc gctgcgctcg gtcgttcggc tgcggcgagc ggtatcagct cactcaaagg   4800
cggtaatacg gttatccaca gaatcagggg ataacgcagg aaagaacatg tgagcaaaag   4860
gccagcaaaa ggccaggaac cgtaaaaagg ccgcgttgct ggcgtttttc cataggctcc   4920
gcccccctga cgagcatcac aaaaatcgac gctcaagtca gaggtggcga aacccgacag   4980
gactataaag ataccaggcg tttccccctg gaagctccct cgtgcgctct cctgttccga   5040
ccctgccgct taccggatac ctgtccgcct ttctcccttc gggaagcgtg gcgctttctc   5100
atagctcacg ctgtaggtat ctcagttcgg tgtaggtcgt tcgctccaag ctgggctgtg   5160
tgcacgaacc ccccgttcag cccgaccgct gcgccttatc cggtaactat cgtcttgagt   5220
ccaacccggt aagacacgac ttatcgccac tggcagcagc cactggtaac aggattagca   5280
gagcgaggta tgtaggcggt gctacagagt tcttgaagtg gtggcctaac tacggctaca   5340
ctagaaggac agtatttggt atctgcgctc tgctgaagcc agttaccttc ggaaaaagag   5400
ttggtagctc ttgatccggc aaacaaacca ccgctggtag cggtggtttt tttgtttgca   5460
agcagcagat tacgcgcaga aaaaaaggat ctcaagaaga tcctttgatc ttttctacgg   5520
ggtctgacgc tcagtggaac gaaaactcac gttaagggat tttggtcatg agattatcaa   5580
aaaggatctt cacctagatc cttttaaatt aaaaatgaag ttttaaatca atctaaagta   5640
tatatgagta aacttggtct gacagttacc aatgcttaat cagtgaggca cctatctcag   5700
cgatctgtct atttcgttca tccatagttg cctgactccc cgtcgtgtag ataactacga   5760
```

-continued

```
tacgggaggg cttaccatct ggccccagtg ctgcaatgat accgcgagac ccacgctcac   5820
cggctccaga tttatcagca ataaaccagc cagccggaag ggccgagcgc agaagtggtc   5880
ctgcaacttt atccgcctcc atccagtcta ttaattgttg ccgggaagct agagtaagta   5940
gttcgccagt taatagtttg cgcaacgttg ttgccattgc tacaggcatc gtggtgtcac   6000
gctcgtcgtt tggtatggct tcattcagct ccggttccca acgatcaagg cgagttacat   6060
gatcccccat gttgtgcaaa aaagcggtta gctccttcgg tcctccgatc gttgtcagaa   6120
gtaagttggc cgcagtgtta tcactcatgg ttatggcagc actgcataat tctcttactg   6180
tcatgccatc cgtaagatgc tgcccggcgt caatacggga taataccgcg ccacatagca   6240
gaactttaaa agtgctcatc attggaaaac gttcttcggg gcgaaaactc tcaaggatct   6300
taccgctgtt gagatccagt tcgatgtaac ccactcgtgc acccaactga tcttcagcat   6360
cttttacttt caccagcgtt tctgggtgag caaaaacagg aaggcaaaat gccgcaaaaa   6420
agggaataag ggcgcgggcc cccccctcgag gtcgacggta tcgggggagc tcgcagggtc   6480
tccattttga agcgggaggt ttgaacgcgc agccgccatg ccggggtttt acgagattgt   6540
gattaaggtc cccagcgacc ttgacgggca tctgcccggc atttctgaca gctttgtgaa   6600
ctgggtggcc gagaaggaat gggagttgcc gccagattct gacatggatc tgaatctgat   6660
tgagcaggca cccctgaccg tggccgagaa gctgcagcgc gactttctga cggaatggcg   6720
ccgtgtgagt aaggccccgg aggccctttt ctttgtgcaa tttgagaagg gagagagcta   6780
cttccacatg cacgtgctcg tggaaaccac cggggtgaaa tccatggttt tgggacgttt   6840
cctgagtcag attcgcgaaa aactgattca gagaatttac cgcgggatcg agccgacttt   6900
gccaaactgg ttcgcggtca caaagaccag aaatggcgcc ggaggcggga acaaggtggt   6960
ggatgagtgc tacatcccca attacttgct ccccaaaacc cagcctgagc tccagtgggc   7020
gtggactaat atggaacagt atttaagcgc ctgtttgaat ctcacggagc gtaaacggtt   7080
ggtggcgcag catctgacgc acgtgtcgca gacgcaggag cagaacaaag agaatcagaa   7140
tcccaattct gatgcgccgg tgatcagatc aaaaacttca gccaggtaca tggagctggt   7200
cgggtggctc gtggacaagg ggattacctc ggagaagcag tggatccagg aggaccaggc   7260
ctcatacatc tccttcaatg cggcctccaa ctcgcggtcc caaatcaagg ctgccttgga   7320
caatgcggga aagattatga gcctgactaa aaccgccccc gactacctgg tgggccagca   7380
gcccgtggag gacatttcca gcaatcggat ttataaaatt ttggaactaa acgggtacga   7440
tccccaatat gcggcttccg tctttctggg atgggccacg aaaaagttcg gcaagaggaa   7500
caccatctgg ctgtttgggc ctgcaactac cgggaagacc aacatcgcgg aggccatagc   7560
ccacactgtg cccttctacg ggtgcgtaaa ctggaccaat gagaactttc ccttcaacga   7620
ctgtgtcgac aagatggtga tctggtggga ggaggggaag atgaccgcca aggtcgtgga   7680
gtcggccaaa gccattctcg gaggaagcaa ggtgcgcgtg gaccagaaat gcaagtcctc   7740
ggcccagata gacccgactc ccgtgatcgt cacctccaac accaacatgt gcgccgtgat   7800
tgacgggaac tcaacgacct tcgaacacca gcagccgttg caagaccgga tgttcaaatt   7860
tgaactcacc cgccgtctgg atcatgactt tgggaaggtc accaagcagg aagtcaaaga   7920
ctttttccgg tgggcaaagg atcacgtggt tgaggtggag catgaattct acgtcaaaaa   7980
gggtggagcc aagaaaagac ccgcccccag tgacgcagat ataagtgagc ccaaacgggt   8040
gcgcgagtca gttgcgcagc catcgacgtc agacgcggaa gcttcgatca actacgcaga   8100
```

-continued

```
caggtaccaa aacaaatgtt ctcgtcacgt gggcatgaat ctgatgctgt ttccctgcag   8160
acaatgcgag agaatgaatc agaattcaaa tatctgcttc actcacggac agaaagactg   8220
tttagagtgc tttcccgtgt cagaatctca acccgtttct gtcgtcaaaa aggcgtatca   8280
gaaactgtgc tacattcatc atatcatggg aaaggtgcca gacgcttgca ctgcctgcga   8340
tctggtcaat gtggatttgg atgactgcat ctttgaacaa taaatgattt aaatcaggta   8400
tgtcttttgt tgatcaccct ccagattggt tggaagaagt tggtgaaggt cttcgcgagt   8460
ttttgggcct tgaagcgggc ccaccgaaac caaaacccaa tcagcagcat caagatcaag   8520
cccgtggtct tgtgctgcct ggttataact atctcggacc cggaaacggt ctcgatcgag   8580
gagagcctgt caacagggca gacgaggtcg cgcgagagca cgacatctcg tacaacgagc   8640
agcttgaggc gggagacaac ccctacctca agtacaacca cgcggacgcc gagtttcagg   8700
agaagctcgc cgacgacaca tccttcgggg gaaacctcgg aaaggcagtc tttcaggcca   8760
agaaaagggt tctcgaacct tttggcctgg ttgaagaggg tgctaagacg gcccctaccg   8820
gaaagcggat agacgaccac tttccaaaaa gaaagaaggc tcggaccgaa gaggactcca   8880
agccttccac ctcgtcagac gccgaagctg gacccagcgg atcccagcag ctgcaaatcc   8940
cagcccaacc agcctcaagt ttgggagctg atacaatgtc tgcgggaggt ggcggcccat   9000
tgggcgacaa taaccaaggt gccgatggag tgggcaatgc ctcgggagat tggcattgcg   9060
attccacgtg gatgggggac agagtcgtca ccaagtccac ccgaacctgg gtgctgccca   9120
gctacaacaa ccaccagtac cgagagatca aaagcggctc cgtcgacgga agcaacgcca   9180
acgcctactt tggatacagc accccctggg ggtactttga ctttaaccgc ttccacagcc   9240
actggagccc ccgagactgg caaagactca tcaacaacta ctggggcttc agaccccggt   9300
ccctcagagt caaaatcttc aacattcaag tcaaagaggt cacggtgcag gactccacca   9360
ccaccatcgc caacaacctc acctccaccg tccaagtgtt tacggacgac gactaccagc   9420
tgccctacgt cgtcggcaac gggaccgagg gatgcctgcc ggccttccct ccgcaggtct   9480
ttacgctgcc gcagtacggt tacgcgacgc tgaaccgcga caacacagaa aatcccaccg   9540
agaggagcag cttcttctgc ctagagtact ttcccagcaa gatgctgaga acgggcaaca   9600
actttgagtt tacctacaac tttgaggagg tgcccttcca ctccagcttc gctcccagtc   9660
agaacctgtt caagctggcc aacccgctgg tggaccagta cttgtaccgc ttcgtgagca   9720
caaataacac tggcggagtc cagttcaaca agaacctggc cgggagatac gccaacacct   9780
acaaaaactg gttcccgggg cccatgggcc gaacccaggg ctggaacctg ggctccgggg   9840
tcaaccgcgc cagtgtcagc gccttcgcca cgaccaatag gatggagctc gagggcgcga   9900
gttaccaggt gcccccgcag ccgaacggca tgaccaacaa cctccagggc agcaacacct   9960
atgccctgga gaacactatg atcttcaaca gccagccggc gaacccgggc accaccgcca  10020
cgtacctcga gggcaacatg ctcatcacca gcgagagcga gacgcagccg gtgaaccgcg  10080
tggcgtacaa cgtcggcggg cagatggcca ccaacaacca gagctccacc actgcccccg  10140
cgaccggcac gtacaacctc caggaaatcg tgcccggcag cgtgtggatg gagagggacg  10200
tgtacctcca aggacccatc tgggccaaga tcccagagac gggggcgcac tttcacccct  10260
ctccggccat gggcggattc ggactcaaac acccaccgcc catgatgctc atcaagaaca  10320
cgcctgtgcc cggaaatatc accagcttct cggacgtgcc cgtcagcagc ttcatcaccc  10380
agtacagcac cgggcaggtc accgtggaga tggagtggga gctcaagaag gaaaactcca  10440
agaggtggaa cccagagatc cagtacacaa acaactacaa cgacccccag tttgtggact  10500
```

-continued

```
ttgccccgga cagcaccggg gaatacagaa ccaccagacc tatcggaacc cgatacctta  10560
cccgacccct ttaacccatt catgtcgcat accctcaata aaccgtgtat tcgtgtcagt  10620
aaaatactgc ctcttgtggt cattcaatga ataacagctt acaacatcgt agccatgctc  10680
tagaggtcct gtattagagg tcacgtgagt gttttgcgac attttgcgac accatgtggt  10740
cacgctgggt atttaagccc gagtgagcac gcagggtctc cattttgaag cgggaggttt  10800
gaacgcgcag ccgccaagcc gaattctgca gatatccatc acactggcgg ccgctcgact  10860
agagcggccg ccaccgcggt ggagctccag cttttgttcc ctttagtgag ggttaattgc  10920
gcgcttggcg taatcatggt catagctgtt tcctgtgtga aattgttatc cgctcacaat  10980
tccacacaac atacgagccg gaagcataaa gtgtaaagcc tggggtgcct aatgagtgag  11040
ctaactcaca ttaattgcgt tgcgctcact gcccgctttc cagtcgggaa acctgtcgtg  11100
ccagctgcat taatgaatcg gccaacgcgc ggggagaggc ggtttgcgta ttgggcgctc  11160
ttccgcttcc tcgctcactg actcgctgcg ctcggtcgtt cggctgcggc gagcggtatc  11220
agctcactca aaggcggtaa tacggttatc cacagaatca ggggataacg caggaaagaa  11280
catgtgagca aaaggccagc aaaaggccag gaaccgtaaa aaggccgcgt tgctggcgtt  11340
tttccatagg ctccgccccc ctgacgagca tcacaaaaat cgacgctcaa gtcagaggtg  11400
gcgaaacccg acaggactat aaagatacca ggcgtttccc cctggaagct ccctcgtgcg  11460
ctctcctgtt ccgaccctgc cgcttaccgg atacctgtcc gcctttctcc cttcgggaag  11520
cgtggcgctt tctcatagct cacgctgtag gtatctcagt tcggtgtagg tcgttcgctc  11580
caagctgggc tgtgtgcacg aaccccccgt tcagcccgac cgctgcgcct tatccggtaa  11640
ctatcgtctt gagtccaacc cggtaagaca cgacttatcg ccactggcag cagccactgg  11700
taacaggatt agcagagcga ggtatgtagg cggtgctaca gagttcttga agtggtggcc  11760
taactacggc tacactagaa ggacagtatt tggtatctgc gctctgctga agccagttac  11820
cttcggaaaa agagttggta gctcttgatc cggcaaacaa accaccgctg gtagcggtgg  11880
tttttttgtt tgcaagcagc agattacgcg cagaaaaaaa ggatctcaag aagatccttt  11940
gatcttttct acggggtctg acgctcagtg gaacgaaaac tcacgttaag ggattttggt  12000
catgagatta tcaaaaagga tcttcaccta gatcctttta aattaaaaat gaagttttaa  12060
atcaatctaa agtatatatg agtaaacttg gtctgacagt taccaatgct taatcagtga  12120
ggcacctatc tcagcgatct gtctatttcg ttcatccata gttgcctgac tccccgtcgt  12180
gtagataact acgatacggg agggcttacc atctggcccc agtgctgcaa tgataccgcg  12240
agacccacgc tcaccggctc cagatttatc agcaataaac cagccagccg gaagggccga  12300
gcgcagaagt ggtcctgcaa ctttatccgc ctccatccag tctattaatt gttgccggga  12360
agctagagta agtagttcgc cagttaatag tttgcgcaac gttgttgcca ttgctacagg  12420
catcgtggtg tcacgctcgt cgtttggtat ggcttcattc agctccggtt cccaacgatc  12480
aaggcgagtt acatgatccc ccatgttgtg caaaaaagcg gttagctcct tcggtcctcc  12540
gatcgttgtc agaagtaagt tggccgcagt gttatcactc atggttatgg cagcactgca  12600
taattctctt actgtcatgc catccgtaag atgctgcccg gcgtcaatac gggataatac  12660
cgcgccacat agcagaactt taaaagtgct catcattgga aaacgttctt cggggcgaaa  12720
actctcaagg atcttaccgc tgttgagatc cagttcgatg taacccactc gtgcacccaa  12780
ctgatcttca gcatctttta ctttcaccag cgtttctggg tgagcaaaaa caggaaggca  12840
```

-continued

```
aaatgccgca aaaaagggaa taagggcgac acggaaatgt tgaatactca tactcttcct  12900

ttttcaatat tattgaagca tttatcaggg ttattgtctc atgagcggat acatatttga  12960

atgtatttag aaaaataaac aaataggggt tccgcgcaca tttccccgaa aagtgccacc  13020

taaattgtaa gcgttaatat tttgttaaaa ttcgcgttaa atttttgtta aatcagctca  13080

ttttttaacc aataggccga aatcggcaaa atcccttata aatcaaaaga atagaccgag  13140

atagggttga gtgttgttcc agtttggaac aagagtccac tattaaagaa cgtggactcc  13200

aacgtcaaag ggcgaaaaac cgtctatcag ggcgatggcc cactacgtga accatcaccc  13260

taatcaagtt ttttggggtc gaggtgccgt aaagcactaa atcggaaccc taaagggagc  13320

ccccgattta gagcttgacg gggaaagccg gcgaacgtgg cgagaaagga agggaagaaa  13380

gcgaaaggag cgggcgctag ggcgctggca agtgtagcgg tcacgctgcg cgtaaccacc  13440

acacccgccg cgcttaatgc gccgctacag ggcgcgtccc attcgccatt caggctgcgc  13500

aactgttggg aagggcgatc ggtgcgggcc tcttcgctat tacgccagct ggcgaaaggg  13560

ggatgtgctg caaggcgatt aagttgggta acgccagggt tttcccagtc acgacgttgt  13620

aaaacgacgg ccagtgagcg cgcgtaatac gactcactat agggcgaatt gggtac      13676
```

<210> SEQ ID NO 15
<211> LENGTH: 12136
<212> TYPE: DNA
<213> ORGANISM: adeno-associated virus 2

<400> SEQUENCE: 15

```
cgggcccccc ctcgaggtcg acggtatcgg gggagctcgc agggtctcca ttttgaagcg     60

ggaggtttga acgcgcagcc gccatgccgg ggttttacga gattgtgatt aaggtcccca    120

gcgaccttga cgggcatctg cccggcattt ctgacagctt tgtgaactgg gtggccgaga    180

aggaatggga gttgccgcca gattctgaca tggatctgaa tctgattgag caggcacccc    240

tgaccgtggc cgagaagctg cagcgcgact ttctgacgga atggcgccgt gtgagtaagg    300

ccccggaggc ccttttcttt gtgcaatttg agaagggaga gagctacttc cacatgcacg    360

tgctcgtgga aaccaccggg gtgaaatcca tggttttggg acgtttcctg agtcagattc    420

gcgaaaaact gattcagaga atttaccgcg ggatcgagcc gactttgcca aactggttcg    480

cggtcacaaa gaccagaaat ggcgccggag gcgggaacaa ggtggtggat gagtgctaca    540

tccccaatta cttgctcccc aaaacccagc ctgagctcca gtgggcgtgg actaatatgg    600

aacagtattt aagcgcctgt ttgaatctca cggagcgtaa acggttggtg gcgcagcatc    660

tgacgcacgt gtcgcagacg caggagcaga acaaagagaa tcagaatccc aattctgatg    720

cgccggtgat cagatcaaaa acttcagcca ggtacatgga gctggtcggg tggctcgtgg    780

acaaggggat tacctcggag aagcagtgga tccaggagga ccaggcctca tacatctcct    840

tcaatgcggc ctccaactcg cggtcccaaa tcaaggctgc cttggacaat gcgggaaaga    900

ttatgagcct gactaaaacc gcccccgact acctggtggg ccagcagccc gtggaggaca    960

tttccagcaa tcggatttat aaaattttgg aactaaacgg gtacgatccc caatatgcgg   1020

cttccgtctt tctgggatgg gccacgaaaa agttcggcaa gaggaacacc atctggctgt   1080

ttgggcctgc aactaccggg aagaccaaca tcgcggaggc catagcccac actgtgccct   1140

tctacgggtg cgtaaactgg accaatgaga actttccctt caacgactgt gtcgacaaga   1200

tggtgatctg gtgggaggag gggaagatga ccgccaaggt cgtggagtcg gccaaagcca   1260

ttctcggagg aagcaaggtg cgcgtggacc agaaatgcaa gtcctcggcc cagatagacc   1320
```

-continued

```
cgactcccgt gatcgtcacc tccaacacca acatgtgcgc cgtgattgac gggaactcaa   1380
cgaccttcga acaccagcag ccgttgcaag accggatgtt caaatttgaa ctcacccgcc   1440
gtctggatca tgactttggg aaggtcacca agcaggaagt caaagacttt ttccggtggg   1500
caaaggatca cgtggttgag gtggagcatg aattctacgt caaaaagggt ggagccaaga   1560
aaagacccgc ccccagtgac gcagatataa gtgagcccaa acgggtgcgc gagtcagttg   1620
cgcagccatc gacgtcagac gcggaagctt cgatcaacta cgcagacagg taccaaaaca   1680
aatgttctcg tcacgtgggc atgaatctga tgctgtttcc ctgcagacaa tgcgagagaa   1740
tgaatcagaa ttcaaatatc tgcttcactc acggacagaa agactgttta gagtgctttc   1800
ccgtgtcaga atctcaaccc gtttctgtcg tcaaaaaggc gtatcagaaa ctgtgctaca   1860
ttcatcatat catgggaaag gtgccagacg cttgcactgc ctgcgatctg gtcaatgtgg   1920
atttggatga ctgcatcttt gaacaataaa tgatttaaat caggtatggc tgccgatggt   1980
tatcttccag attggctcga ggacactctc tctgaaggaa taagacagtg gtggaagctc   2040
aaacctggcc caccaccacc aaagcccgca gagcggcata aggacgacag caggggtctt   2100
gtgcttcctg ggtacaagta cctcggaccc ttcaacggac tcgacaaggg agagccggtc   2160
aacgaggcag acgccgcggc cctcgagcac gacaaagcct acgaccggca gctcgacagc   2220
ggagacaacc cgtacctcaa gtacaaccac gccgacgcgg agtttcagga gcgccttaaa   2280
gaagatacgt cttttggggg caacctcgga cgagcagtct tccaggcgaa aaagagggtt   2340
cttgaacctc tgggcctggt tgaggaacct gttaagacgg ctccgggaaa aaagaggccg   2400
gtagagcact ctcctgtgga gccagactcc tcctcgggaa ccggaaaggc gggccagcag   2460
cctgcaagaa aaagattgaa ttttggtcag actggagacg cagactcagt acctgacccc   2520
cagcctctcg gacagccacc agcagccccc tctggtctgg gaactaatac gatggctaca   2580
ggcagtggcg caccaatggc agacaataac gagggcgccg acggagtggg taattcctcg   2640
ggaaattggc attgcgattc cacatggatg ggcgacagag tcatcaccac cagcacccga   2700
acctgggccc tgcccaccta caacaaccac ctctacaaac aaatttccag ccaatcagga   2760
gcctcgaacg acaatcacta ctttggctac agcacccctt gggggtattt tgacttcaac   2820
agattccact gccacttttc accacgtgac tggcaaagac tcatcaacaa caactgggga   2880
ttccgaccca agagactcaa cttcaagctc tttaacattc aagtcaaaga ggtcacgcag   2940
aatgacggta cgacgacgat tgccaataac cttaccagca cggttcaggt gtttactgac   3000
tcggagtacc agctcccgta cgtcctcggc tcggcgcatc aaggatgcct cccgccgttc   3060
ccagcagacg tcttcatggt gccacagtat ggatacctca ccctgaacaa cgggagtcag   3120
gcagtaggac gctcttcatt ttactgcctg gagtactttc cttctcagat gctgcgtacc   3180
ggaaacaact ttaccttcag ctacactttt gaggacgttc ctttccacag cagctacgct   3240
cacagccaga gtctggaccg tctcatgaat cctctcatcg accagtacct gtattacttg   3300
agcagaacaa acactccaag tggaaccacc acgcagtcaa ggcttcagtt ttctcaggcc   3360
ggagcgagtg acattcggga ccagtctagg aactggcttc ctggaccctg ttaccgccag   3420
cagcgagtat caaagacatc tgcggataac aacaacagtg aatactcgtg gactggagct   3480
accaagtacc acctcaatgg cagagactct ctggtgaatc cgggcccggc catggcaagc   3540
cacaaggacg atgaagaaaa gtttttttcct cagagcgggg ttctcatctt tgggaagcaa   3600
ggctcagaga aaacaaatgt ggacattgaa aaggtcatga ttacagacga agaggaaatc   3660
```

-continued

```
aggacaacca atcccgtggc tacggagcag tatggttctg tatctaccaa cctccagaga   3720
ggcaacagac aagcagctac cgcagatgtc aacacacaag gcgttcttcc aggcatggtc   3780
tggcaggaca gagatgtgta ccttcagggg cccatctggg caaagattcc acacacggac   3840
ggacattttc acccctctcc cctcatgggt ggattcggac ttaaacaccc tcctccacag   3900
attctcatca agaacacccc ggtacctgcg aatccttcga ccaccttcag tgcggcaaag   3960
tttgcttcct tcatcacaca gtactccacg ggacaggtca gcgtggagat cgagtgggag   4020
ctgcagaagg aaaacagcaa acgctggaat cccgaaattc agtacacttc caactacaac   4080
aagtctgtta atgtggactt tactgtggac actaatggcg tgtattcaga gcctcgcccc   4140
attggcacca gatacctgac tcgtaatctg taattgcttg ttaatcaata aaccgtttaa   4200
ttcgtttcag ttgaactttg gtctctgcgt atttctttct tatctagttt ccatgctcta   4260
ggatccacta gtaacggccg ccagtgtgct ggaattcggc tttgtagtta atgattaacc   4320
cgccatgcta cttatctacg tagccatgca ttcaatgaat aacagcttac aacatcgtag   4380
ccatgctcta gaggtcctgt attagaggtc acgtgagtgt tttgcgacat tttgcgacac   4440
catgtggtca cgctgggtat ttaagcccga gtgagcacgc agggtctcca ttttgaagcg   4500
ggaggtttga acgcgcagcc gccaagccga attctgcaga tatccatcac actggcggcc   4560
gctcgactag agcggccgcc accgcggtgg agctccagct tttgttccct ttagtgaggg   4620
ttaattgcgc gcttggcgta atcatggtca tagctgtttc ctgtgtgaaa ttgttatccg   4680
ctcacaattc cacacaacat acgagccgga agcataaagt gtaaagcctg gggtgcctaa   4740
tgagtgagct aacgggcccc ccctcgaggt cgacggtatc gggggagctc gcagggtctc   4800
cattttgaag cgggaggttt gaacgcgcag ccgccatgcc ggggttttac gagattgtga   4860
ttaaggtccc cagcgacctt gacgggcatc tgcccggcat ttctgacagc tttgtgaact   4920
gggtggccga gaaggaatgg gagttgccgc cagattctga catggatctg aatctgattg   4980
agcaggcacc cctgaccgtg gccgagaagc tgcagcgcga ctttctgacg gaatggcgcc   5040
gtgtgagtaa ggccccggag gcccttttct ttgtgcaatt tgagaaggga gagagctact   5100
tccacatgca cgtgctcgtg gaaaccaccg gggtgaaatc catggttttg ggacgtttcc   5160
tgagtcagat tcgcgaaaaa ctgattcaga gaatttaccg cgggatcgag ccgactttgc   5220
caaactggtt cgcggtcaca aagaccagaa atggcgccgg aggcgggaac aaggtggtgg   5280
atgagtgcta catccccaat tacttgctcc ccaaaaccca gcctgagctc cagtgggcgt   5340
ggactaatat ggaacagtat ttaagcgcct gtttgaatct cacggagcgt aaacggttgg   5400
tggcgcagca tctgacgcac gtgtcgcaga cgcaggagca gaacaaagag aatcagaatc   5460
ccaattctga tgcgccggtg atcagatcaa aaacttcagc caggtacatg gagctggtcg   5520
ggtggctcgt ggacaagggg attacctcgg agaagcagtg gatccaggag gaccaggcct   5580
catacatctc cttcaatgcg gcctccaact cgcggtccca aatcaaggct gccttggaca   5640
atgcgggaaa gattatgagc ctgactaaaa ccgcccccga ctacctggtg ggccagcagc   5700
ccgtggagga catttccagc aatcggattt ataaaatttt ggaactaaac gggtacgatc   5760
cccaatatgc ggcttccgtc tttctgggat gggccacgaa aaagttcggc aagaggaaca   5820
ccatctggct gtttgggcct gcaactaccg ggaagaccaa catcgcggag gccatagccc   5880
acactgtgcc cttctacggg tgcgtaaact ggaccaatga gaactttccc ttcaacgact   5940
gtgtcgacaa gatggtgatc tggtgggagg aggggaagat gaccgccaag gtcgtggagt   6000
cggccaaagc cattctcgga ggaagcaagg tgcgcgtgga ccagaaatgc aagtcctcgg   6060
```

-continued

```
cccagataga cccgactccc gtgatcgtca cctccaacac caacatgtgc gccgtgattg   6120
acgggaactc aacgaccttc gaacaccagc agccgttgca agaccggatg ttcaaatttg   6180
aactcacccg ccgtctggat catgactttg ggaaggtcac caagcaggaa gtcaaagact   6240
ttttccggtg ggcaaaggat cacgtggttg aggtggagca tgaattctac gtcaaaaagg   6300
gtggagccaa gaaaagaccc gcccccagtg acgcagatat aagtgagccc aaacgggtgc   6360
gcgagtcagt tgcgcagcca tcgacgtcag acgcggaagc ttcgatcaac tacgcagaca   6420
ggtaccaaaa caaatgttct cgtcacgtgg gcatgaatct gatgctgttt ccctgcagac   6480
aatgcgagag aatgaatcag aattcaaata tctgcttcac tcacggacag aaagactgtt   6540
tagagtgctt tcccgtgtca gaatctcaac ccgtttctgt cgtcaaaaag gcgtatcaga   6600
aactgtgcta cattcatcat atcatgggaa aggtgccaga cgcttgcact gcctgcgatc   6660
tggtcaatgt ggatttggat gactgcatct ttgaacaata aatgatttaa atcaggtatg   6720
gctgccgatg gttatcttcc agattggctc gaggacactc tctctgaagg aataagacag   6780
tggtggaagc tcaaacctgg cccaccacca ccaaagcccg cagagcggca taaggacgac   6840
agcaggggtc ttgtgcttcc tgggtacaag tacctcggac ccttcaacgg actcgacaag   6900
ggagagccgg tcaacgaggc agacgccgcg gccctcgagc acgacaaagc ctacgaccgg   6960
cagctcgaca gcggagacaa cccgtacctc aagtacaacc acgccgacgc ggagtttcag   7020
gagcgcctta aagaagatac gtcttttggg ggcaacctcg gacgagcagt cttccaggcg   7080
aaaaagaggg ttcttgaacc tctgggcctg gttgaggaac ctgttaagac ggctccggga   7140
aaaaagaggc cggtagagca ctctcctgtg gagccagact cctcctcggg aaccggaaag   7200
gcgggccagc agcctgcaag aaaaagattg aattttggtc agactggaga cgcagactca   7260
gtacctgacc cccagcctct cggacagcca ccagcagccc cctctggtct gggaactaat   7320
acgatggcta caggcagtgg cgcaccaatg gcagacaata acgagggcgc cgacggagtg   7380
ggtaattcct cgggaaattg gcattgcgat tccacatgga tgggcgacag agtcatcacc   7440
accagcaccc gaacctgggc cctgcccacc tacaacaacc acctctacaa acaaatttcc   7500
agccaatcag gagcctcgaa cgacaatcac tactttggct acagcacccc ttgggggtat   7560
tttgacttca acagattcca ctgccacttt tcaccacgtg actggcaaag actcatcaac   7620
aacaactggg gattccgacc caagagactc aacttcaagc tctttaacat tcaagtcaaa   7680
gaggtcacgc agaatgacgg tacgacgacg attgccaata accttaccag cacggttcag   7740
gtgtttactg actcggagta ccagctcccg tacgtcctcg gctcggcgca tcaaggatgc   7800
ctcccgccgt tcccagcaga cgtcttcatg gtgccacagt atggatacct caccctgaac   7860
aacgggagtc aggcagtagg acgctcttca ttttactgcc tggagtactt tccttctcag   7920
atgctgcgta ccggaaacaa ctttaccttc agctacactt ttgaggacgt tcctttccac   7980
agcagctacg ctcacagcca gagtctggac cgtctcatga atcctctcat cgaccagtac   8040
ctgtattact tgagcagaac aaacactcca agtggaacca ccacgcagtc aaggcttcag   8100
ttttctcagg ccggagcgag tgacattcgg gaccagtcta ggaactggct tcctggaccc   8160
tgttaccgcc agcagcgagt atcaaagaca tctgcggata acaacaacag tgaatactcg   8220
tggactggag ctaccaagta ccacctcaat ggcagagact ctctggtgaa tccgggcccg   8280
gccatggcaa gccacaagga cgatgaagaa aagtttttc ctcagagcgg ggttctcatc   8340
tttgggaagc aaggctcaga gaaaacaaat gtggacattg aaaaggtcat gattacagac   8400
```

-continued

```
gaagaggaaa tcaggacaac caatcccgtg gctacggagc agtatggttc tgtatctacc   8460
aacctccaga gaggcaacag acaagcagct accgcagatg tcaacacaca aggcgttctt   8520
ccaggcatgg tctggcagga cagagatgtg taccttcagg ggcccatctg ggcaaagatt   8580
ccacacacgg acggacattt tcacccctct cccctcatgg gtggattcgg acttaaacac   8640
cctcctccac agattctcat caagaacacc ccggtacctg cgaatccttc gaccaccttc   8700
agtgcggcaa agtttgcttc cttcatcaca cagtactcca cgggacaggt cagcgtggag   8760
atcgagtggg agctgcagaa ggaaaacagc aaacgctgga atcccgaaat tcagtacact   8820
tccaactaca acaagtctgt taatgtggac tttactgtgg acactaatgg cgtgtattca   8880
gagcctcgcc ccattggcac cagatacctg actcgtaatc tgtaattgct tgttaatcaa   8940
taaaccgttt aattcgtttc agttgaactt tggtctctgc gtatttcttt cttatctagt   9000
ttccatgctc taggatccac tagtaacggc cgccagtgtg ctggaattcg gctttgtagt   9060
taatgattaa cccgccatgc tacttatcta cgtagccatg cattcaatga ataacagctt   9120
acaacatcgt agccatgctc tagaggtcct gtattagagg tcacgtgagt gttttgcgac   9180
attttgcgac accatgtggt cacgctgggt atttaagccc gagtgagcac gcagggtctc   9240
cattttgaag cgggaggttt gaacgcgcag ccgccaagcc gaattctgca gatatccatc   9300
acactggcgg ccgctcgact agagcggccg ccaccgcggt ggagctccag cttttgttcc   9360
ctttagtgag ggttaattgc gcgcttggcg taatcatggt catagctgtt tcctgtgtga   9420
aattgttatc cgctcacaat tccacacaac atacgagccg gaagcataaa gtgtaaagcc   9480
tggggtgcct aatgagtgag ctaactcaca ttaattgcgt tgcgctcact gcccgctttc   9540
cagtcgggaa acctgtcgtg ccagctgcat taatgaatcg gccaacgcgc ggggagaggc   9600
ggtttgcgta ttgggcgctc ttccgcttcc tcgctcactg actcgctgcg ctcggtcgtt   9660
cggctgcggc gagcggtatc agctcactca aaggcggtaa tacggttatc cacagaatca   9720
ggggataacg caggaaagaa catgtgagca aaaggccagc aaaaggccag gaaccgtaaa   9780
aaggccgcgt tgctggcgtt tttccatagg ctccgccccc ctgacgagca tcacaaaaat   9840
cgacgctcaa gtcagaggtg gcgaaacccg acaggactat aaagatacca ggcgtttccc   9900
cctggaagct ccctcgtgcg ctctcctgtt ccgaccctgc cgcttaccgg atacctgtcc   9960
gcctttctcc cttcgggaag cgtggcgctt tctcatagct cacgctgtag gtatctcagt  10020
tcggtgtagg tcgttcgctc caagctgggc tgtgtgcacg aaccccccgt tcagcccgac  10080
cgctgcgcct tatccggtaa ctatcgtctt gagtccaacc cggtaagaca cgacttatcg  10140
ccactggcag cagccactgg taacaggatt agcagagcga ggtatgtagg cggtgctaca  10200
gagttcttga agtggtggcc taactacggc tacactagaa ggacagtatt tggtatctgc  10260
gctctgctga agccagttac cttcggaaaa agagttggta gctcttgatc cggcaaacaa  10320
accaccgctg gtagcggtgg tttttttgtt tgcaagcagc agattacgcg cagaaaaaaa  10380
ggatctcaag aagatccttt gatcttttct acggggtctg acgctcagtg gaacgaaaac  10440
tcacgttaag ggattttggt catgagatta tcaaaaagga tcttcaccta gatcctttta  10500
aattaaaaat gaagttttaa atcaatctaa agtatatatg agtaaacttg gtctgacagt  10560
taccaatgct taatcagtga ggcacctatc tcagcgatct gtctatttcg ttcatccata  10620
gttgcctgac tccccgtcgt gtagataact acgatacggg agggcttacc atctggcccc  10680
agtgctgcaa tgataccgcg agacccacgc tcaccggctc cagatttatc agcaataaac  10740
cagccagccg gaagggccga gcgcagaagt ggtcctgcaa ctttatccgc ctccatccag  10800
```

-continued

```
tctattaatt gttgccggga agctagagta agtagttcgc cagttaatag tttgcgcaac  10860
gttgttgcca ttgctacagg catcgtggtg tcacgctcgt cgtttggtat ggcttcattc  10920
agctccggtt cccaacgatc aaggcgagtt acatgatccc ccatgttgtg caaaaaagcg  10980
gttagctcct tcggtcctcc gatcgttgtc agaagtaagt tggccgcagt gttatcactc  11040
atggttatgg cagcactgca taattctctt actgtcatgc catccgtaag atgctgcccg  11100
gcgtcaatac gggataatac cgcgccacat agcagaactt taaaagtgct catcattgga  11160
aaacgttctt cggggcgaaa actctcaagg atcttaccgc tgttgagatc cagttcgatg  11220
taacccactc gtgcacccaa ctgatcttca gcatctttta ctttcaccag cgtttctggg  11280
tgagcaaaaa caggaaggca aaatgccgca aaaaagggaa taagggcgac acggaaatgt  11340
tgaatactca tactcttcct ttttcaatat tattgaagca tttatcaggg ttattgtctc  11400
atgagcggat acatatttga atgtatttag aaaaataaac aaataggggt tccgcgcaca  11460
tttccccgaa aagtgccacc taaattgtaa gcgttaatat tttgttaaaa ttcgcgttaa  11520
atttttgtta aatcagctca ttttttaacc aataggccga aatcggcaaa atcccttata  11580
aatcaaaaga atagaccgag atagggttga gtgttgttcc agtttggaac aagagtccac  11640
tattaaagaa cgtggactcc aacgtcaaag ggcgaaaaac cgtctatcag ggcgatggcc  11700
cactacgtga accatcaccc taatcaagtt ttttggggtc gaggtgccgt aaagcactaa  11760
atcggaaccc taaagggagc ccccgattta gagcttgacg gggaaagccg gcgaacgtgg  11820
cgagaaagga agggaagaaa gcgaaaggag cgggcgctag ggcgctggca agtgtagcgg  11880
tcacgctgcg cgtaaccacc acacccgccg cgcttaatgc gccgctacag ggcgcgtccc  11940
attcgccatt caggctgcgc aactgttggg aagggcgatc ggtgcgggcc tcttcgctat  12000
tacgccagct ggcgaaaggg ggatgtgctg caaggcgatt aagttgggta acgccagggt  12060
tttcccagtc acgacgttgt aaaacgacgg ccagtgagcg cgcgtaatac gactcactat  12120
agggcgaatt gggtac                                                  12136
```